United States Patent
Negami et al.

(12) 
(10) Patent No.: US 6,432,364 B1
(45) Date of Patent: Aug. 13, 2002

(54) SPR SENSOR CELL AND IMMUNOASSAY APPARATUS USING THE SAME

(75) Inventors: Mitsuhiro Negami; Muneaki Nakamura; Kazuyasu Suzuki, all of Shizuoka (JP)

(73) Assignee: Suzuki Motor Corporation, Shizuoka (JP)

(*) Notice: Subject to any disclaimer, the term of this patent is extended or adjusted under 35 U.S.C. 154(b) by 0 days.

(21) Appl. No.: 09/348,613

(22) Filed: Jul. 6, 1999

(30) Foreign Application Priority Data

| Jul. 6, 1998 | (JP) | 10-205864 |
| Feb. 7, 1999 | (JP) | 11-032617 |
| May 11, 1999 | (JP) | 11-129668 |
| Jun. 7, 1999 | (JP) | 11-158962 |
| Jun. 16, 1999 | (JP) | 11-169479 |

(51) Int. Cl.[7] ............................ G01N 21/75
(52) U.S. Cl. ............. 422/82.11; 422/82.05; 422/82.06; 422/82.08; 422/82.09; 385/12
(58) Field of Search ............. 422/82.11, 55–58, 422/82.08, 82.09, 82.06, 82.05; 385/12, 31, 39; 436/518

(56) References Cited

U.S. PATENT DOCUMENTS

| 4,750,799 A | * | 6/1988 | Kawachi et al. | 350/96.11 |
| 4,904,037 A | * | 2/1990 | Imoto et al. | 350/96.12 |
| 4,913,519 A | * | 4/1990 | Klainer et al. | 350/96.29 |
| 5,026,139 A | * | 6/1991 | Klainer et al. | 350/96.29 |
| 5,109,442 A | * | 4/1992 | Klainer et al. | 385/12 |
| 5,165,005 A | * | 11/1992 | Klainer et al. | 385/129 |
| 5,253,037 A | * | 10/1993 | Klainer et al. | 356/133 |
| 5,313,264 A | | 5/1994 | Ivarsson et al. | |
| 5,359,681 A | | 10/1994 | Jorgenson et al. | |
| 5,573,956 A | * | 11/1996 | Hanning | 436/518 |
| 5,641,640 A | * | 6/1997 | Hanning | 435/7.92 |
| 5,647,030 A | | 7/1997 | Jorgenson et al. | |
| 5,780,251 A | * | 7/1998 | Klainer et al. | 435/7.93 |
| 5,891,658 A | * | 4/1999 | Klainer et al. | 435/7.93 |
| 5,999,670 A | * | 12/1999 | Yoshimura et al. | 385/31 |
| 6,210,910 B1 | * | 4/2001 | Walt et al. | 435/7.32 |

FOREIGN PATENT DOCUMENTS

| DE | 196 11 025 A1 | 9/1997 |
| WO | WO 97/15819 | 5/1997 |
| WO | WO 97/15820 | 5/1997 |
| WO | WO 98/21571 | 5/1998 |

* cited by examiner

Primary Examiner—Jill Warden
Assistant Examiner—Brian Sines
(74) Attorney, Agent, or Firm—McGinn & Gibb, PLLC

(57) ABSTRACT

An SPR (surface plasmon resonance) sensor cell comprising: a light-transparent core; a clad covering the core and having a through hole at a predetermined position to communicate with the core; and a predetermined thin metal film formed on an exposed surface of the core corresponding to the through hole.

35 Claims, 81 Drawing Sheets

FIG.2
(A)
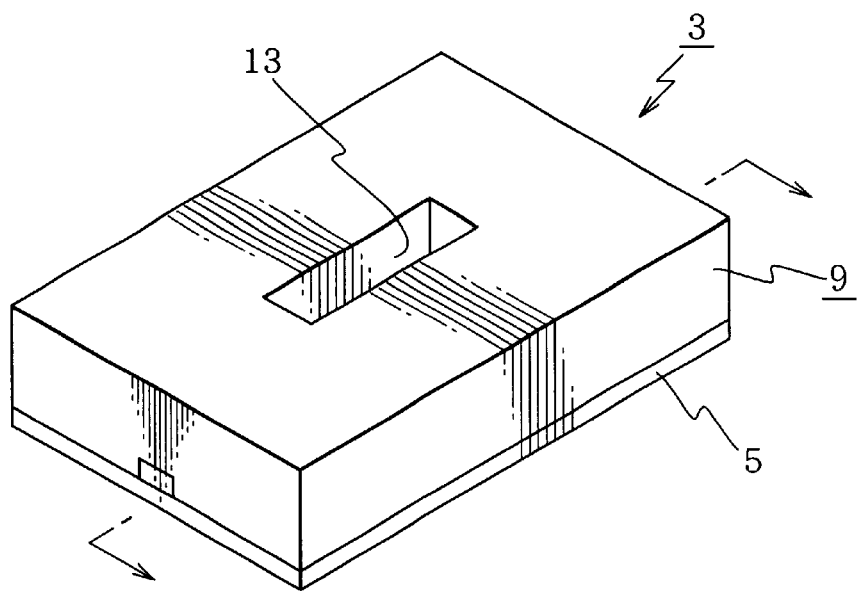
(B)
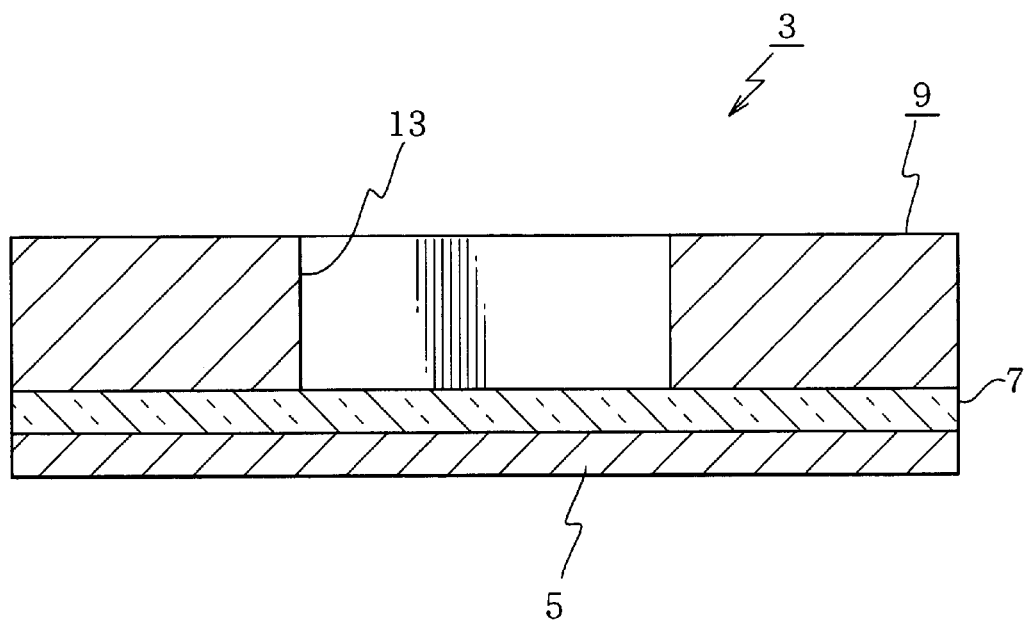

FIG.3
(A)
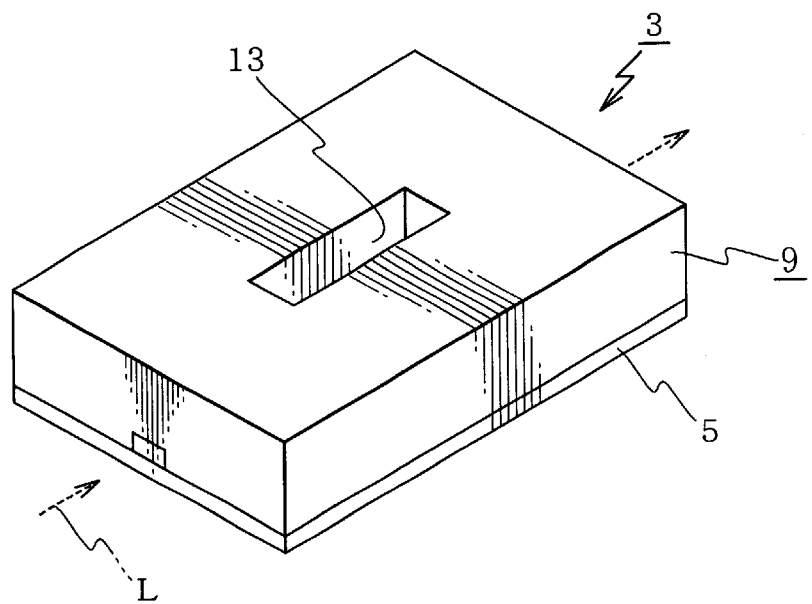
(B)
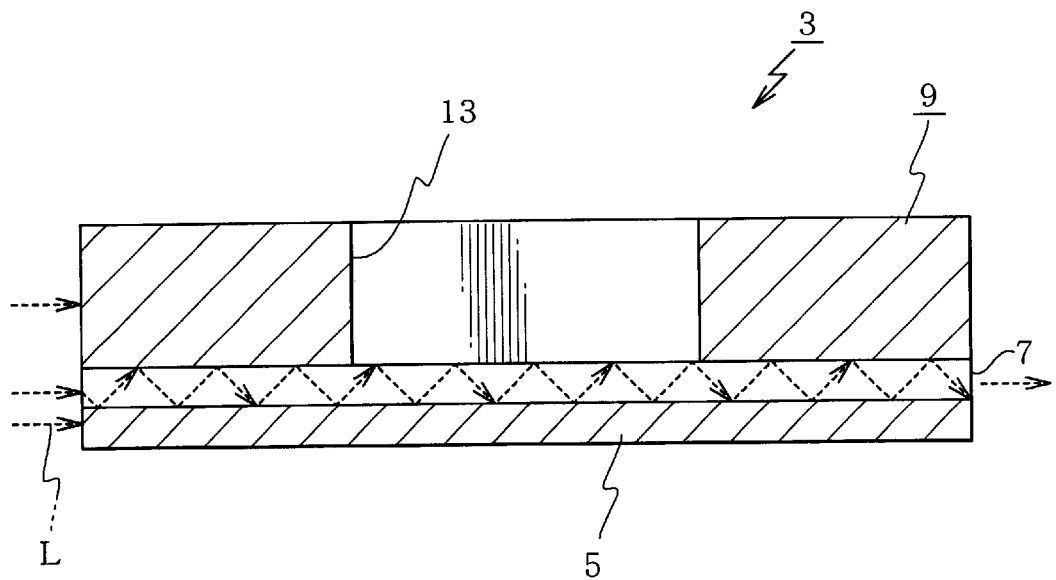

FIG. 4
(A)
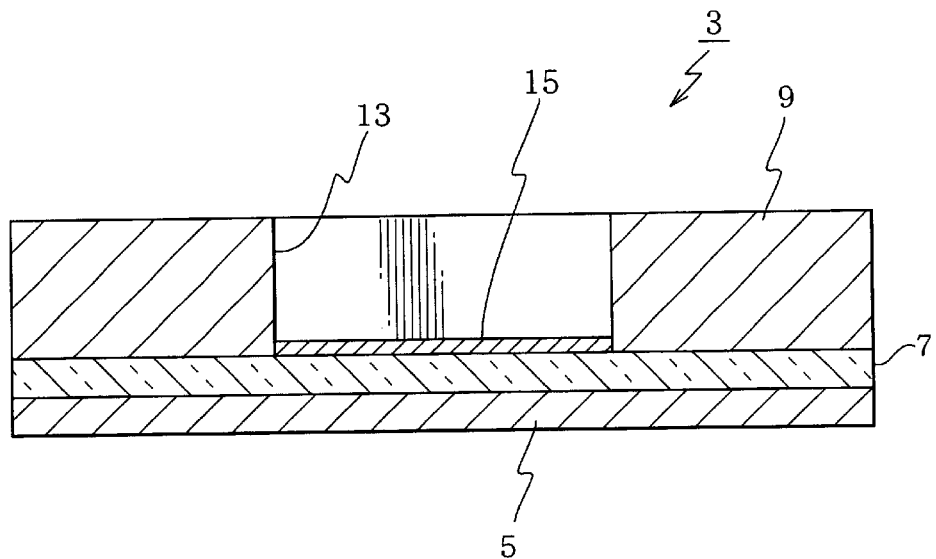
(B)
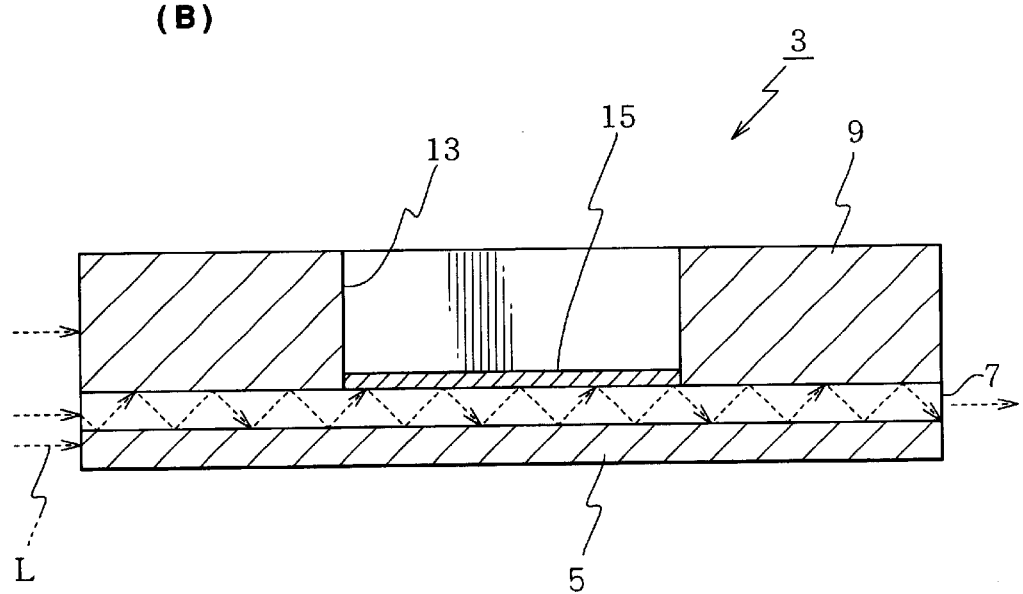
(C)
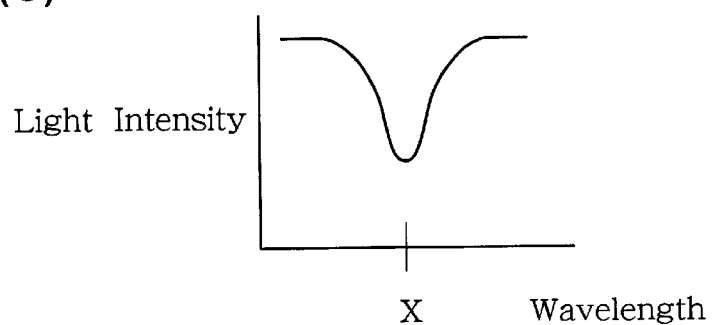

FIG.5
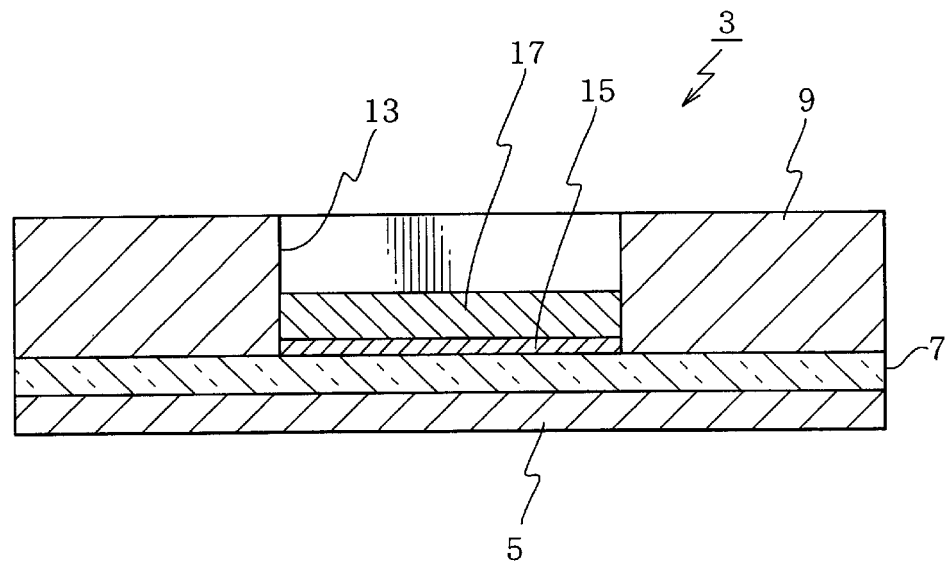
FIG.6
(A)
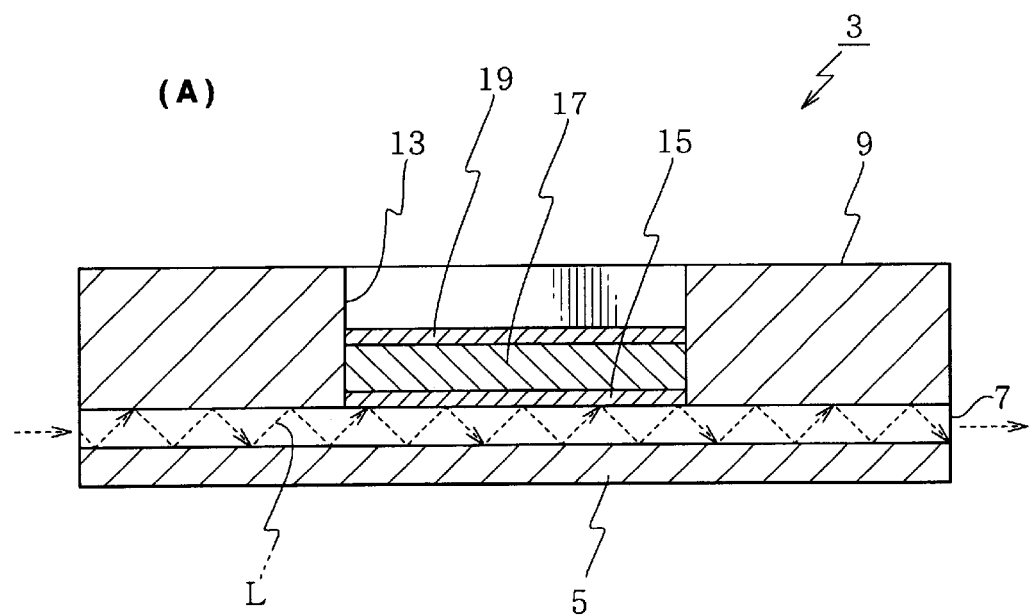
(B)
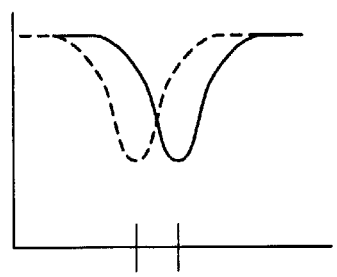
Light Intensity
X Y    Wavelength

FIG.12
(A)
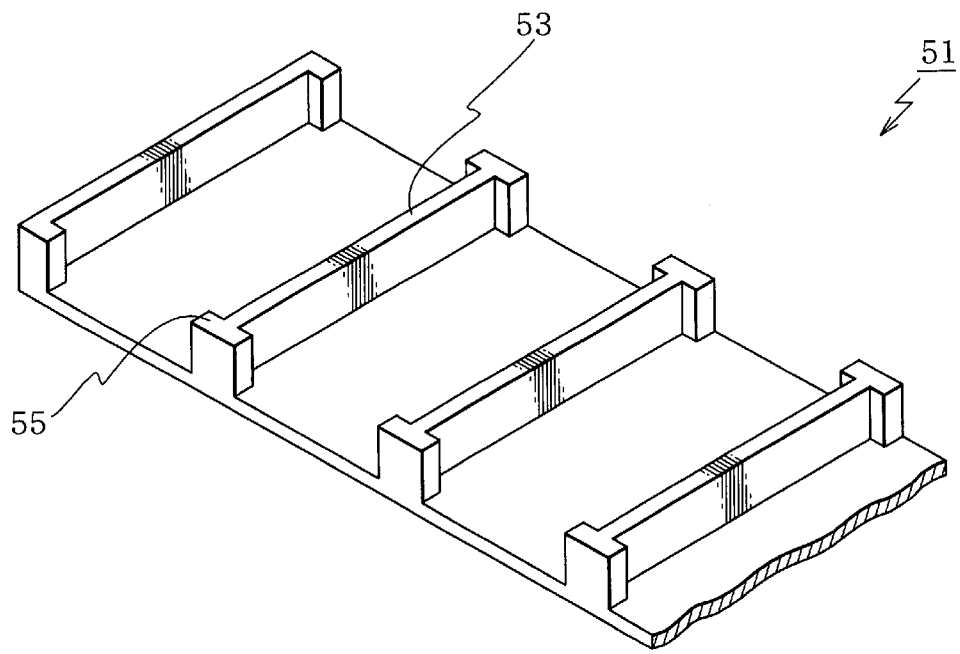
(B)
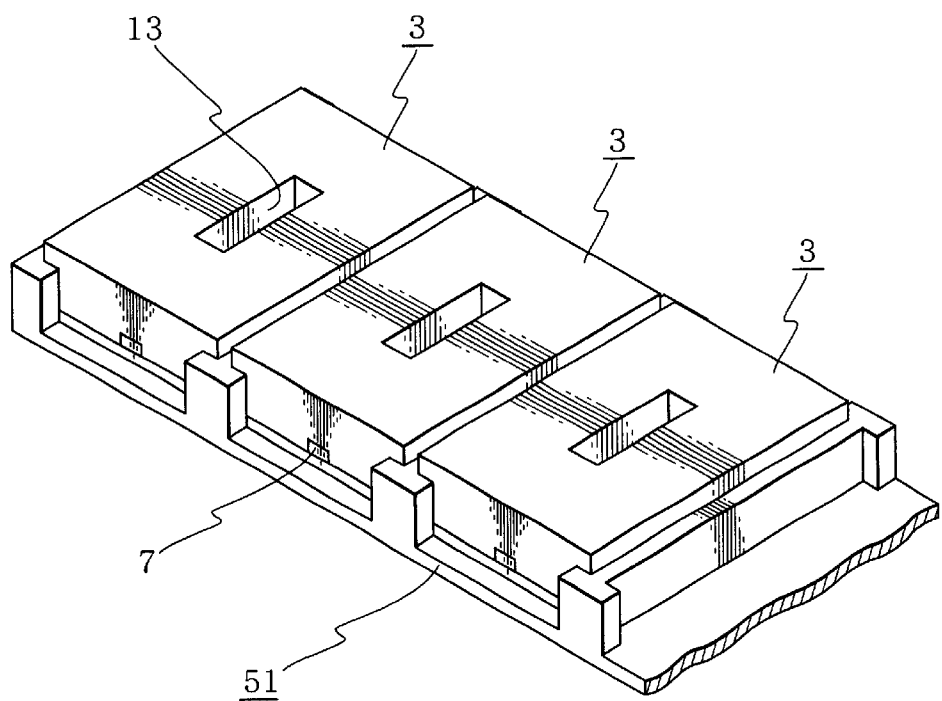

FIG.13
(A)
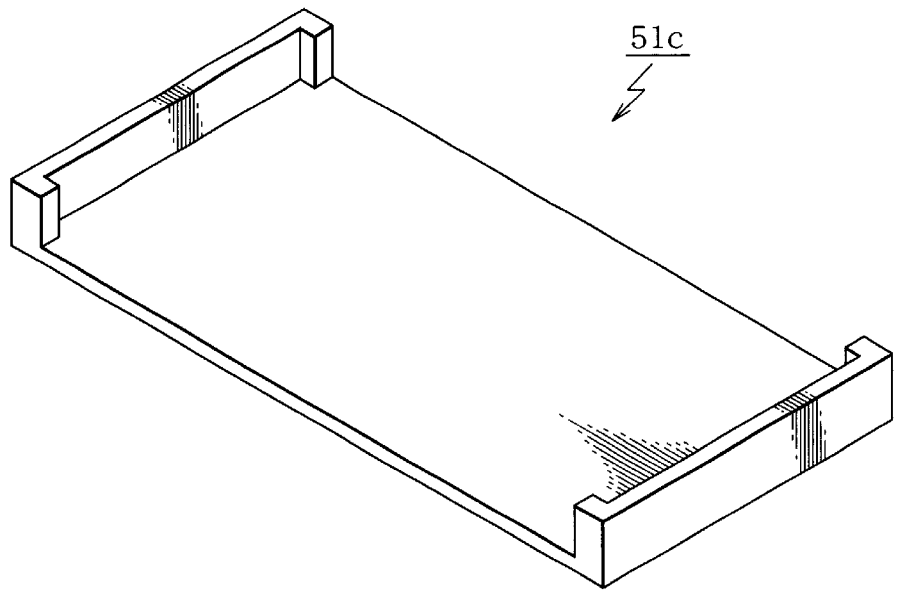
(B)
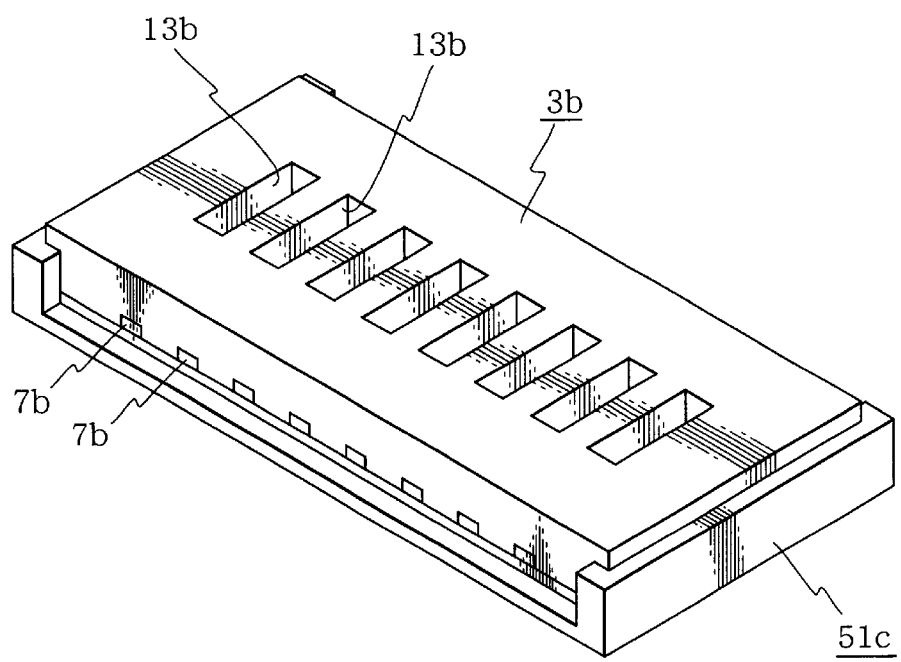

*FIG.15*
(A)
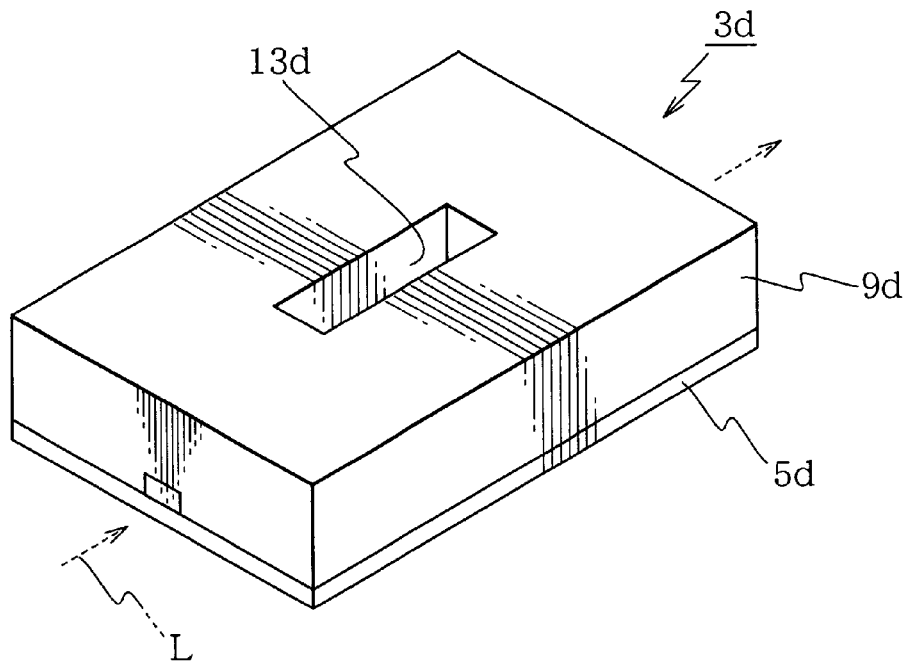
(B)
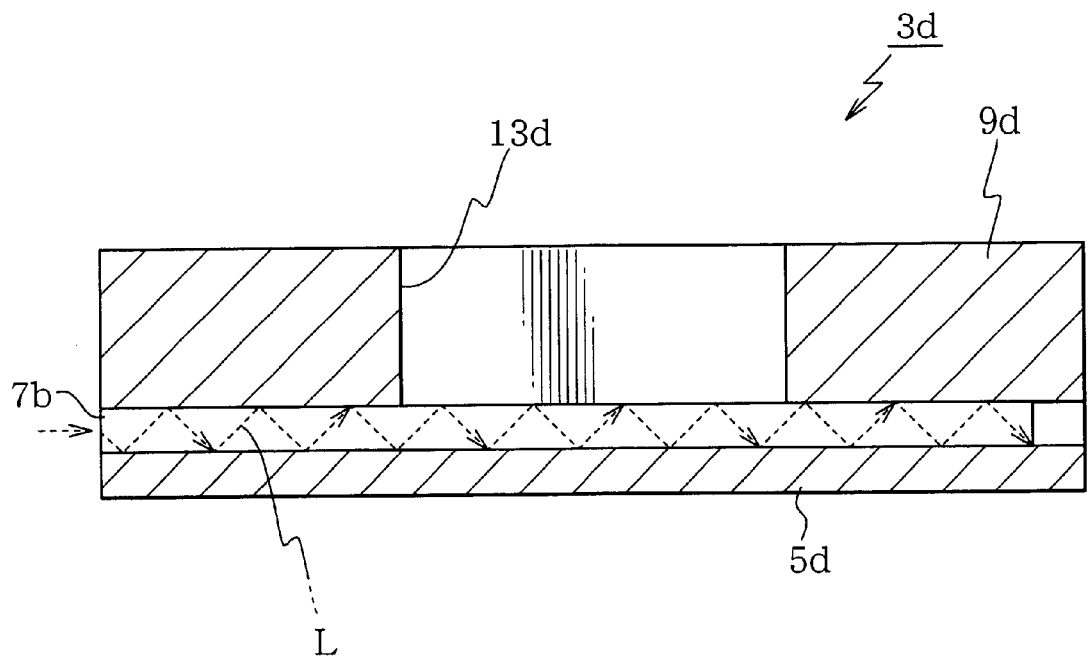

(A)

(B)

FIG.18
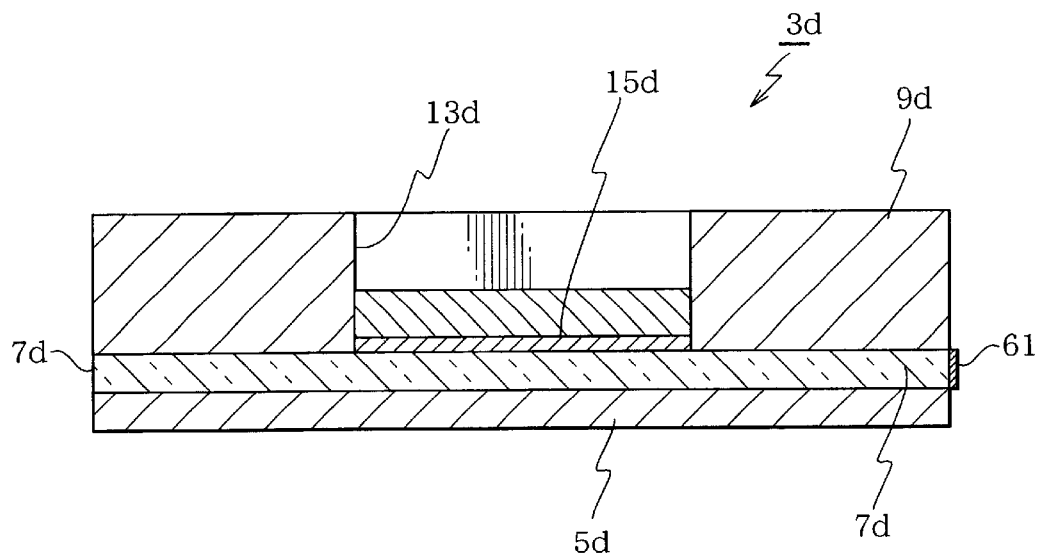
FIG.19
(A)
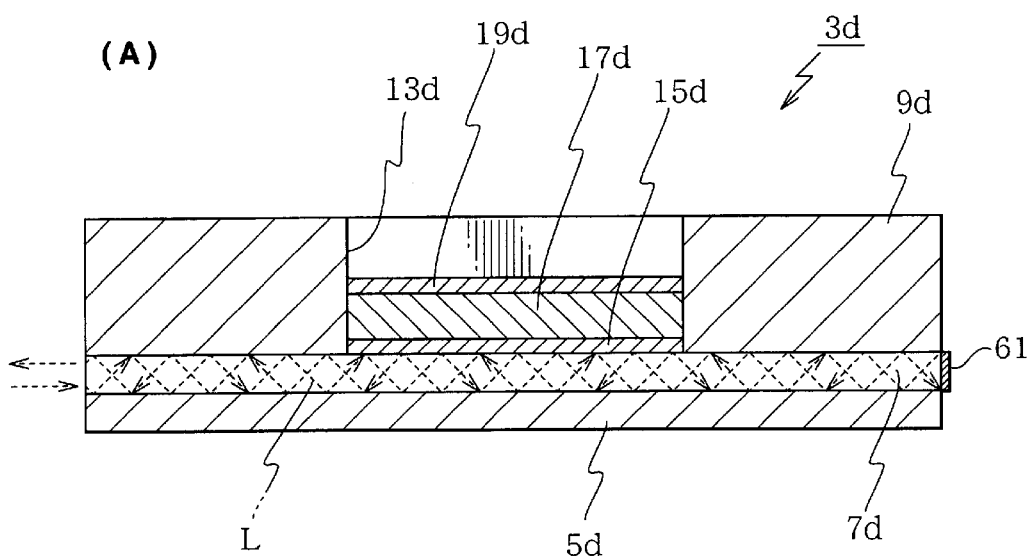
(B)
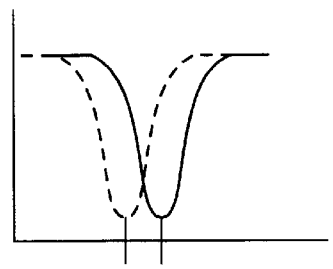
Light Intensity
X Y  Wavelength FIG. 20
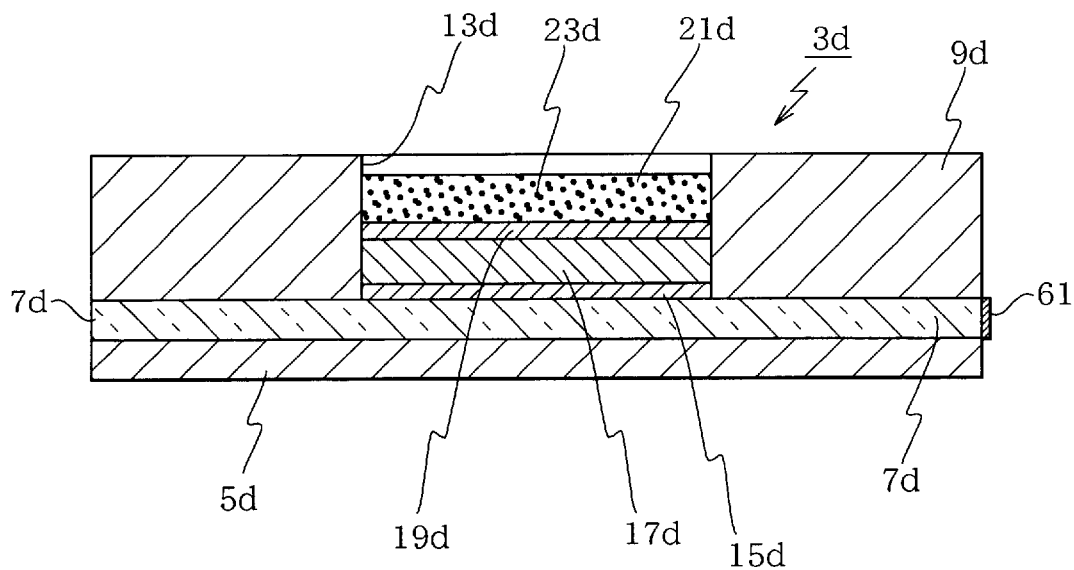
FIG. 21
(A)
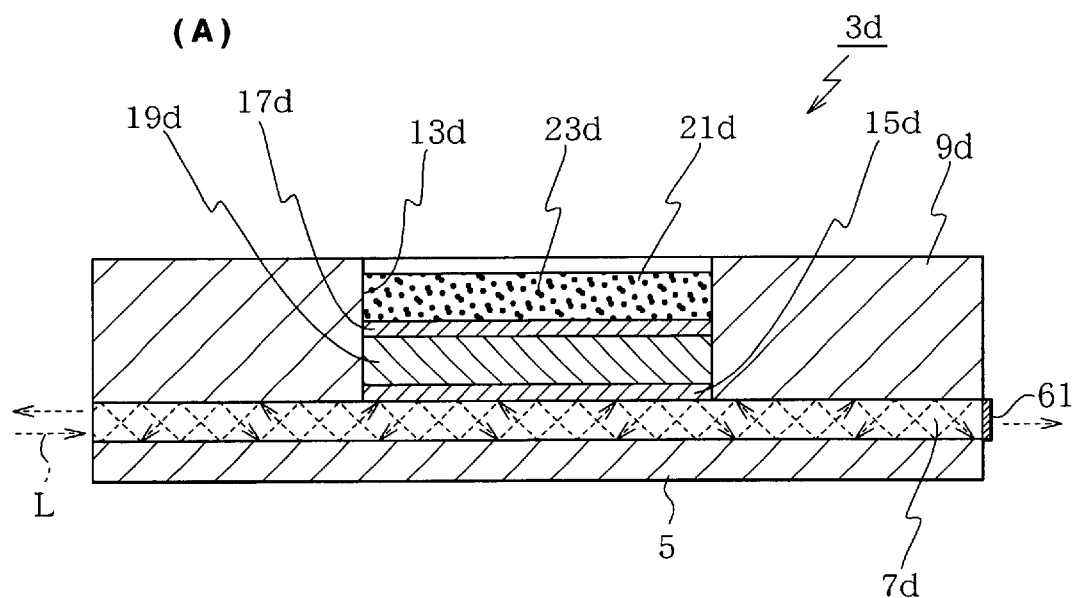
(B)
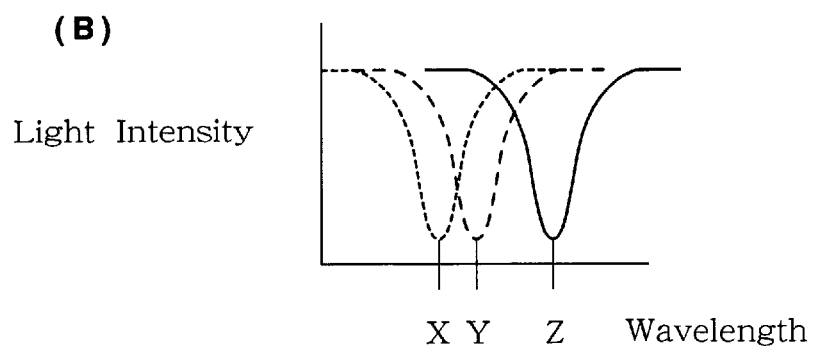

*FIG.22*
(A)
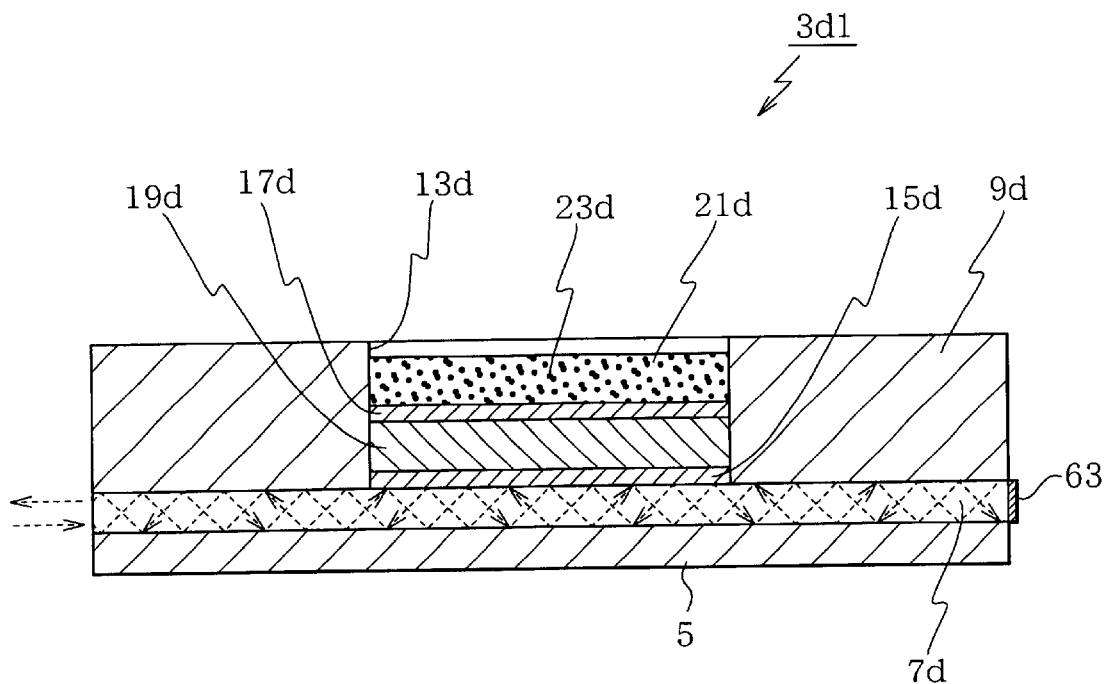
(B)
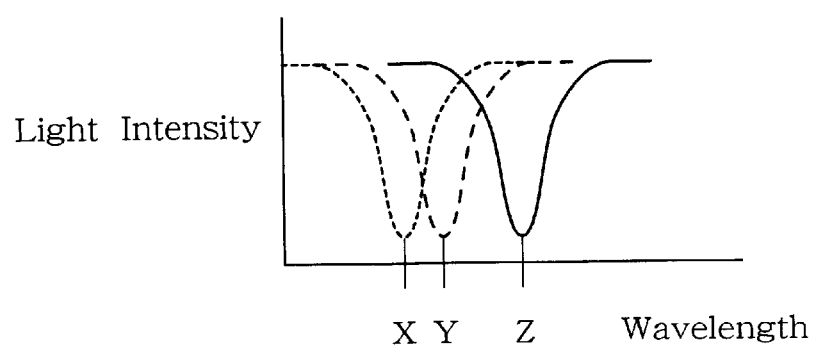

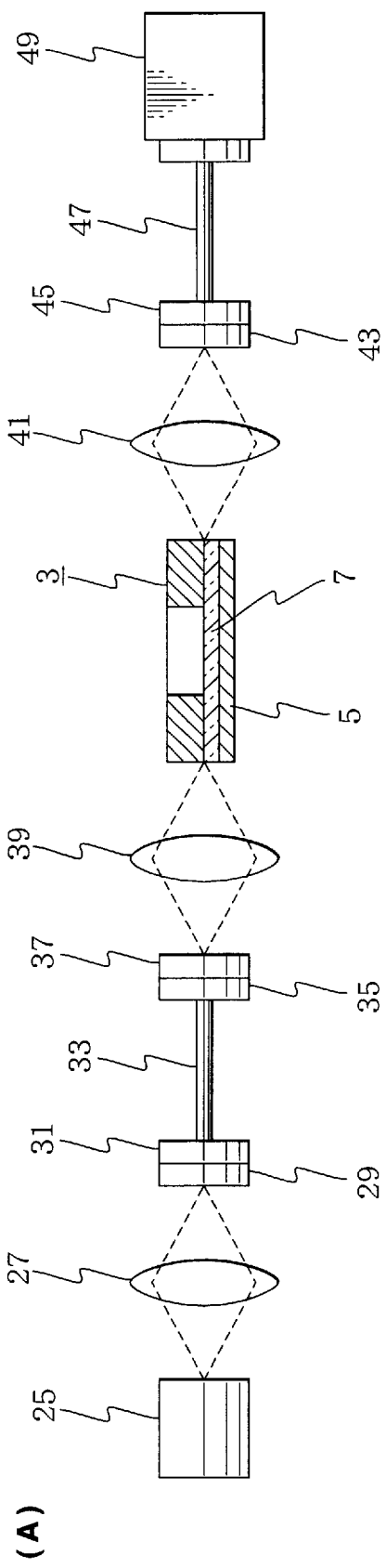
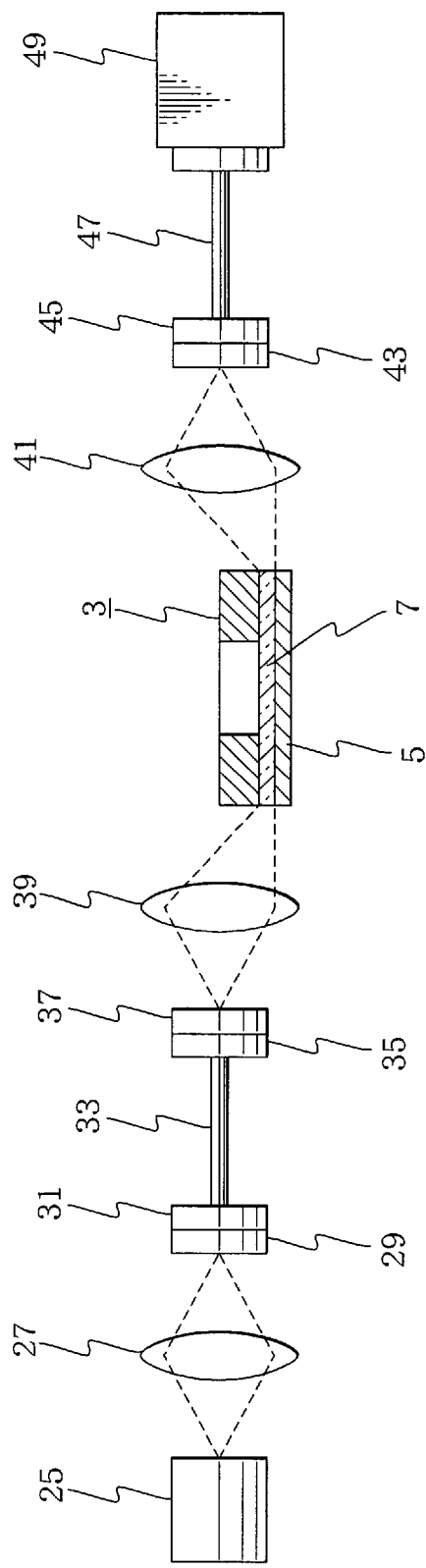
FIG. 25

FIG.26
(A)
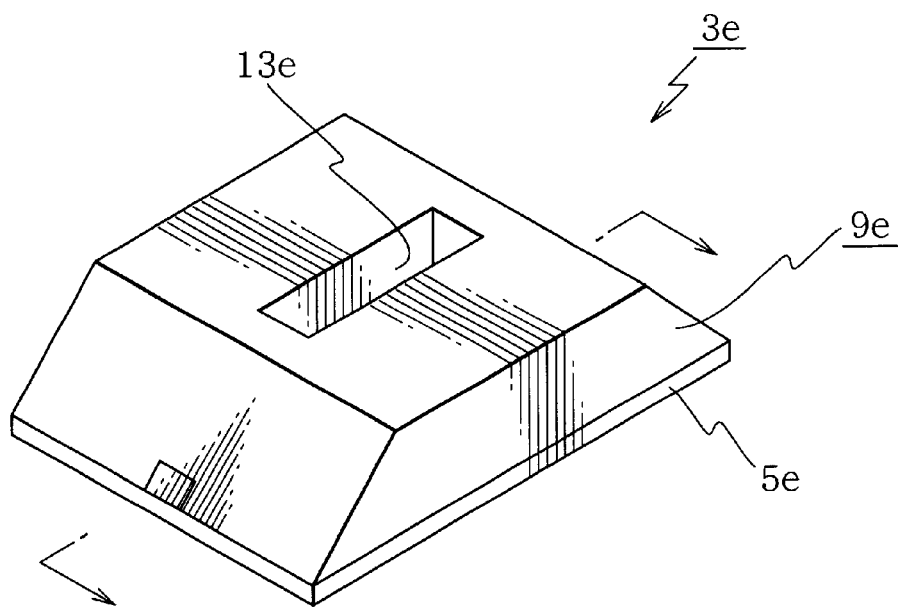
(B)
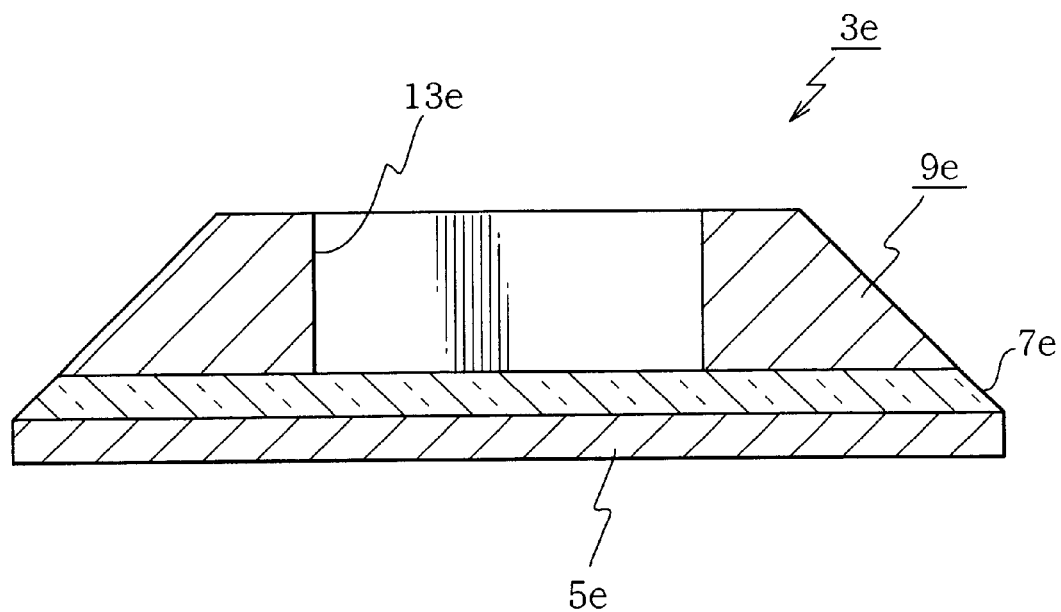

FIG.29
(A)
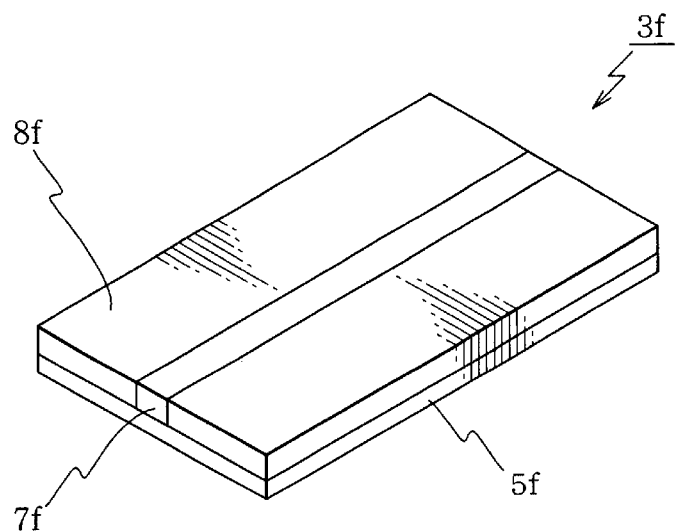
(B)
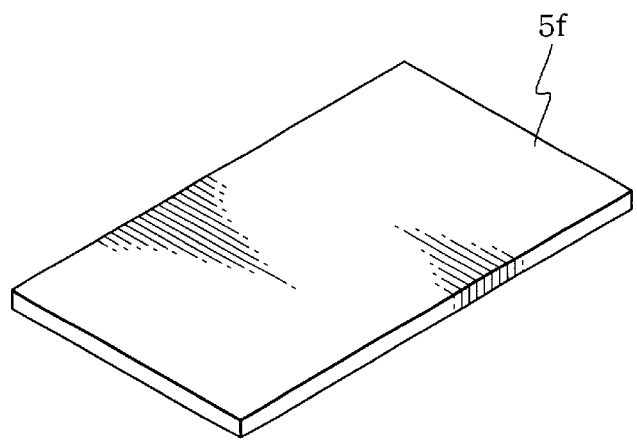
(C)
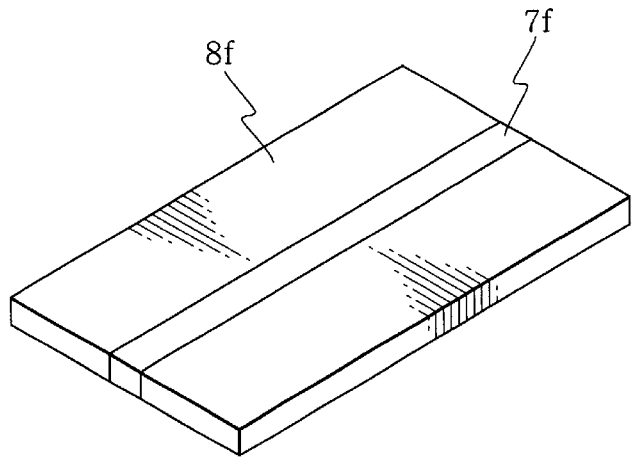

FIG.30
(A)
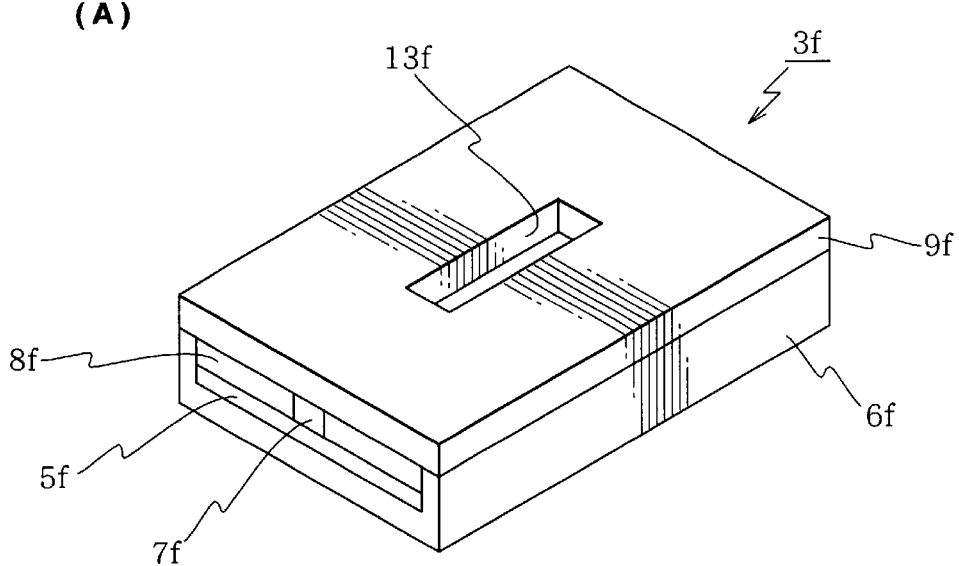
(B)
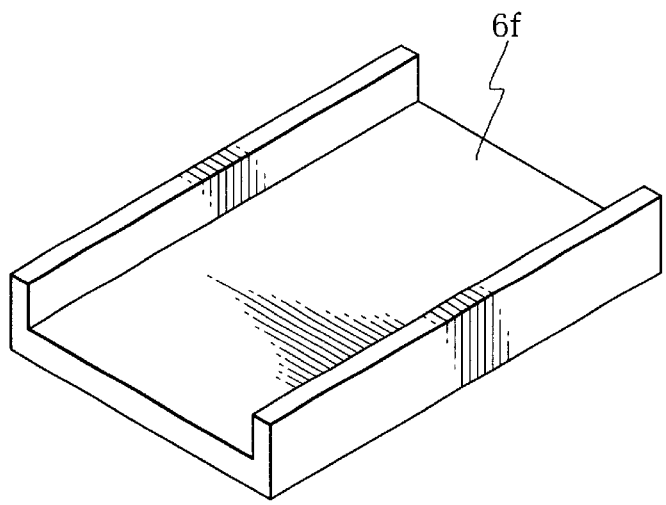
(C)
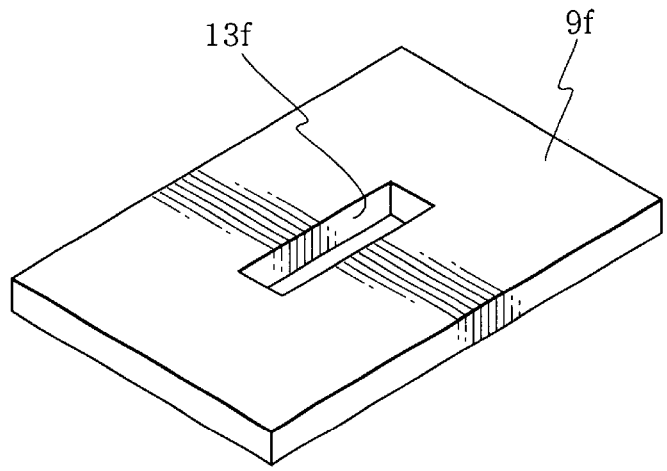

FIG. 31
(A)
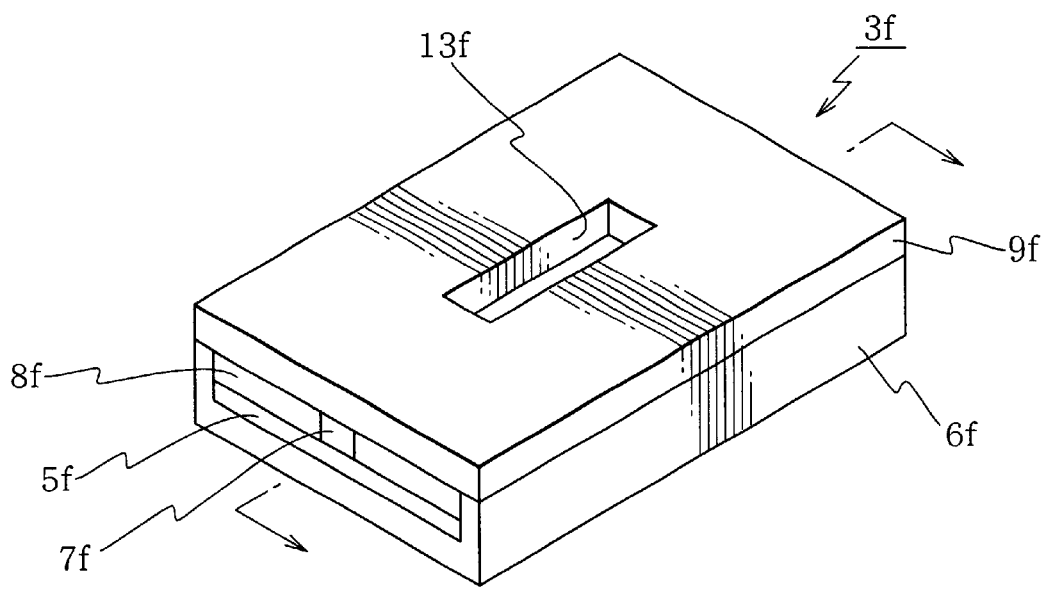
(B)
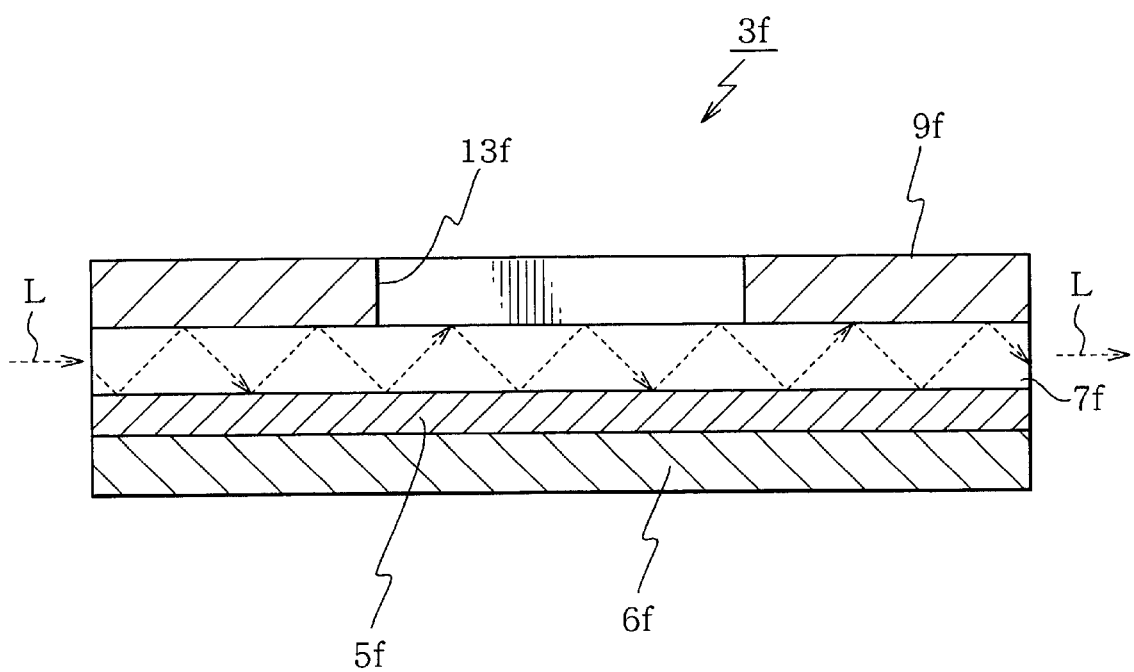

FIG.32
(A)
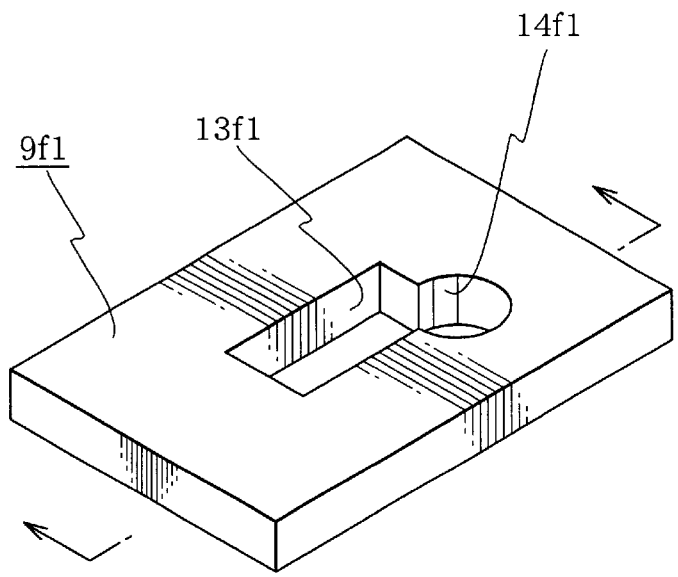
(B)
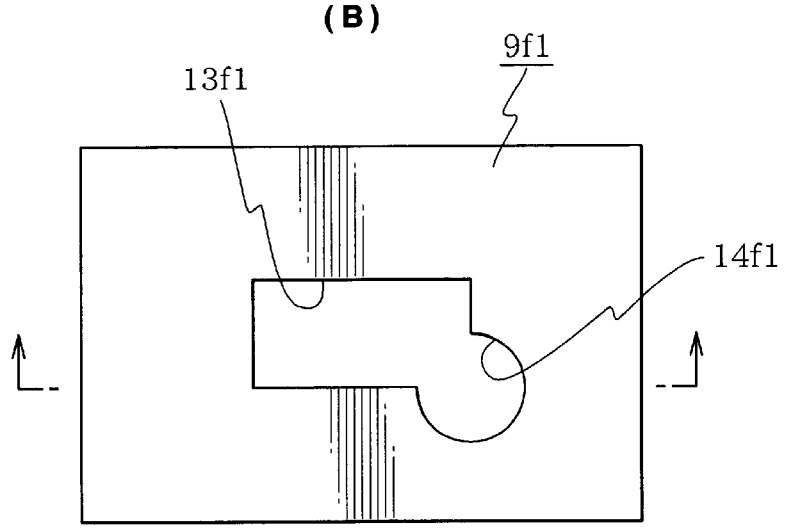
(C)
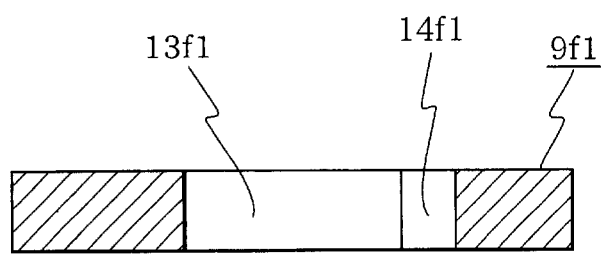

FIG.33
(A)
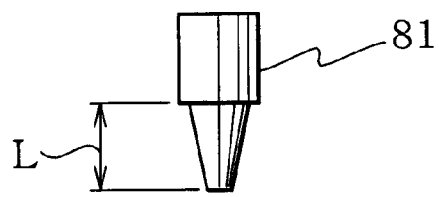
(B)
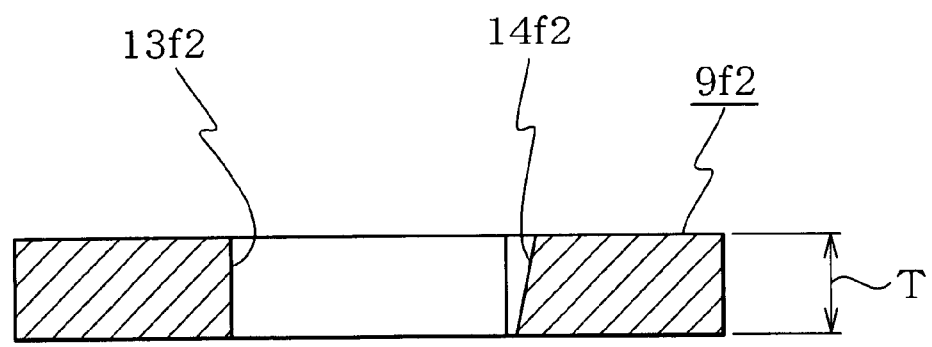

FIG.34
(A)
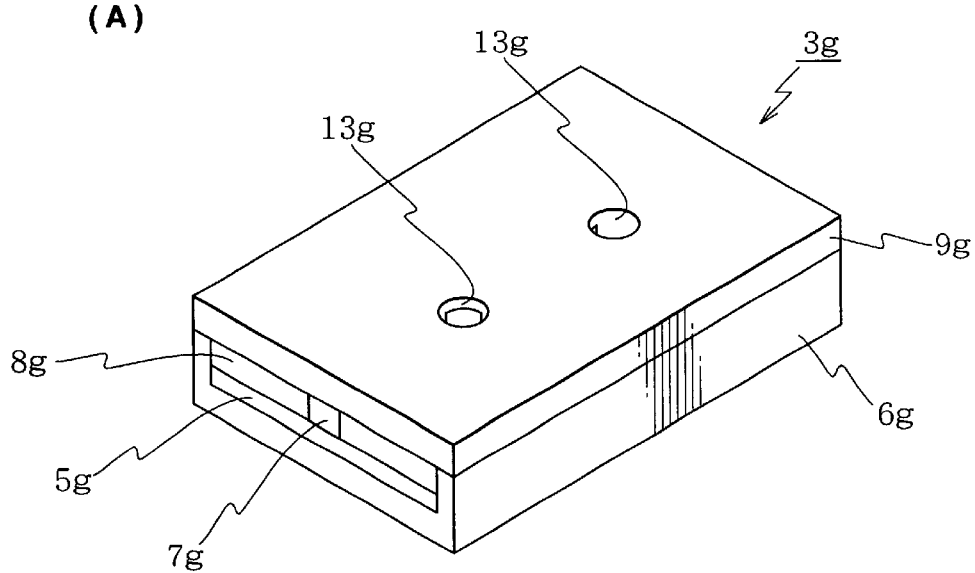
(B)
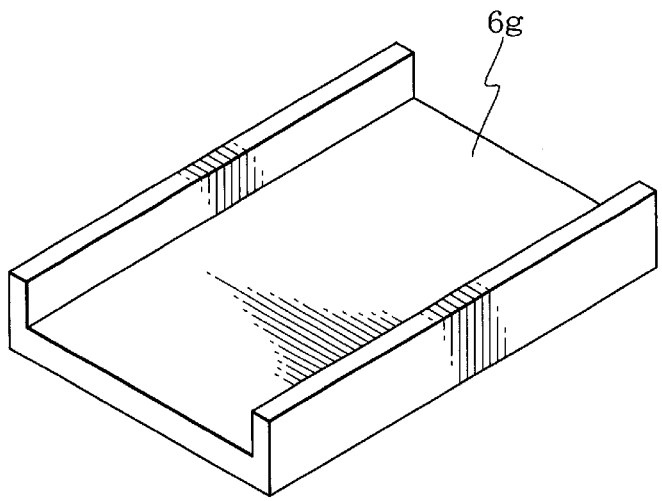
(C)
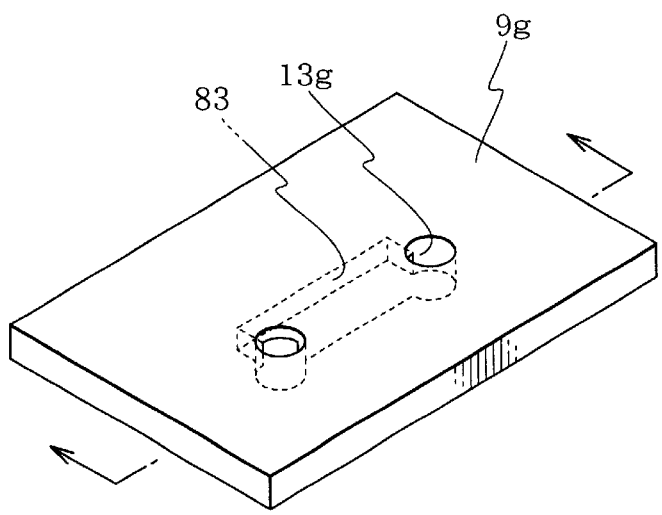

(A)

(B)

FIG. 40
(A)
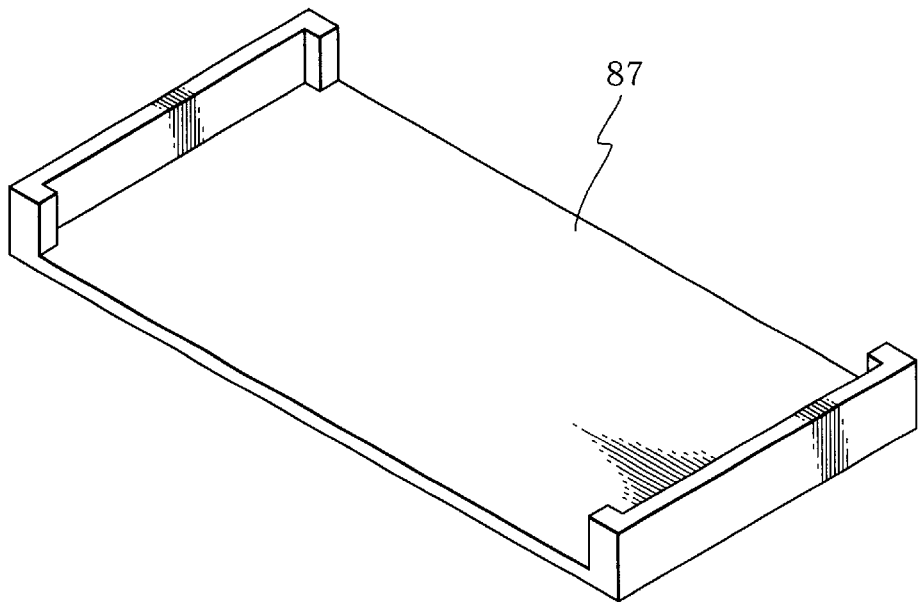
(B)
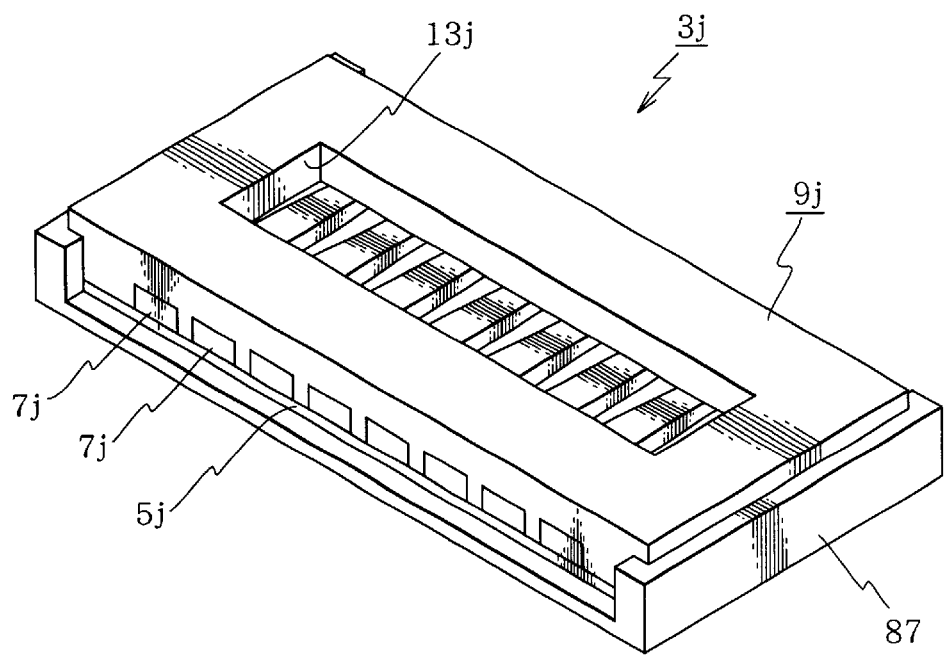

FIG. 41
(A)
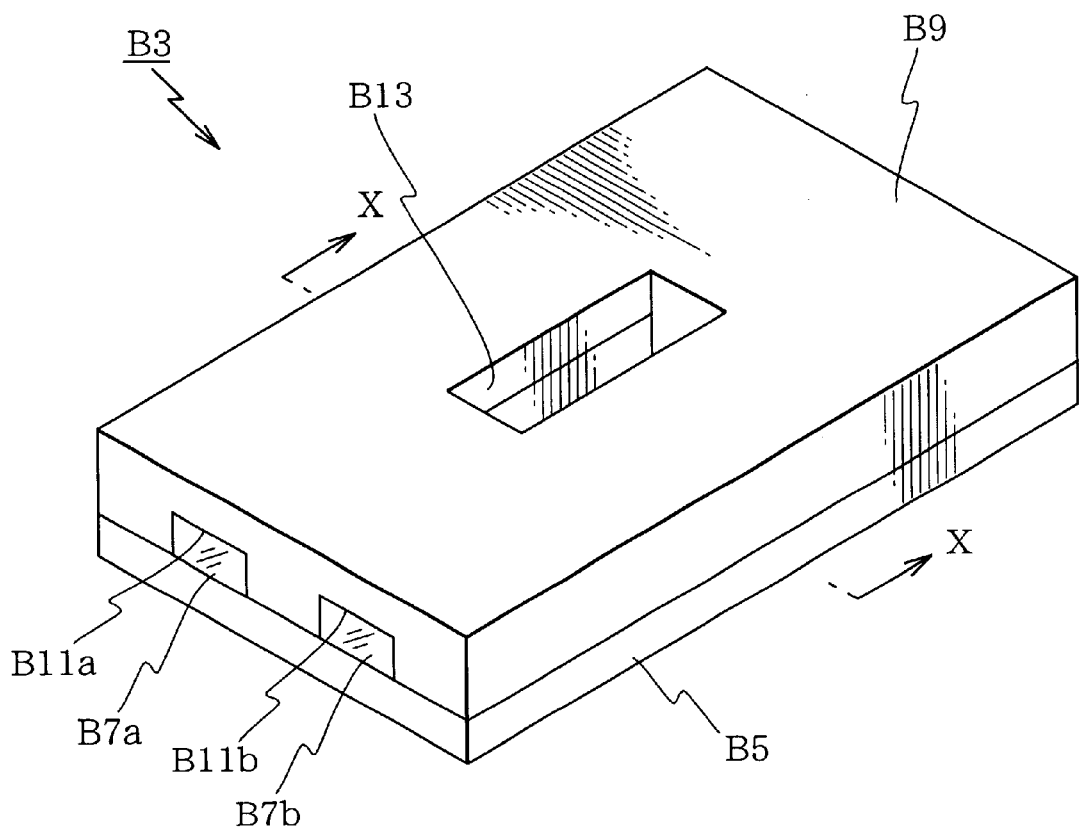
(B)
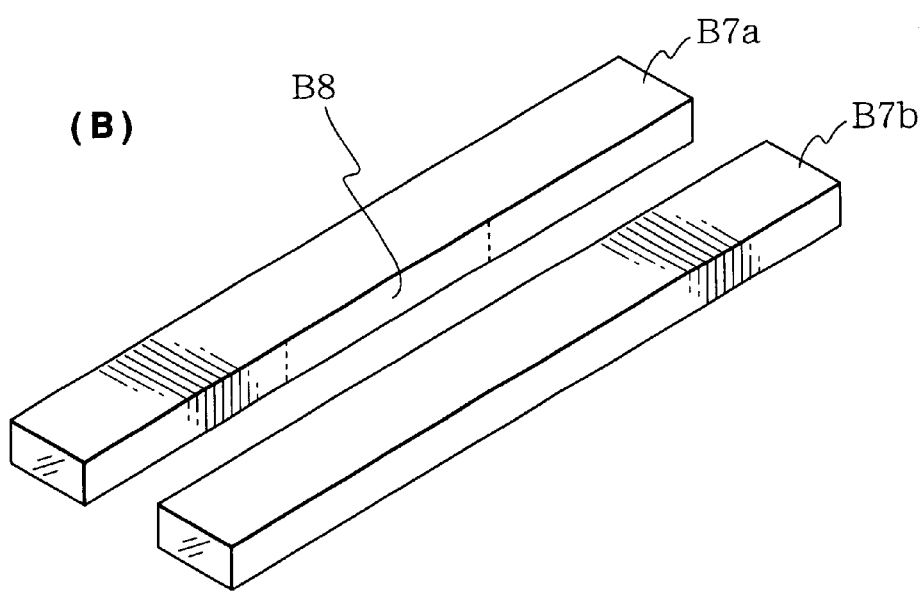

FIG.42
(A)
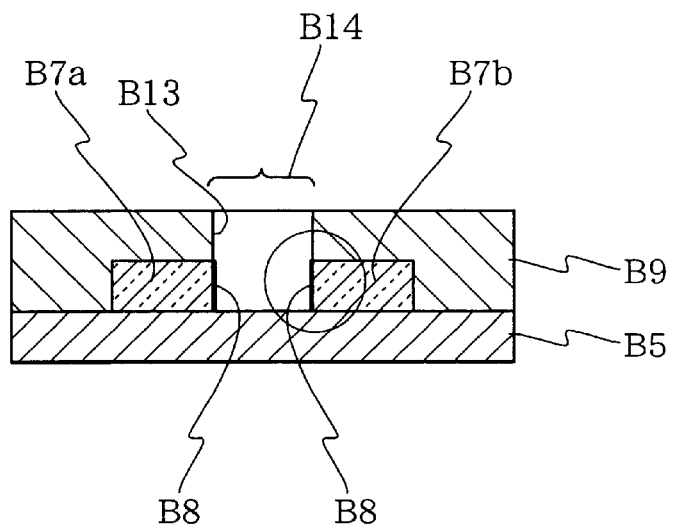
(B)
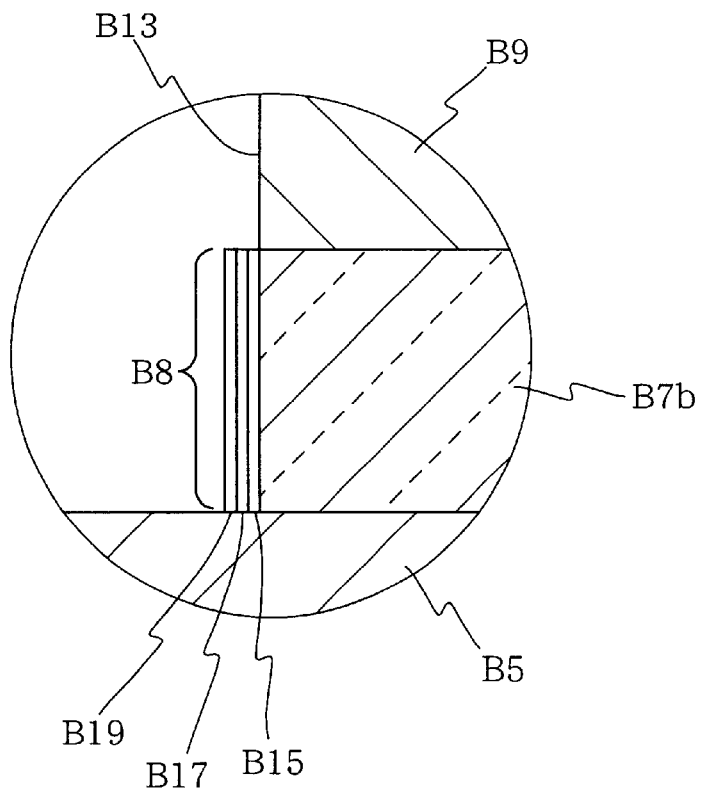

FIG.44
(A)
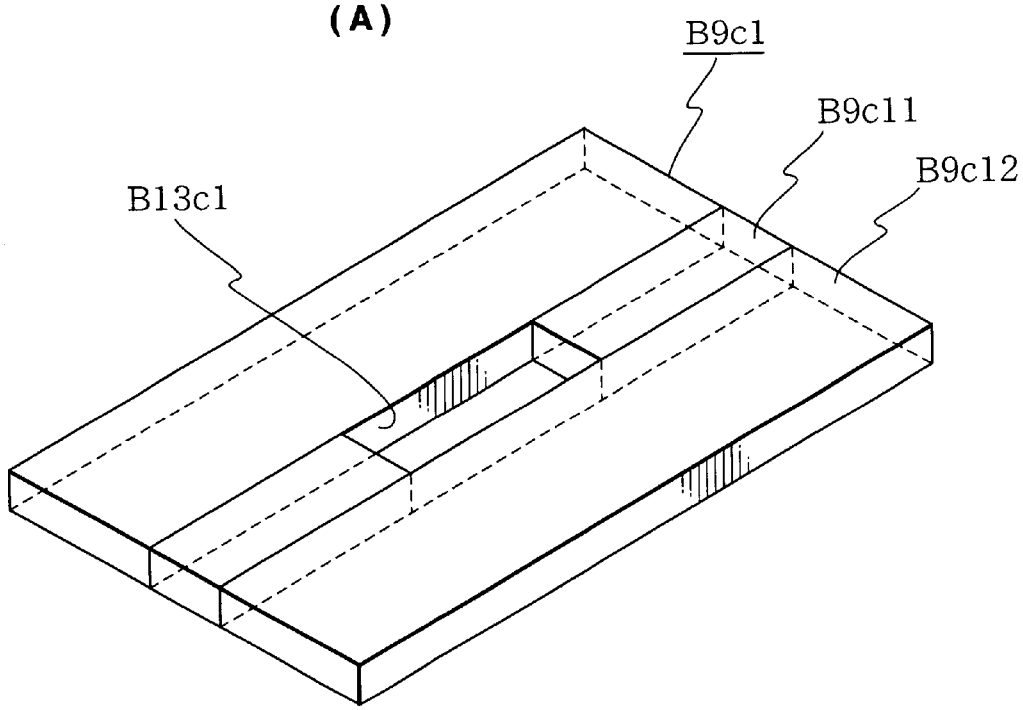
(B)
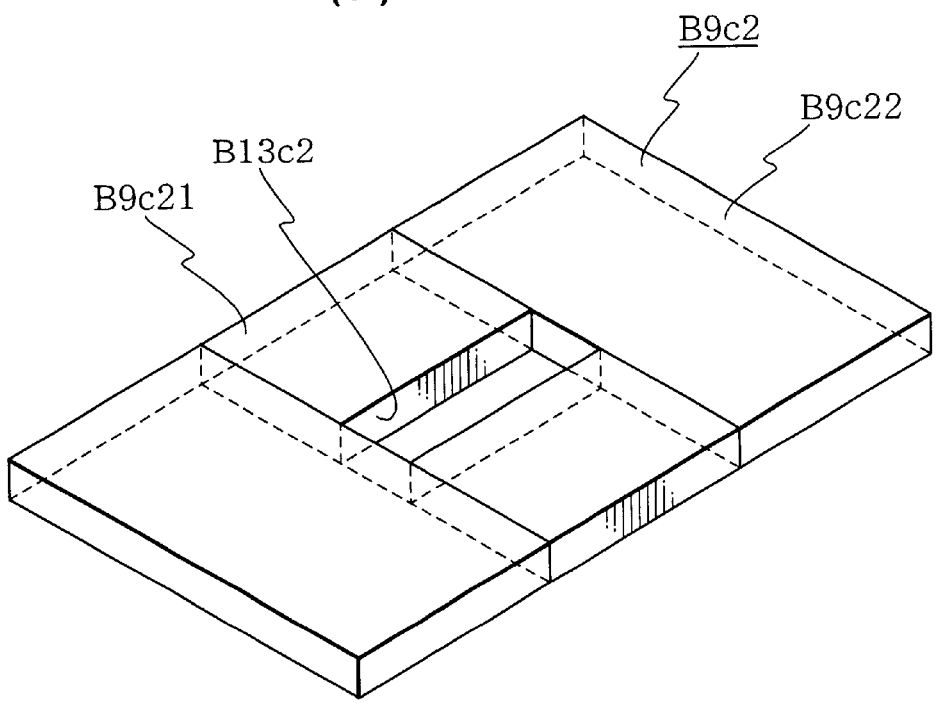

FIG.45
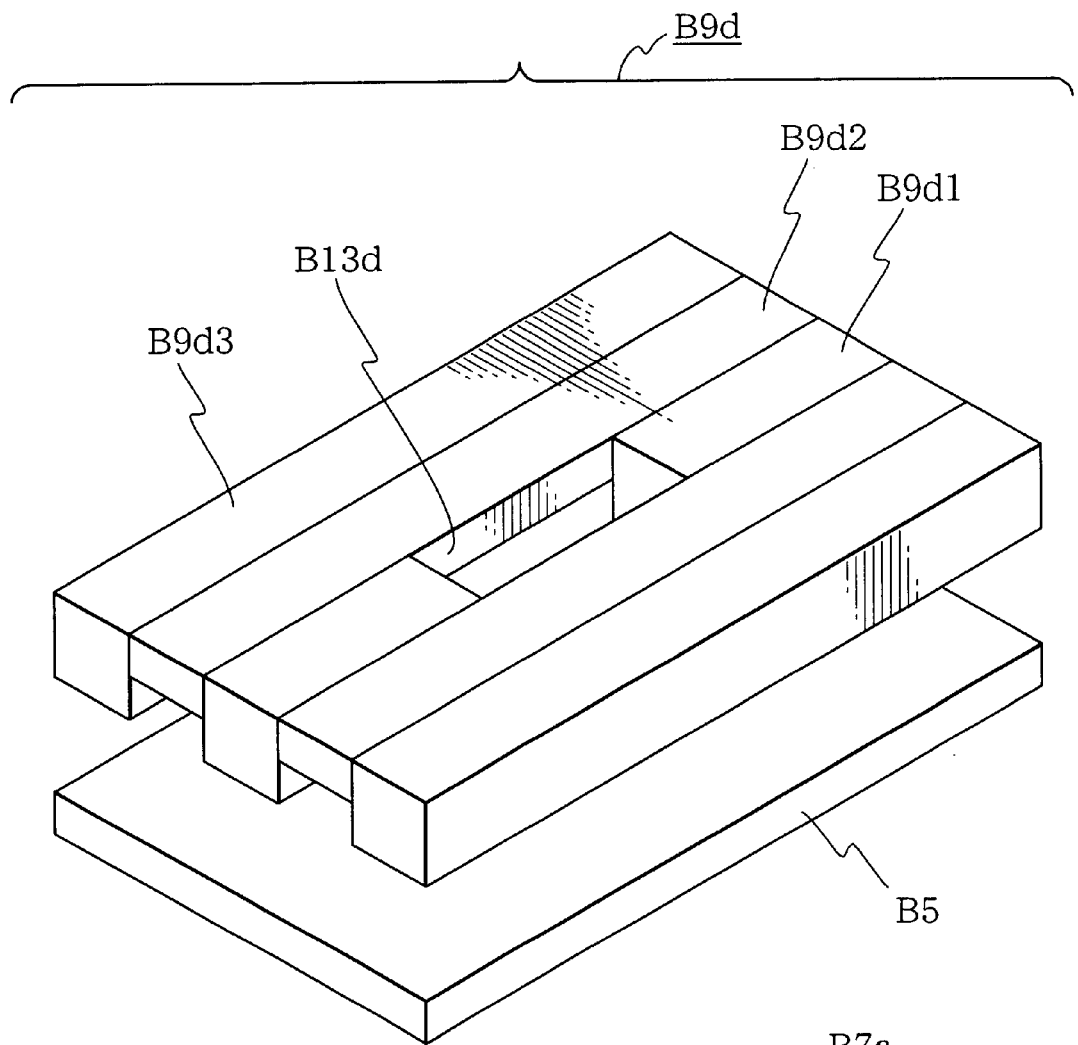
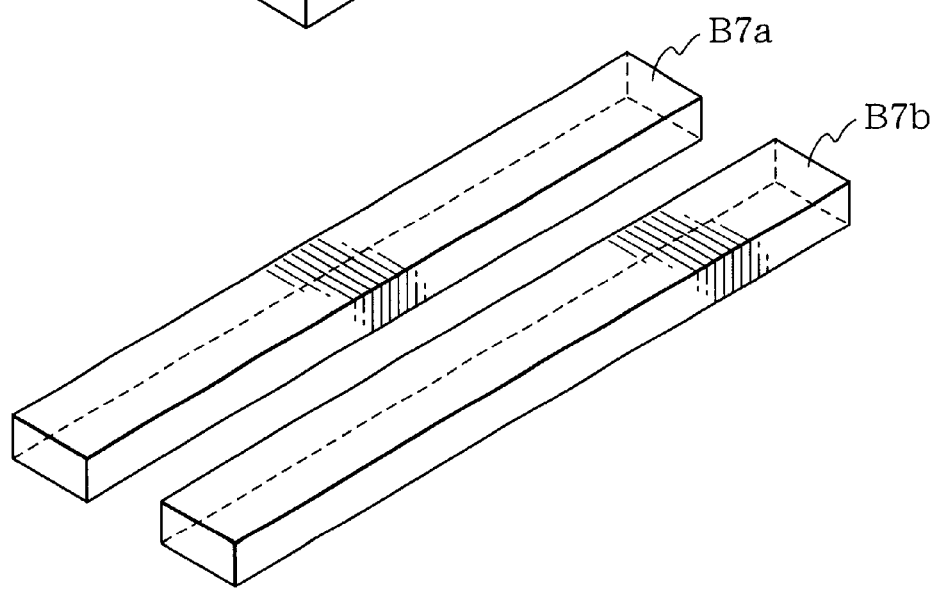

FIG. 51
(A)
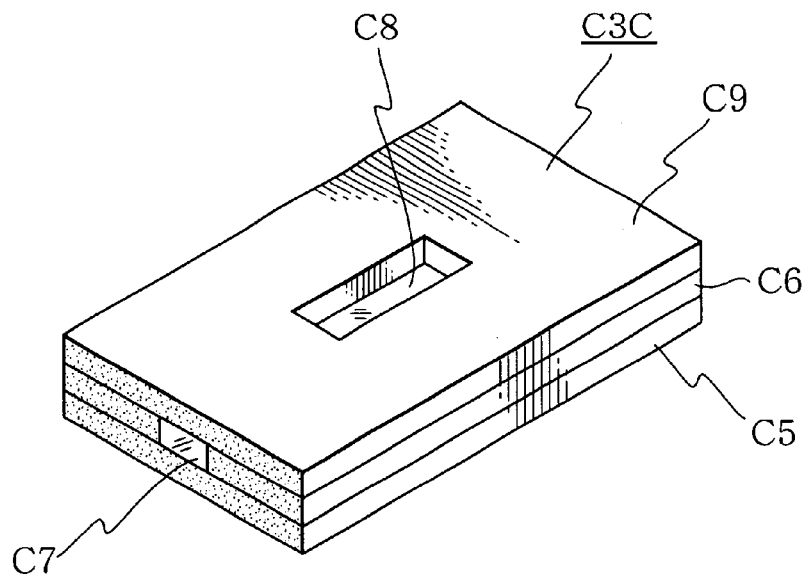
(B)
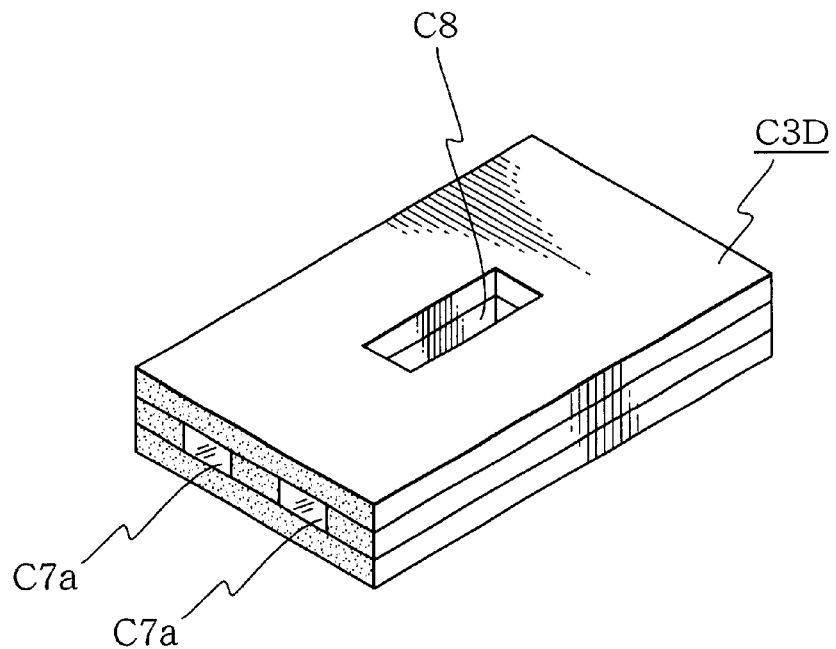

FIG. 61
(A)
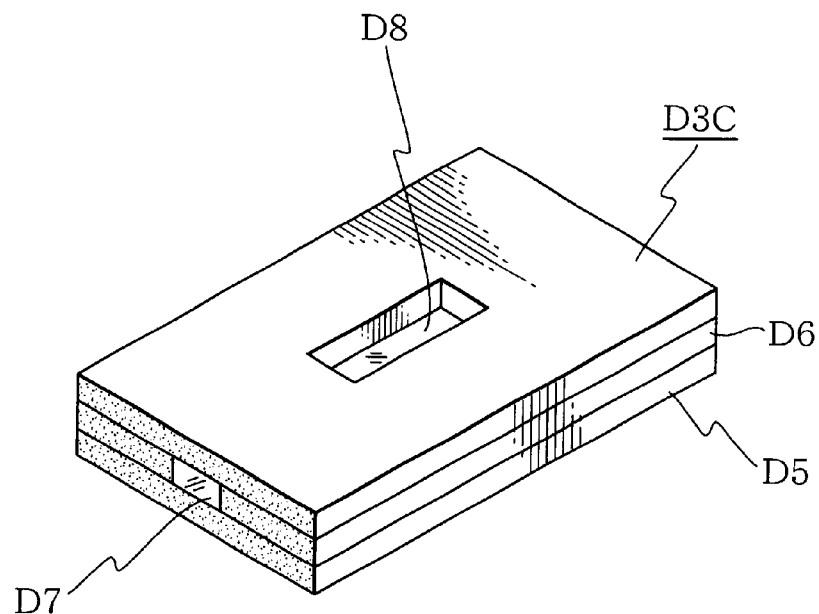
(B)
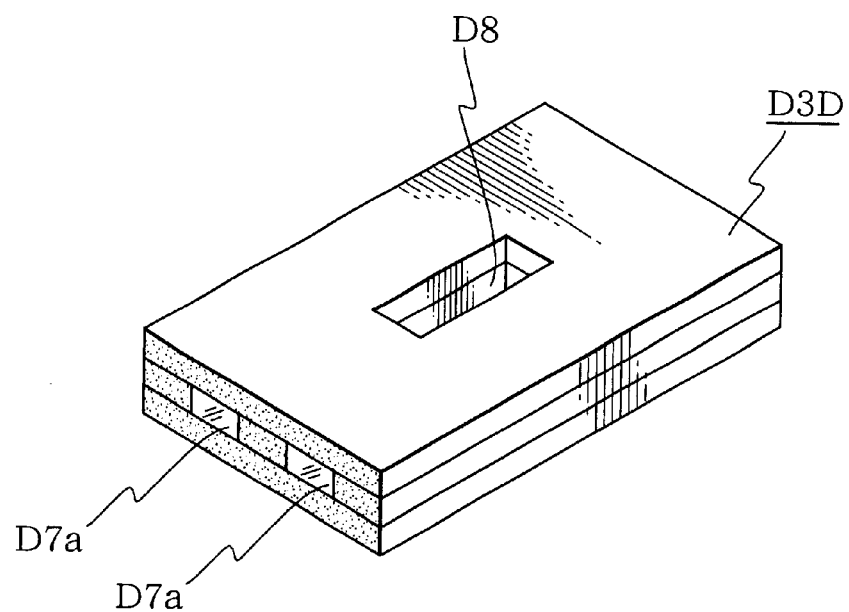

FIG. 68
(A)
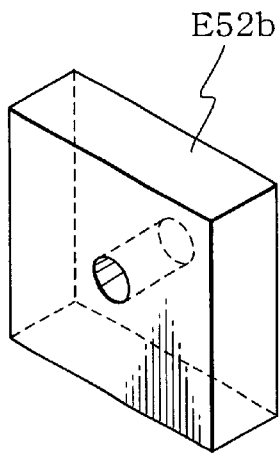
(B)
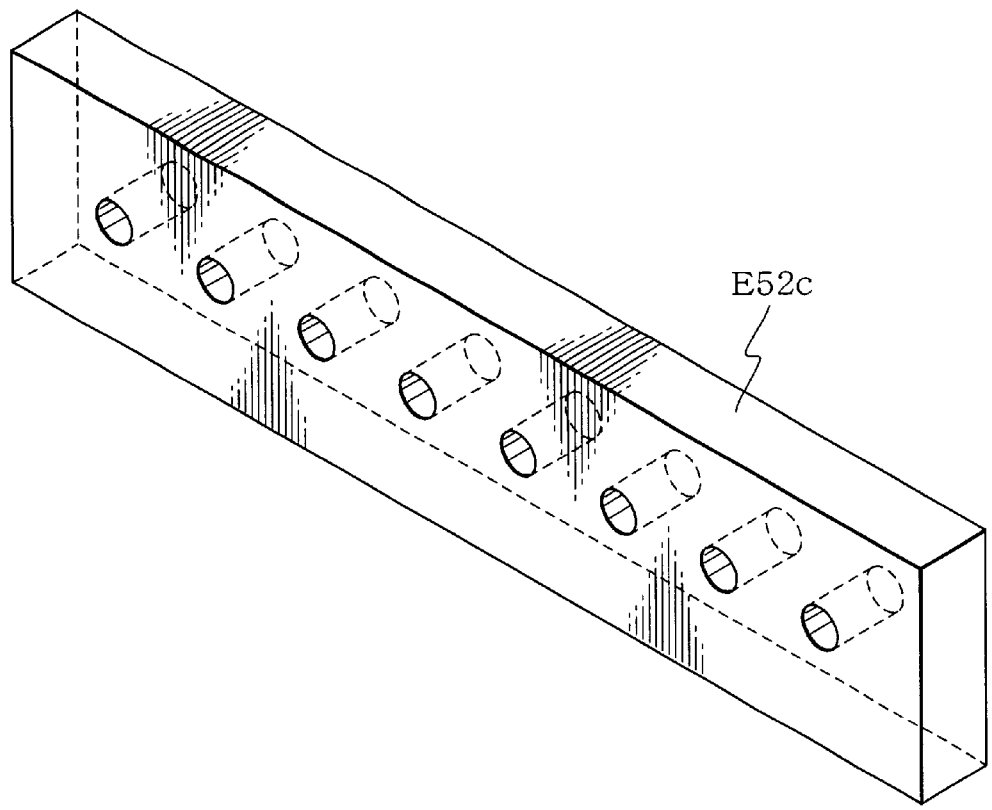

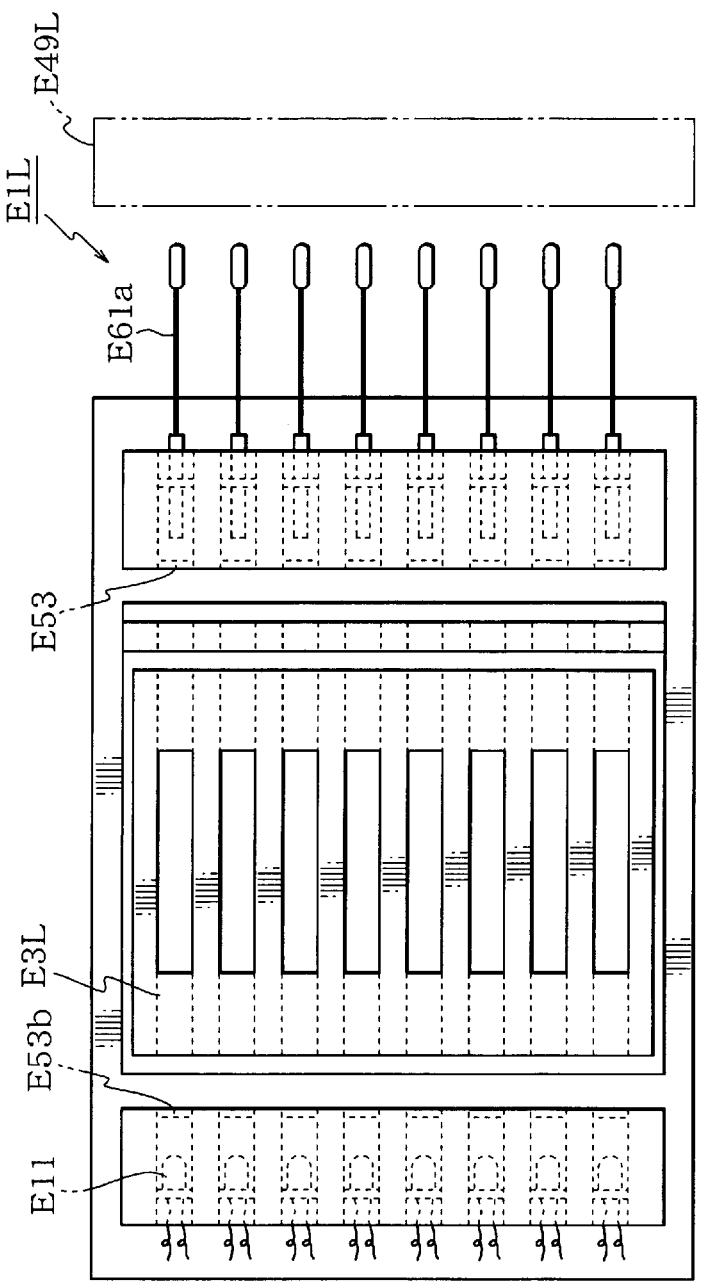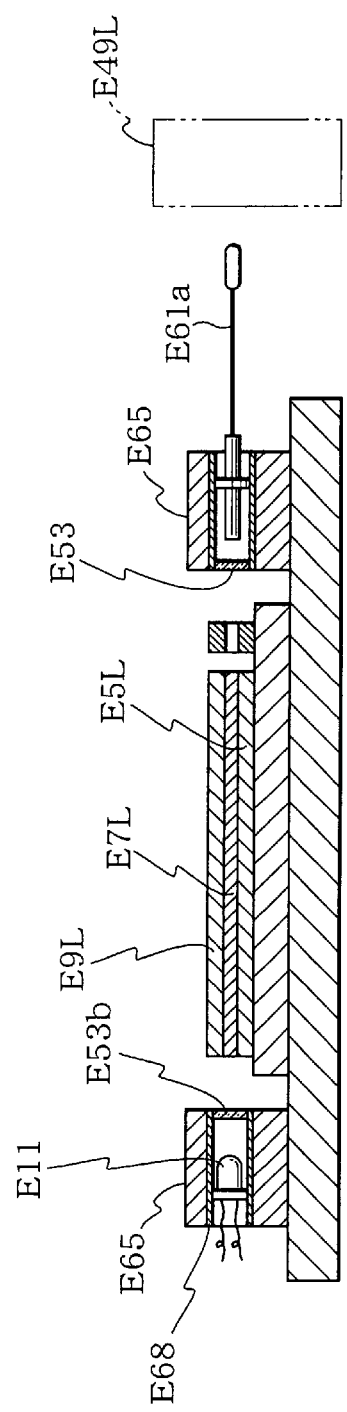
FIG. 88

SPR SENSOR CELL AND IMMUNOASSAY APPARATUS USING THE SAME

BACKGROUND OF THE INVENTION

1. Field of the Invention

The present invention relates to an immunoassay apparatus and in particular, to an SPR sensor cell utilizing a phenomenon of surface plasmon resonance (hereinafter, referred to as SPR) and an immunoassay apparatus using the SPR sensor cell.

2. Description of the Related Art

Conventionally, the immunoassay is generally used for detecting a very small quantity of protein. This immunoassay utilizes a specific immune reaction between an antigen (protein to be detected) and a corresponding antibody (prepared using the antigen) so as to determine the antigen concentration in a sample. This immunoassay can determine an antigen even in a sample having a plurality of antigens without isolating the target antigen, unlike a chemical or physical quantity determination.

Moreover, various types of immunoassay are available:
1) radio immunoassay (RIA)
2) enzyme immunoassay (EIA)
3) fluoro immunoassay (FIA)

The RIA (radio immunoassay) needs to use an isotope and is not widely used recently. Moreover, the EIA (enzyme immunoassay) is widely used currently because the EIA can easily determine an immune reaction. Furthermore, the FIA (fluoro immunoassay) can determine a quantity with a higher sensitivity and a higher accuracy.

The EIA method which uses a solid phase for determining a quantity of an antibody is called enzyme-linked immunosorbent assay (ELISA). There are two types of ELISA:
   a) indirect method using an antigen in a solid phase; and
   b) antibody catching method using anti-IgG antibody in a solid phase.

The ELISA method is used for determining a quantity of antibody for a specific causal organism; determining a quantity of antibody for an allergen; and for screening of a monochronal antibody.

For the ELISA, an assay kit includes a micro-plate having 96 wells on which an immune reaction is determined. Accordingly, it is possible to determine quantities of a multiple samples at once. Recently, various types of the automated ELISA are available on market.

As for the ELISA kit, various chemicals are produced by various companies. For example, tPA is an enzyme which indirectly serves to dissolve fibrin in blood associated with a blood clotting and thrombus. Moreover, PAI-1 suppresses the tPA and serves to make a blood clotting and thrombus.

On the other hand, the so-called SPR sensor is known as a sensor used in an immunoassay apparatus. The SPR sensor is sensor utilizing the surface plasmon resonance phenomenon as follows.

That is, a thin metal film of about 50 nm thickness is deposited onto a bottom of a prism having a high refraction factor. Then, a predetermined light is introduced with an angle greater than a critical angle from the prism to the thin metal film. The thin metal film of 50 nm thickness is semi-transparent. The light incident from the prism passes through the thin metal film to reach a surface of the thin metal film at the opposite side of the prism, generating an evanescent field on the surface of the thin metal film.

By adjusting the light incident angle, the number of waves of the evanescent field is matched with the number of waves of surface plasmon resonance so as to excite a surface plasmon resonance on the thin metal film. In this case, the number of waves of the surface plasmon resonance depends on the dielectric ratio of the thin metal film and a refraction factor of a sample fixed to be in contact with a surface of the prism having the thin metal film. Thus, it is possible to check the refraction factor and a dielectric ratio of the sample. That is, when the optical system and the sample are located at opposite positions sandwiching the thin metal film, it is easy to constitute a sensor.

In connection with the aforementioned principle, there has been developed an SPR sensor for an immunoassay apparatus using an optical fiber (trade name: BIACORE Probe produced by the BIACORE CO., Ltd.). This SPR sensor using an optical fiber is produced as follows. Firstly, a clad is removed from the end of the optical fiber and the optical fiber end surface, i.e., the core end surface is accurately cut or polished and this end surface is coated with silver. Moreover, the exposed core portion after removing the clad is covered with a thin metal film (gold or silver). Furthermore, he thin metal film is covered with a dielectric film, onto which an antibody used for the immunoassay is fixed. Moreover, at the other end of the optical fiber, a predetermined light source is provided so as to introduce a light into the optical fiber.

Description will now be directed to the immunoassay technique using the SPR sensor having the aforementioned configuration.

Firstly, the light from the light source is introduced into the optical fiber and a light of specific wavelength excites a surface plasmon resonance at the end of the optical fiber. The wavelength causing the surface plasmon resonance is changed by the refraction factor between the dielectric film and the antigen. The light of the wavelength which has caused the surface plasmon resonance is attenuated. Thus, the immunoassay can be performed by comparing the light wavelength attenuated most prior to the immune reaction and the light wavelength attenuated most after the immune reaction.

In addition to the SPR sensor using the optical fiber, there has been developed an SPR sensor using a prism.

However, the aforementioned conventional sensors have various problems and disadvantages. When an SPR sensor is constituted by using an optical fiber, it is necessary to cover the optical fiber core end portion with a thin metal film (for example, Au deposition). However, the optical fiber itself is a very small component and it is not easy to form a thin metal film appropriately.

Moreover, when performing an immunoassay actually, an antibody should be fixed onto the surface of the thin metal film. However, the optical fiber core has a cylindrical shape and it is not easy to fix the antibody.

Moreover, in the immunoassay apparatus using a conventional SPR sensor, there is provided only one SPR sensor having a single optical fiber. This brings about various problems. When using the enzyme immunoassay (EIA), a number of measurement steps are required and a long time is required for the immune reaction. That is, a measurement of one sample requires several hours or several tens of hours, and it is impossible to increase the measurement efficiency.

Moreover, in the immunoassay apparatus using the SPR sensor having an optical fiber, an antibody to be used for an immune reaction is fixed to the end portion of the optical fiber so that an antigen to be assayed in the sample is subjected to a reaction with the antibody of the SPR sensor. That is, if a sample contains a number of antigens to be assayed, the antigens should be assayed successively one after another. Moreover, in the conventional immunoassay apparatus, when changing the measurement item, the entire optical fiber is should be replaced with another optical fiber.

SUMMARY OF THE INVENTION

It is therefore an object of the present invention to provide an SPR (surface plasmon resonance) sensor cell enabling to easily fix and maintain an antibody. The present invention also provides an immunoassay apparatus capable of performing an immunoassay quickly.

The SPR sensor cell according to the present invention comprises: a core transparent for a light; a clad covering the core and having a through hole at a predetermined position to communicate with the core; and a predetermined thin metal film formed on an exposed surface of the core corresponding to the through hole.

When performing an immunoassay, firstly, an antibody is fixed via a dielectric film on the thin metal film formed on the SPR sensor cell. Next, light is introduced into the SPR sensor cell so as to identify a wavelength of the light whose intensity is attenuated. After this, a the through hole is filled with a sample for immunoassay so as to obtain an immune reaction. Again, light is introduced into the SPR sensor cell so as to identify a wavelength of the light which is attenuated. Here, if the wavelength of the attenuation is changed, it can be determined that an immune reaction is caused. It should be noted that the sample can easily be maintained in a void space defined by the through hole and the core.

According to another aspect of the present invention, the SPR sensor cell comprises: at least two cores, each having a surface area serving as an SPR sensing portion; a clad to cover the cores; and a through hole formed in the clad so as to communicate simultaneously with the SPR sensing portions.

In this configuration of the SPR sensor, a sample is brought into contact with at least two cores, forming the SPR sensing portion. The light is introduced into each of the cores and comes out of the SPR sensor cell. The light is analyzed to determine a wavelength distribution for each of the cores, thus performing an immunoassay.

According to still another aspect of the present invention, there is provided an immunoassay apparatus comprising: an SPR sensor cell having an SPR sensing portion; a light source for emitting light of a predetermined wavelength band into the SPR sensor cell; and a light analyzing means for analyzing light which has passed through the SPR sensor cell, wherein the light source is constituted by a white LED lamp.

This immunoassay apparatus operates as follows. Firstly, the white LED lamp emits a light of a predetermined bandwidth, which is introduced into the core of the SPR sensor. In the core, the light advances while being reflected and causes a surface plasmon resonance in the SPR sensing portion. Here the wavelength causing the surface plasmon resonance differs depending on the presence or absence of an immune reaction.

The light which has caused the surface plasmon resonance comes out of the core and is introduced into the light analyzing means. The light analyzing means enables to obtain a wavelength distribution. In an actual immunoassay, the wavelength distribution of the light of light source is analyzed beforehand, and the wavelength distribution is compared to a wavelength distribution after the immune reaction. Thus, it is possible to identify a wavelength of the light whose intensity has been reduced.

It should be noted that when the white LED lamp is used as the light source, it is possible to reduce the size of the immunoassay apparatus and to obtain flexibility of arrangement of the SPR sensor cell and the light analyzing means.

According to yet another aspect of the present invention, the SPR sensor cell comprises: a core having a rectangular cross section for passing light from a predetermined light source and having an SPR sensing portion on one of the side surfaces of the core; and at least two clads covering the core excluding the SPR sensing portion; wherein the side surfaces of the core other than the side surface having the SPR sensing portion and the side surface opposing to the side surface having the SPR sensing portion have a low-reflection surface where the light reflection is lowered.

The SPR sensor cell having the aforementioned configuration operates as follows. Firstly, the light source emits light of a predetermined bandwidth, which is introduced into the core of the SPR sensor. In the core, the light advances while being reflected repeatedly, causing a surface plasmon resonance in the SPR sensing portion in the SPR sensor cell. Here, the wavelength causing the surface plasmon differs, depending on the presence or absence of the immune reaction.

The light which has caused the surface plasmon resonance comes out of the core. On the other hand, the light which has no relation to the surface plasmon resonance and comes to the vicinity of the core surface is not reflected by the low-reflection surface. Accordingly, only the light portion having a relation to the surface plasmon resonance comes out of the core to be introduced in to the light analyzing means, where a wavelength of the light coming from the core is analyzed. In an actual immunoassay, a wavelength distribution is determined beforehand, which is then compared to the wavelength distribution after an immune reaction, so as to identify a wavelength of the light whose intensity has been reduced.

According to yet still another aspect of the present invention, there is provided an SPR sensor cell comprising: a sheet-shaped core transmitting light from a light source, having an SPR sensing portion, and sandwiched between a first clad and a second clad which has a through hole at a position corresponding to the SPR sensing portion.

The immunoassay apparatus using the aforementioned SPR sensor cell operates as follows. Firstly, the light source emits a predetermined wavelength band, which is introduced into the core of the SPR sensor cell. In the core, the light advances while being reflected repeatedly and causes a surface plasmon resonance in the SPR sensor cell. Here, the wavelength causing the surface plasmon resonance varies depending on the presence or absence of an immune reaction.

The light which has caused the surface plasmon resonance comes out of the core and is subjected to a wavelength distribution analysis in the light analyzing means. In an actual immunoassay, a wavelength distribution of the light source is analyzed beforehand and this is compared to a wavelength distribution after the immune reaction so as to determine which wavelength has been attenuated.

Moreover, the immunoassay apparatus according to the present invention comprises: a light source for emitting a predetermined wavelength band of light; an SPR sensor cell receiving the light from the light source so as to cause a surface plasmon resonance; and light analyzing means for analyzing the wavelength distribution of the light emitted from the SPR sensor cell constituted by a sheet-shaped core having a SPR sensing portion in a predetermined region and sandwiched by a first clad and a second clad.

BRIEF DESCRIPTION OF THE DRAWINGS

FIG. 1A shows an SPR sensor cell as a completed apparatus including a first clad shown in FIG. 1B, a core shown in FIG. 1C, and a second clad shown in FIG. 1D having an indentation 11 and a through hole 13.

FIG. 2 shows the completed SPR sensor cell disclosed in FIG. 1. FIG. 2A is a perspective view of the SPR sensor cell and FIG. 2B is a cross sectional view of the SPR sensor cell about the line indicated by the arrows in FIG. 2A.

FIG. 3 shows the SPR sensor cell of FIG. 1 with an incident light (L). FIG. 3A is a perspective view and FIG. 3B is a cross sectional view of the SPR sensor cell.

FIG. 4 shows a configuration of the SPR sensor cell of FIG. 1 having a thin metal film. FIG. 4A is a cross sectional view of the SPR sensor cell in the lateral direction. FIG. 4B is also a cross sectional view showing a state of surface plasmon resonance. FIG. 4C is a graph showing a calculated wavelength distribution of the outgoing light from the SPR sensor cell.

FIG. 5 shows the SPR sensor cell disclosed in FIG. 4 and having an antibody fixed.

FIG. 6 shows the SPR sensor cell disclosed in FIG. 5 to which light is introduced. FIG. 6A is a cross sectional view of the SPR sensor cell in which a surface plasmon resonance is caused. FIG. 6B is a graph showing a calculated wavelength distribution of the outgoing light from the SPR sensor cell.

FIG. 8A is a cross sectional view of the SPR sensor cell in which a surface plasmon resonance is caused. FIG. 8B is a graph showing a calculated wavelength distribution of the outgoing light from the SPR sensor cell.

FIG. 12 is a perspective view of a third embodiment of the present invention. FIG. 12A shows a sensor cell fixing table. FIG. 12B shows SPR sensor cells fixed on the fixing table.

FIG. 13 is a perspective view of a modified example of the third embodiment. FIG. 13A shows a sensor fixing table, and FIG. 13B shows SPR sensor cells fixed on the sensor fixing table.

FIG. 14A is a perspective view, FIG. 14B is a cross sectional view, and FIG. 14C is a plan view of the fourth embodiment.

FIG. 15 shows the SPR sensor cell disclosed in FIG. 14 to which light (L) is introduced. FIG. 15A is a perspective view and FIG. 15B is a cross sectional view of the SPR sensor cell.

FIG. 17A is a cross sectional view showing a surface plasmon resonance. FIG. 17B is a graph showing a wavelength distribution of the outgoing light from the SPR sensor cell.

FIG. 18 shows the SPR sensor cell of FIG. 16 having an antibody fixed.

FIG. 19 shows the SPR sensor cell disclosed in FIG. 18 into which light (L) is introduced. FIG. 19A is a cross sectional view showing a surface plasmon resonance. FIG. 19B shows a wavelength distribution of the outgoing light from the SPR sensor cell.

FIG. 20 is a cross sectional view of the SPR sensor cell of FIG. 18 having a sample fluid.

FIG. 21 shows the SPR sensor cell of FIG. 20 to which light (L) is introduced. FIG. 21A is a cross sectional view of the SPR sensor cell in which a surface plasmon resonance is present. FIG. 21B is a graph showing a wavelength distribution of the outgoing light from the SPR sensor cell.

FIG. 22 shows a modified example of the fourth embodiment of the present invention. FIG. 22A is a lateral cross sectional view of the modified example, and FIG. 22B is a graph showing a wavelength distribution of the outgoing light from the SPR sensor cell.

FIG. 25 shows an immunoassay apparatus comprising the SPR sensor cell according to the present invention. FIG. 25A shows the immunoassay apparatus already explained, and FIG. 25B shows an incident light into the SPR sensor cell at a predetermined angle.

FIG. 26 shows an SPR sensor cell according to a fifth embodiment of the present invention. FIG. 26A is a perspective view and FIG. 26B is a lateral cross sectional view of the fifth embodiment.

FIG. 28A shows a case when the light center axis from a light source is parallel to the longitudinal direction of the core. FIG. 28B shows a case when light is introduced at a predetermined angle with respect to the SPR sensor cell core.

FIG. 29 shows an SPR sensor cell according to a sixth embodiment of the present invention. FIG. 29A shows an optical waveguide. FIG. 29B shows a first clad constituting the SPR sensor cell. FIG. 29C shows a core sandwiched by third clads.

FIG. 30 is a perspective view of the SPR sensor cell having the optical waveguide disclosed in FIG. 29. FIG. 30A is a perspective view of the entire SPR sensor cell. FIG. 30B shows a substrate and FIG. 30C shows a second clad.

FIG. 31 shows the SPR sensor cell of FIG. 30 into which light is introduced. FIG. 31A is a perspective view of the entire SPR sensor cell. FIG. 31B is a cross sectional view of the SPR sensor.

FIG. 32 shows a modified example of the second clad used in the SPR sensor according to the present invention. FIG. 32A is a perspective view, FIG. 32B is a plan view, and FIG. 32C is a cross sectional view of the second clad.

FIG. 33A is a front view of a sample introducing tip for use with that second clad. FIG. 33B is a cross sectional view of another modified example of the second clad used in the SPR sensor cell.

FIG. 34 is a perspective view of an SPR sensor cell according to a seventh embodiment of the present invention. FIG. 34A shows the entire configuration of the SPR sensor cell including a substrate shown in FIG. 34B and a second clad shown in 34C.

FIG. 39A shows an entire configuration of the SPR sensor cell including a substrate shown in FIG. 39B, a core shown in FIG. 39C, and a second clad shown in FIG. 39D.

FIG. 40 shows an SPR sensor cell according to a tenth embodiment of the present invention. FIG. 40A shows a cell fixing table, and 40B shows the SPR sensor cells fixed on the sensor cell fixing table.

FIG. 41 is a perspective view of an SPR sensor cell according to Embodiment 11. FIG. 41A shows the SPR sensor in the complete state, and FIG. 41B shows two cores.

FIG. 42 is a cross sectional view of the SPR sensor of FIG. 41. FIG. 42A is a cross sectional view of a through hole, and FIG. 42B is an enlarged cross sectional view of an SPR sensor cell of FIG. 42A.

FIG. 43A shows the entire configuration of the SPR sensor cell; FIG. 43B shows a first clad; FIG. 43C shows cores and clads attached to the cores; and FIG. 43D shows a second clad.

FIG. 44 is a perspective view of Embodiment 13. FIG. 44A shows a second clad constituted by a combination of four members, and FIG. 44B also shows a second clad constituted by another combination of four members.

FIG. 45 is a perspective exploded view of an SPR sensor cell according to Embodiment 14 having a first clad, a second clad, and cores.

FIG. 46A shows the entire configuration; FIG. 46B shows a first clad; FIG. 46C shows cores and longer and shorter clads; and FIG. 46D shows a second clad.

FIG. 51 is a perspective view of modified examples of an SPR sensor cell used in the immunoassay apparatus according to the present invention. FIG. 51A shows an SPR sensor cell having a single core, and FIG. 51B shows an SPR sensor cell having two cores.

FIG. 59A shows the entire configuration of the SPR sensor. FIG. 59B shows a first clad, FIG. 59C shows a core and a clad attached to the core, and FIG. 59D shows a second clad.

FIG. 60A shows the entire configuration of the SPR sensor. FIG. 60B shows a first clad, FIG. 60C shows a core and a clad attached to the core, and FIG. 60D shows a second clad.

FIG. 61 is a perspective view of other modified examples of the SPR sensor cell according to Embodiment 24. FIG. 61A shows an example of the SPR sensor cell having one core. FIG. 61B shows an example of the SPR sensor cell having two cores.

FIG. 63A shows the entire configuration of the SPR sensor cell. FIG. 63B shows a first clad. FIG. 63C shows cores and clads attached to the cores. FIG. 63D shows a second clad.

FIG. 65A shows the entire configuration; FIG. 65B shows a first clad; FIG. 65C shows a core; and FIG. 65D shows a second clad.

FIG. 67A is a side cross sectional view and FIG. 67B is a cross sectional view from the top.

FIG. 68 shows a pin hole plate used in the immunoassay apparatus according to the resent invention: FIG. 68A shows a pin hole plate having a single pin hole; and FIG. 68B shows a pin hole plate having eight pin holes.

FIG. 71A shows the entire configuration of the SPR sensor cell; FIG. 71B shows a first clad; FIG. 71C shows a sheet-shaped core; and FIG. 71D shows a second clad.

FIG. 72A shows the entire configuration of the SPR sensor cell; FIG. 72B shows a first clad; FIG. 72C shows a sheet-shaped core; and FIG. 72D shows a second clad.

FIG. 73A shows the entire configuration of the SPR sensor cell; FIG. 73B shows a first clad; FIG. 73C shows a sheet-shaped core; and FIG. 73D shows a second clad.

FIG. 74A shows the entire configuration of the SPR sensor cell; FIG. 74B shows a second clad; FIG. 74C shows a first clad; FIG. 74D shows a sheet-shaped core; FIG. 74E shows a non-light transparent member and FIG. 74F shows a light transparent member constituting the core.

FIG. 75A shows the entire configuration of the SPR sensor cell; FIG. 75B shows a second clad; FIG. 75C shows a first clad; FIG. 75D shows a sheet-shaped core; FIG. 75E shows a non-light-transparent member; FIG. 75F shows a light transparent member constituting the core and FIG. 75G shows a short non-light-transparent member.

FIG. 76A shows the entire configuration of the SPR sensor cell; FIG. 76B shows a first clad; FIG. 76C shows a sheet-shaped core; FIG. 76D and 76F show non-light transparent members; FIG. 76E shows a light transparent member, which members constitute the sheet-shaped core; FIG. 76G shows a second clad.

FIG. 77A is a cross-sectional view of the immunoassay apparatus, and FIG. 77B is a plane view of the immunoassay apparatus.

FIG. 86A is a plan view and FIG. 86B is a side view.

FIG. 87A is a side view and FIG. 86B is a front view of the optical fiber fixing portion having a cylindrical member; FIG. 87C is a side view and FIG. 87D is a front view of the optical fiber fixing portion having no cylindrical member.

FIG. 88 schematically shows an entire configuration of an immunoassay apparatus according to Embodiment 37: FIG. 88A is a plan view and FIG. 88B is a side view.

DESCRIPTION OF THE PREFERRED EMBODIMENTS

Embodiment 1

Figure 1:
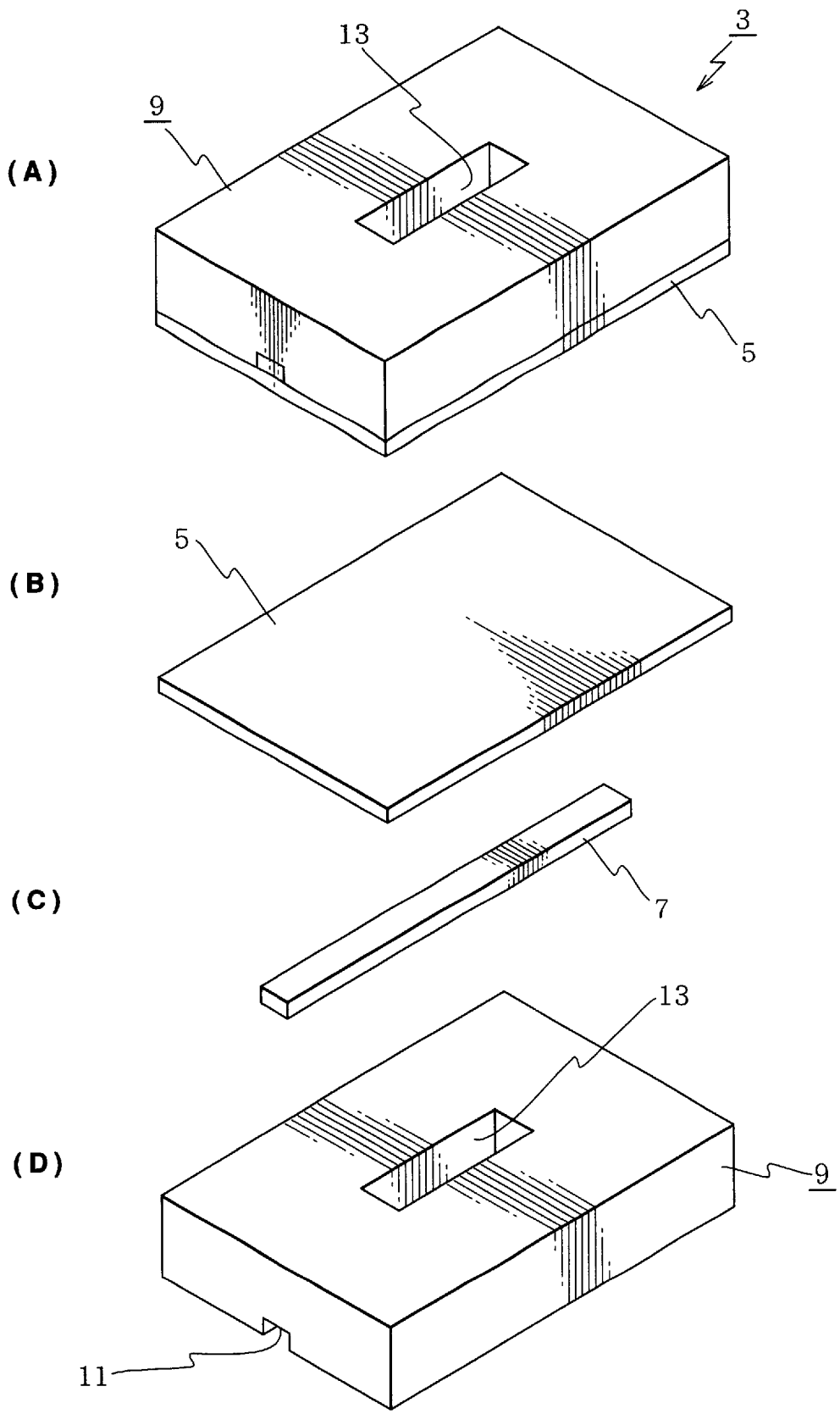
FIG. 1 is a perspective view of an SPR sensor cell according to a first embodiment of the present invention.

Description will now directed to a first embodiment of the present invention.

Firstly, referring to FIG. 1 to FIG. 8, explanation will be given on an SPR sensor cell 3 which is a characteristic component of the immunoassay apparatus according to the first embodiment. The SPR sensor according to the present invention employs an optical waveguide. More specifically, the SPR sensor cell 3 includes: plate-shaped first clad (substrate) 5; a core 7 provided on this first clad 5; and a second clad (upper plate) covering the core 7 and the surface of the first clad 5. It should be noted that various types of optical waveguides are available such as a plane type, strip type, embedded type, lens type, and the like. These components will be detailed below.

The first clad 5 is made from a material such as glass and has a thin plate shape. The core 7 is placed on this first clad. The core transmits light and extend over the entire length of the optical waveguide. The core is made from, glass, plastic, or the like. On the surface of the first clad, the second clad 9 is provided so as to surround the core 7. More specifically, the second clad has an indentation 11 formed at the bottom. When the second clad 9 is placed on the first clad 5, the core 7 is engaged with this indentation 11 and the bottom of the second clad 9 is brought into full contact with the first clad 5.

When mounting the core 7 on the first clad 5, an adhesive can be used or thermal processing can be used to melt the boundary between the core 7 and the first clad 5. This also applies to the boundary between the second clad 9 and the first clad 5. It should be noted that when an adhesive is used for fixing the core 7 onto the first clad 5, considering the light attenuation, it is necessary to use an adhesive having a lower refraction factor than that of the core 7.

Moreover, the second clad 9 has a predetermined through hole 13 extending from the upper surface of the second clad 9 to reach the surface of the core 7. Accordingly, a surface of the core 7 is exposed via this through hole 13. Note that as will be detailed later, a thin metal film is formed on the part of the core 7 corresponding to this through hole. The through hole 13 may be provided by making a through hole in a single plate-shaped clad, or may be provided by combination of a plurality of block-shaped members.

Here, the first clad 5, the core 7, and the second clad 9 should have refraction factors in a predetermined relation so that the core 7 serves as an optical waveguide. More specifically, the core 7 should have a greatest refraction factor and then the second clad should have a next greatest factor. Furthermore, the first clad 5 should have a refraction factor equal to or smaller than the second clad 2.

FIG. 3 shows light L passing through the SPR sensor cell. The light L introduced into one end of the SPR sensor cell 3 advances while repeating a total reflection and goes out from the other end of the SPR sensor cell 3.

FIG. 4 is a cross sectional view of the core on which a thin metal film 15 has been formed from Au. In order to constitute the SPR sensor, deposition or the like is employed using gold (Au). The material of the thin metal film may also be silver (Ag).

As shown in FIG. 4B, when a wide-band light L is introduced into the core coated with Au or the like, a surface plasmon resonance is generated in this area. More specifically, a predetermined wavelength of the light generates the surface plasmon resonance and the light of this wavelength is attenuated. Accordingly, the outgoing light from the SPR sensor cell 3 is attenuated at the predetermined wavelegth as shown in FIG. 4C. However, wavelength distribution is calculated as follows method actually. That is, an output value of sample spectrum should be divided by an output value of reference spectrum according to each wavelength. Therefore, the divided value of light intensity will be reduce to under 1.0 when a light intensity decrease by immunoassay.

Next, as shown in FIG. 5 and FIG. 6, an antibody (or antigen) 19 is fixed via a predetermined dielectric film 17 on the thin metal film 15 formed from Au. This antibody (or antigen) is selected according to the antigen (or antibody) contained in a sample to be assayed.

After this, as shown in FIG. 6A, light L is introduced into the core 7 to generate a surface plasmon resonance in the same way as has been described. However, because an antigen is fixed, the wavelength generating the surface plasmon resonance varies. Accordingly, as shown in FIG. 6B, the curve showing the wavelength distribution is slightly shifted. A wavelength distribution is calculated by same method described about FIG. 4C.

Figure 7:
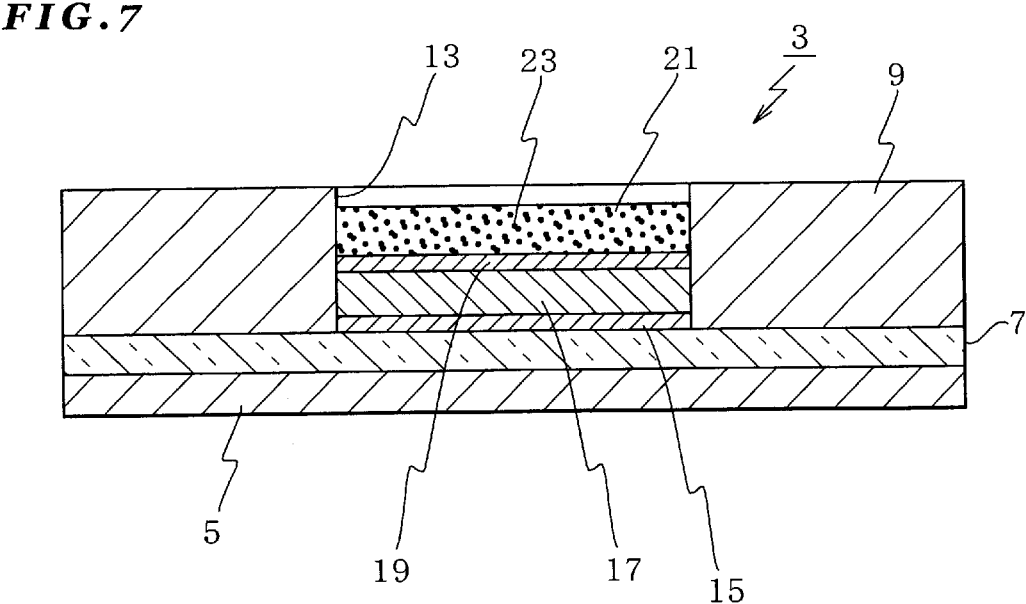
FIG. 7 is a cross sectional view of the SPR sensor cell into which a sample fluid is introduced.
Figure 8:
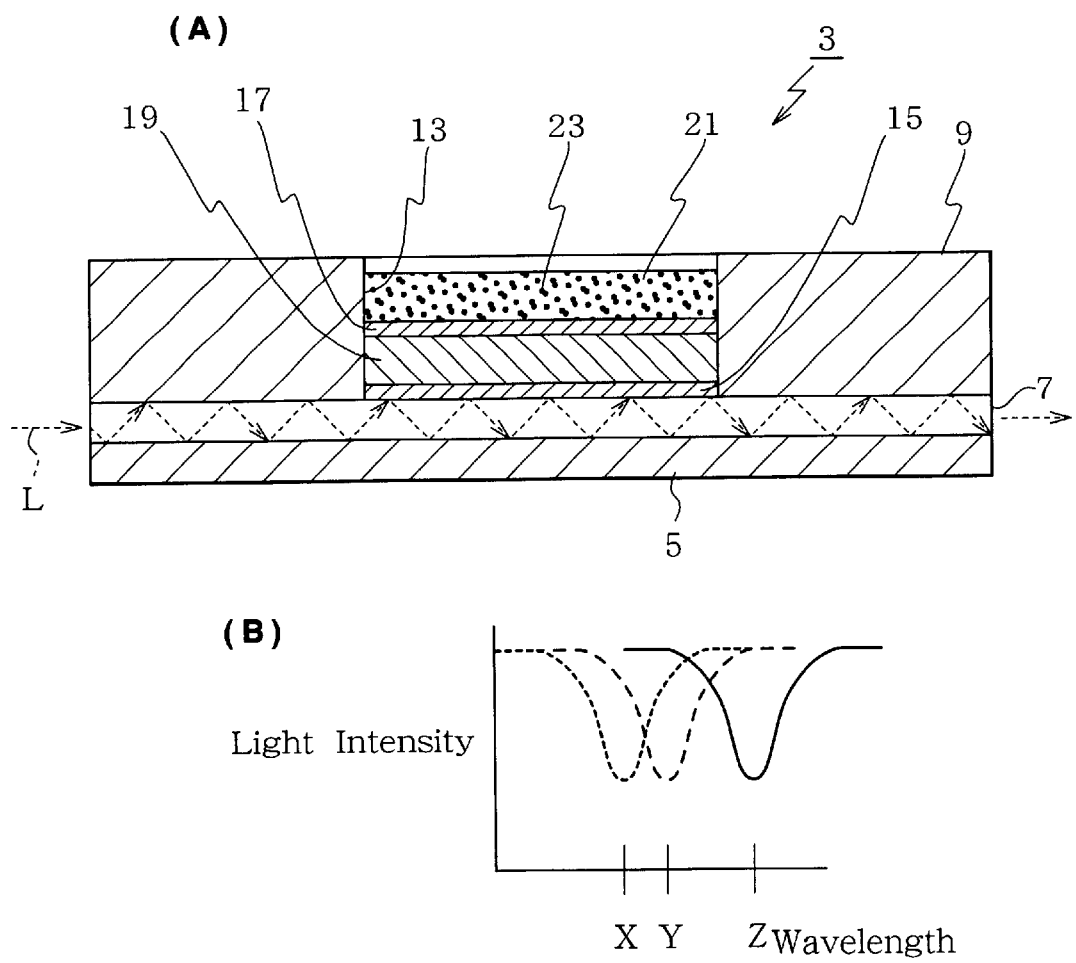
FIG. 8 shows the SPR sensor cell disclosed in FIG. 7 into which light is introduced.

FIG. 7 shows the through hole 13 formed in the second clad 9 and filled with a sample fluid 21. The sample fluid 21 contains a predetermined antigen 23. Accordingly, if the sample fluid 21 contains an antigen 23 which specifically reacts to the antibody 19 fixed to the Au film, there arises an antigen-antibody reaction. This antigen-antibody reaction also changes the light wavelength generating the surface plasmon resonance.

Accordingly, as shown in FIG. 8A, light L is introduced into the core 7 and the wavelength distribution after the antigen-antibody reaction is analyzed so as to determine a wavelength attenuated, thus enabling to perform an immunoassay. FIG. 8B shows shifting of the attenuated light wavelength. A wavelength distribution is calculated by same method described about FIG. 4C.

Figure 9:
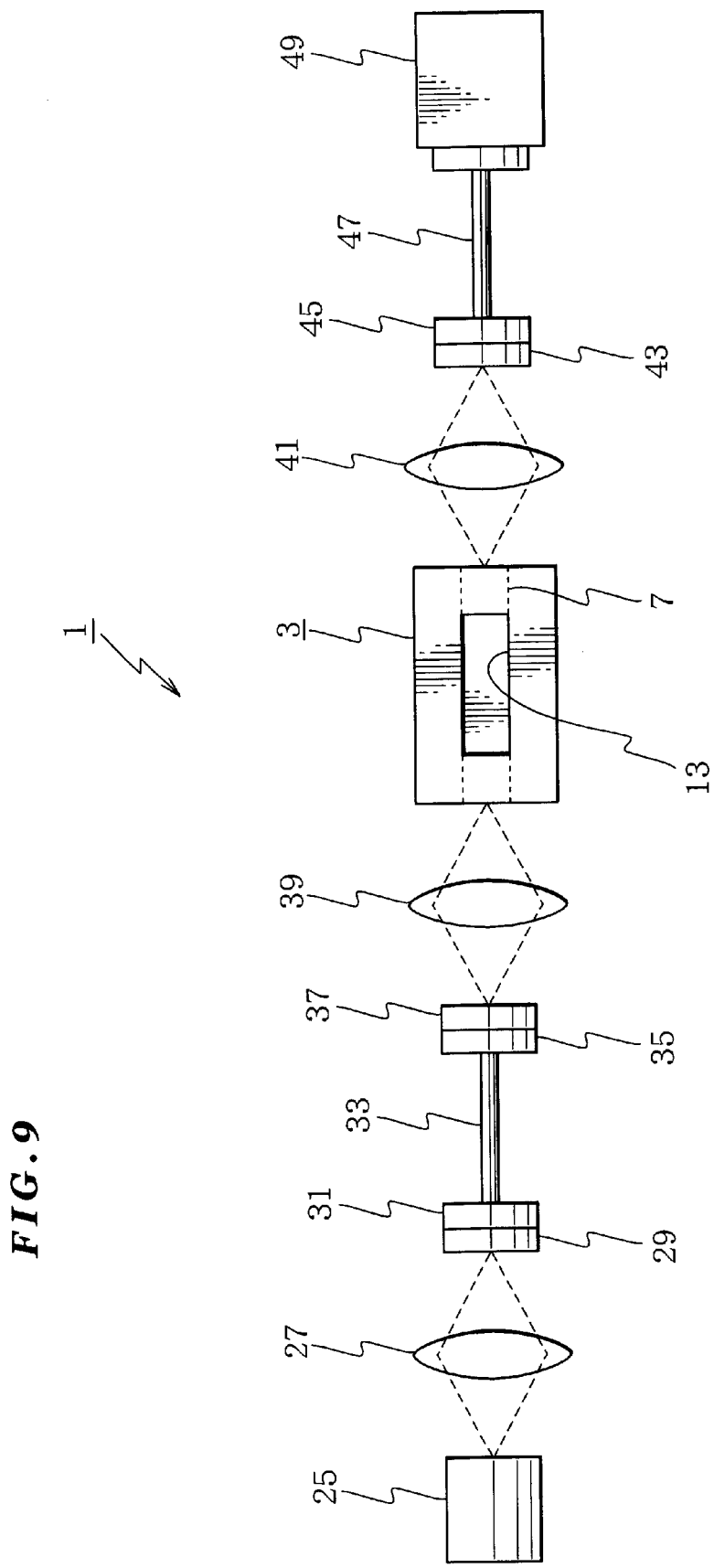
FIG. 9 is a plan view of an immunoassay apparatus comprising the SPR sensor cell disclosed in FIG. 7.

FIG. 9 shows an entire configuration of the immunoassay apparatus 1. Firstly, explanation will be given on a light source 25. The light source 25 emits light L having a wide band of wavelength. For example, a halogen lamp can be used. The light L emitted from the light source 25 is converged by a converging lens 27 and then introduced into a receptacle 29 which is connected to an optical fiber connector 31. Thus, the light L is introduced via the optical fiber connector 31 into an optical fiber 33. The light L which has passed through the optical fiber 33 further passes through an optical fiber connector 35 and a receptacle 37 to reach a converging lens 39. The light L which has passed through the converging lens 39 is introduced into the SPR sensor cell 3.

The light L introduced into the SPR sensor passes through the core 7. Here, at the thin metal film of Au, the surface plasmon resonance is generated. This surface plasmon resonance lowers the light intensity of a particular wavelength when the light L goes out from the SPR sensor cell 3.

The light L outgoing from the SPR sensor 3 passes through a converging lens 41 to reach a receptacle 43 which is connected to an optical fiber connector 45. The light L advances into the receptacle 43 and then passes through the optical fiber connector 45 and an optical fiber 47 to reach a predetermined spectrometer 49.

The spectrometer 49 analyzes the wavelength distribution of the incident light L. More specifically, a wavelength distribution is determined prior to the immune reaction. Then, a wavelength distribution after the immune reaction is checked. The difference between these wavelength distributions obtained is used to determine presence of an immune reaction or a state of the immune reaction.

Embodiment 2

Figure 10:
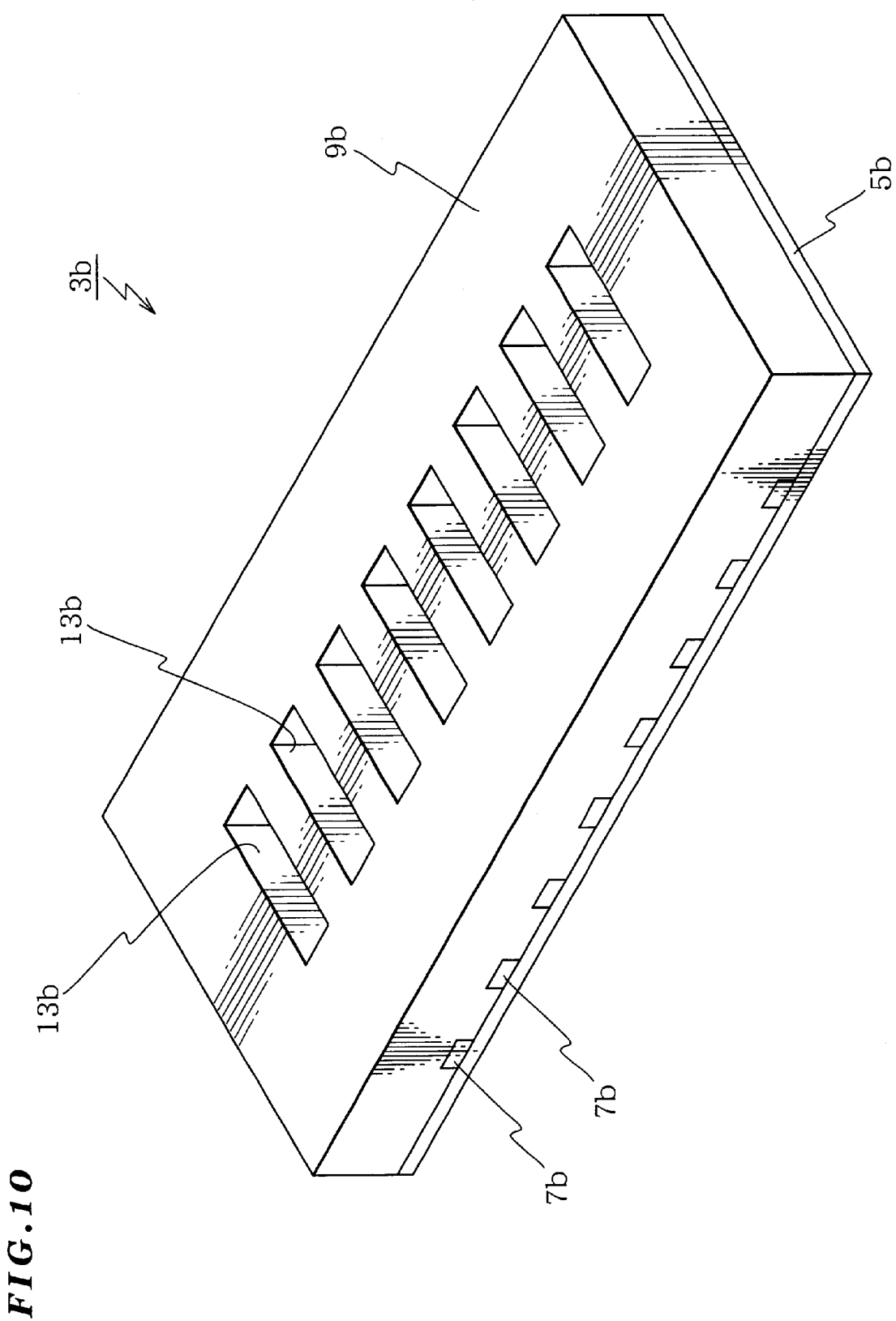
FIG. 10 is a perspective view of an SPR sensor cell according to a second embodiment of the present invention.

FIG. 10 is a perspective view of an SPR sensor cell 3b used in an immunoassay apparatus according to the second embodiment. This SPR sensor cell 3b is basically identical to the SPR sensor cell 3 of the first embodiment except for that a plurality of cores 7b are provided in a single SPR sensor cell 3b, and a plurality of through holes 13b are provided corresponding to the cores 7b.

As for the production method of the SPR sensor cell 3b, a plurality of cores 7b are arranged in parallel to one another on a first clad 5b made from a predetermined clad. Then, a second clad 9b is fixed on to the first clad so as to cover the cores 7b. Here, an adhesive is used to fix the cores 7b onto the first clad 5b, and to fix the second clad 9b onto the first clad 5b.

When performing an immunoassay, each of the through holes 13b is filled with a sample fluid and the light L is introduced into the core 7b. It is preferable that different antibodies be fixed according to the antigens to be assayed. This enables to rapidly perform various immune reactions. It is also possible to fix a single antibody, and fill the through holes with different samples. Thus, different samples can be subjected to an immunoassay.

Figure 11:
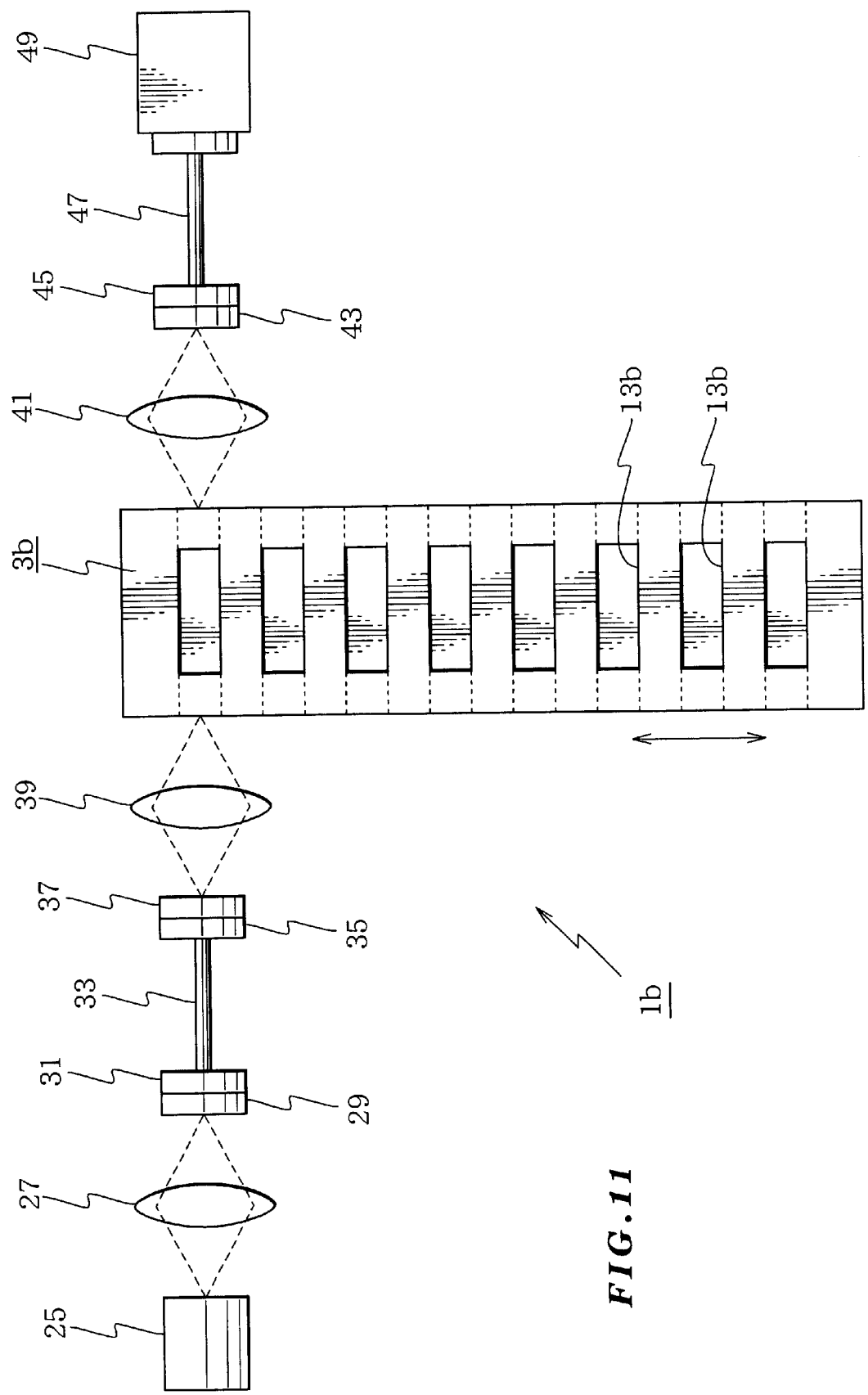
FIG. 11 is a plan view of an immunoassay apparatus comprising the SPR sensors cell disclosed in FIG. 10.

FIG. 11 schematically shows an entire immunoassay apparatus comprising the SPR sensor cell 3b according to the second embodiment. This embodiment uses only one light source 25 and one spectrometer 49. Accordingly, the optical waveguide should switched for the immunoassay of the cores 7b. For this, the SPR sensor cell 3b is movably formed. More specifically, the SPR sensor cell is moved in a direction vertical to the optical waveguide from the light source 25 and the spectrometer 49, and is stopped at positions corresponding to the respective cores 7b.

It should be noted that the second embodiment has been explained for a case that between the light source 25 and the spectrometer 49 there are provided the optical fiber 33, optical fiber connector 31 and receptacle 29. However, this embodiment is not to be limited to such a case but it is also possible to introduce the light L from the light source directly into the SPR sensor cell 3b so that the outgoing light from the SPR sensor 3b is directly introduced into the spectrometer.

Moreover, in this embodiment, the SPR sensor cell 3b has a plurality of through holes 13b on the second clad. These through holes 13b may be formed in a single member by mechanical processing or it is also possible to use a plurality of block-shaped members to define the through holes as shown in FIG. 10.

Embodiment 3

FIG. 12 is a perspective view of a sensor cell fixing table 51 on which the SPR sensor cell 3 according to the first embodiment can be fixed. On this sensor cell fixing table 51, a plurality of the SPR sensor cells 3 can be fixed at an identical interval. In FIG. 12, three SPR sensor cells are fixed on the table. However, it is also possible to increase or decrease the number of the SPR sensor cells as is required.

The sensor cell fixing table 51 has partitions to define respective positions for accepting the SPR sensor cells 3. The SPR sensor cells 3 cannot be moved in the direction of the arrangement (rightward or leftward in FIG. 12). Moreover, each of the partitions has an engagement member so that the SPR cells 3 cannot be moved in the longitudinal direction of the cores 7. Thus, the SPR sensor cells 3 can be replaced or removed in the perpendicular direction but cannot be moved in a horizontal direction.

Moreover, the sensor cell fixing table 51 is arranged so as to be moved by a moving mechanism (not depicted). By moving the sensor cell fixing table 51, different cores 7 can be set on the optical waveguide from the light source. Accordingly, it is possible to successively and rapidly perform an immunoassay for a plurality of samples. Moreover, when the immunoassay is complete, the SPR sensor cells 3 can easily be replaced.

FIG. 13 shows a sensor cell fixing table 51c for fixing the SPR sensor cell 3b explained in the second embodiment. This sensor cell fixing table the is for fixing the SPR sensor cell 3b having a plurality of cores 7b. The SPR sensor cell 3b fixed on this table cannot move in a horizontal direction. Note that this sensor cell fixing table 51c is also arranged to be movable by a predetermined moving mechanism. In the case of the SPR sensor cell 3b having a plurality of cores 7b, the cores 7b should be positioned on the optical path.

Embodiment 4

Figure 14:
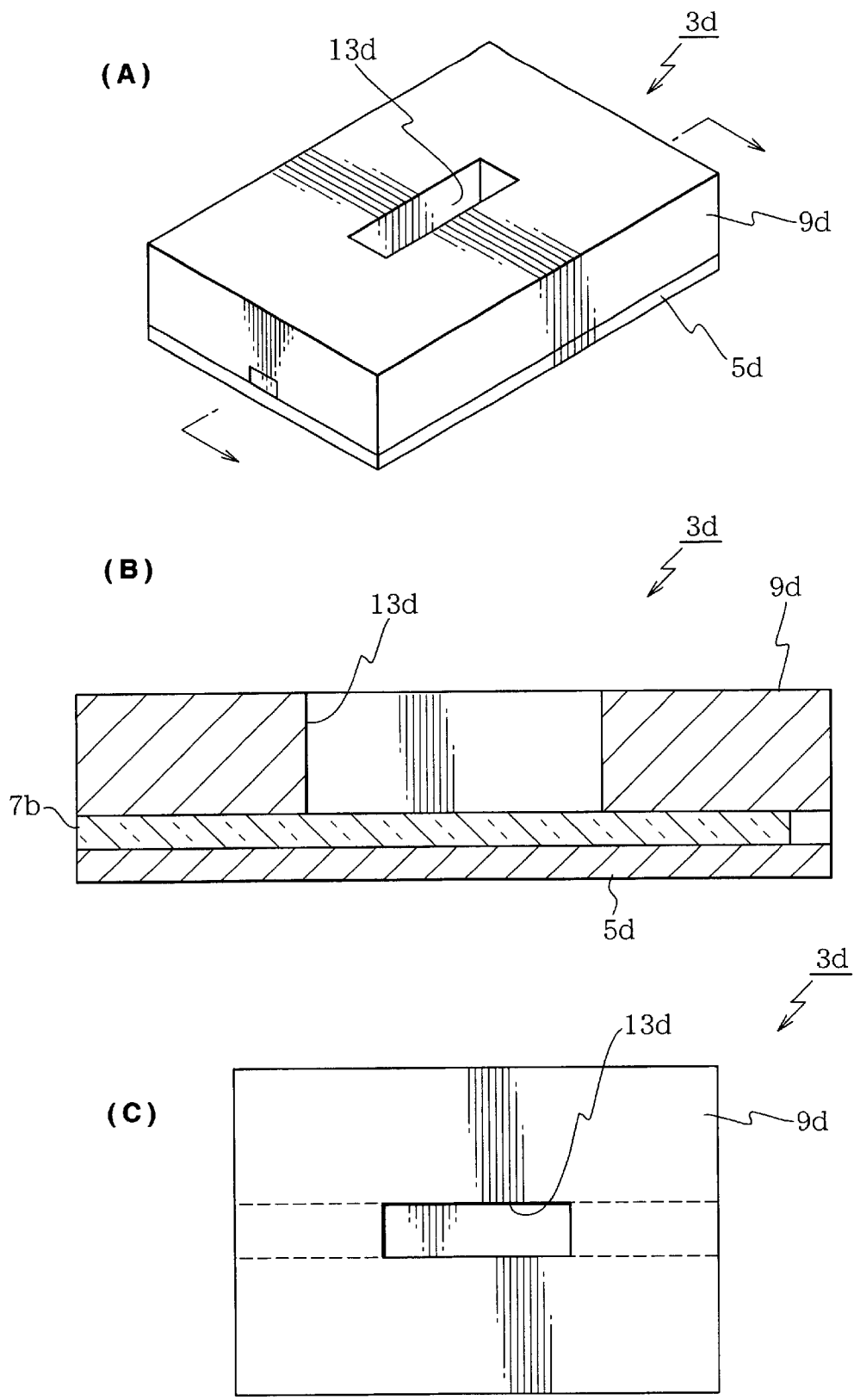
FIG. 14 shows a configuration of a fourth embodiment of the present invention.

FIG. 14 shows an SPR sensor cell 3d to be used in an immunoassay apparatus according to a fourth embodiment of the present invention. This SPR sensor cell 3d has a basically identical configuration as the aforementioned first embodiment except for that a core 7d is slightly shorter than the length of the entire SPR sensor cell 3d.

As shown in FIG. 15, if light L is introduced from one end of the core 7d, the light goes out of the other end of the core 7d in the same way as the first embodiment.

Figure 16:
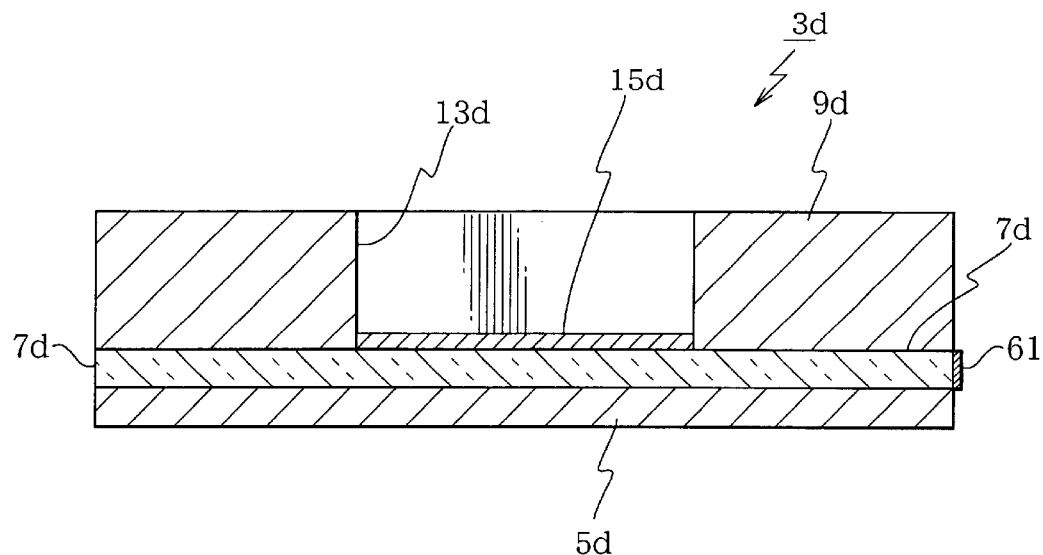
FIG. 16 is a cross sectional view of the SPR sensor cell disclosed in FIG. 14 and having a thin metal film formed.

On the other hand, as shown in FIG. 16, in this embodiment, a thin metal film of Ag is deposited on the other end of the core 7d, so as to be used as a reflection surface (mirror). Moreover, in the same way as in the first embodiment, a thin metal film 15d of Au is formed at a portion corresponding to the through hole 13d on the surface of the core 7d.

Figure 17:
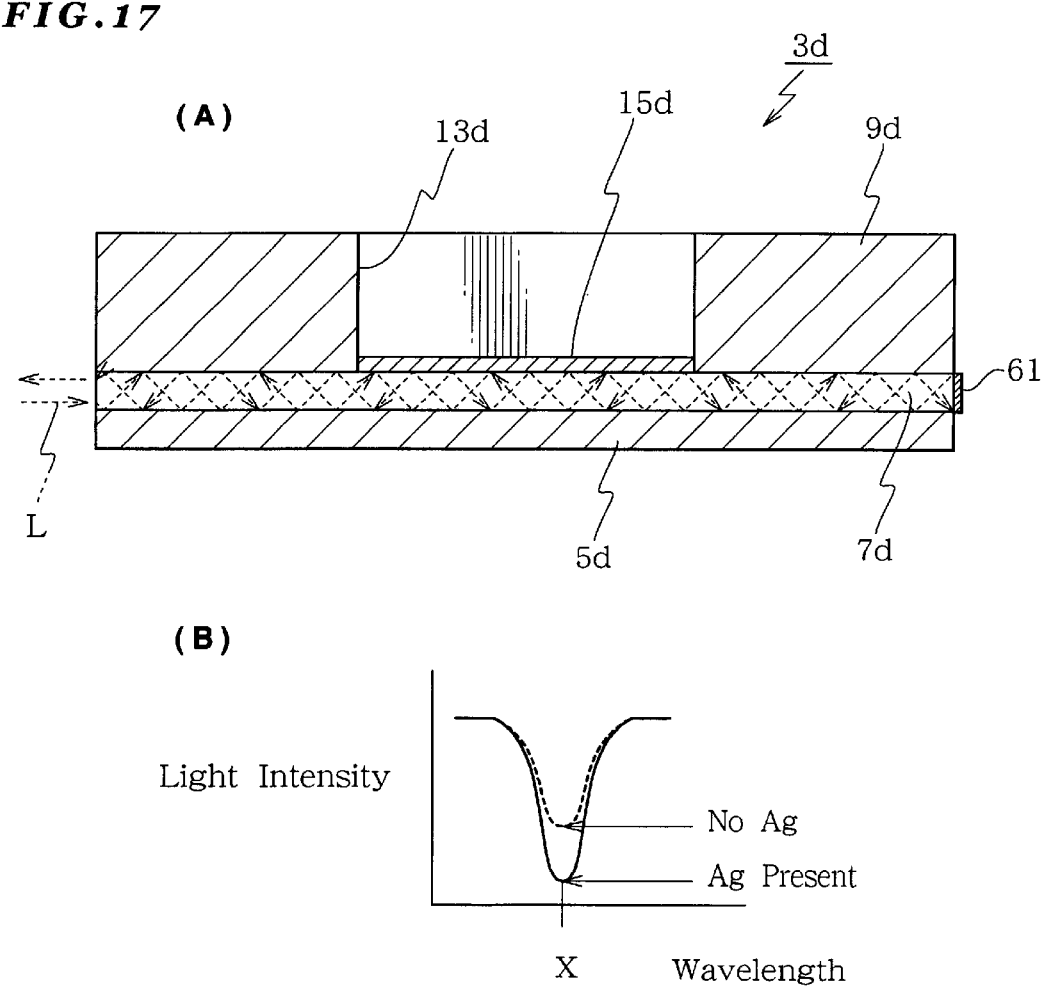
FIG. 17 shows the SPR sensor cell of FIG. 16 to which light (L) is introduced.

FIG. 17A shows a case that the light L is actually introduced into the core 7d of the SPR sensor cell 3d. The light L introduced from one end (hereinafter referred to as a first end) generates a surface plasmon resonance at the thin metal film 15d of Au and reflected by the thin metal film 61 at the other end (hereinafter referred to as a second end) of the core 7d.

Referring to FIG. 17B, the light L reflected by the thin mental film of the second end of the core 7d shows attenuation of a particular wavelength of the light L. As shown in FIG. 17B, when the thin metal film 61 of Ag is present, the particular wavelength of the light L is more attenuated than the case when the thin metal film 61 of Ag is absent. On the other hand, the other wavelength shows almost no attenuation. This is because the surface plasmon resonance is generated before the light reaches the second end of the core 7d, and the surface plasmon resonance is also generated by the reflected light. This substantilly improves the sensitivity of the SPR sensor cell.

Next, as shown in FIG. 18, an antibody (or antigen) is fixed on the thin metal film 15d of Au via a predetermined dielectric film 17d. The antibody (or antigen) 19d is selected according to an antigen (or antibody) contained in the sample. After the antibody 19d is fixed, as shown in FIG. 19A, the light L is introduced into the core 7d, which generates the surface plasmon resonance. Here, the wavelength of the light causing the surface plasmon resonance is changed because the antibody 19d is applied. Thus, the wavelength distribution curve is slightly shifted as shown in FIG. 19B.

FIG. 20 shows the SPR sensor cell 3d having a sample 21d filled in the through hole 13d formed in the second clad 9d. The sample 21d contains a predetermined antigen 23d. Accordingly, if the sample 21d contains an antigen specifically reacts to the antibody 19d fixed to the dielectric film 17d of Au, an antigen-antibody reaction is caused. This antigen-antibody reaction also changes the wavelength of the light causing the surface plasmon resonance.

As shown in FIG. 21A, the light L is introduced into the core 7d, and the wavelength distribution is checked after the antigen-antibody. The immunoassay is performed according to the wavelength attenuated. FIG. 21B shows the wavelength attenuated which has been shifted.

FIG. 22 is a cross sectional view of the SPR sensor cell 3d1 having a second end surface entirely covered with a thin metal film 63 of Ag. This is because formation of the thin metal film 63 is easier compared to the formation of the thin metal surface to cover only the end surface of the core 7d. That is, when forming a thin mental film only on the end surface of the core 7d, deposition should be selectively performed on the core 7d.

The SPR sensor cell 3d1 having the thin metal film 63 covering the entire end surface, as shown in FIG. 22B, also changes the wavelength attenuated by the immune reaction and can perform the immunoassay.

Figure 23:
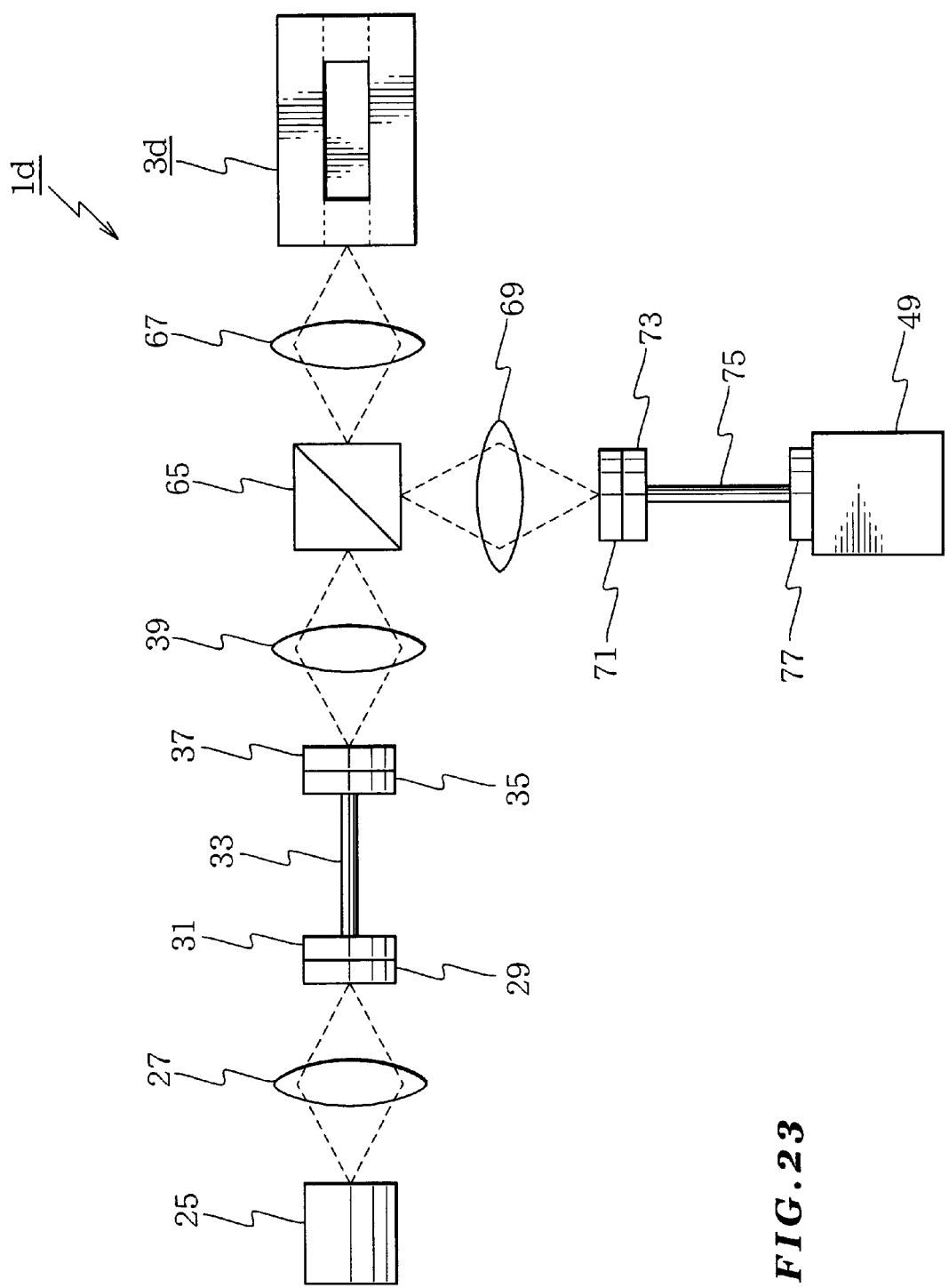
FIG. 23 is a plan view of an immunoassay apparatus comprising the SPR sensor cell disclosed in FIG. 14.

FIG. 23 shows an entire configuration of the immunoassay apparatus 1d. Firstly, explanation will be given on the light source 25 for emitting the light L for an immunoassay. The light source 25 is for emitting the light L of a wide-band wavelength. For example, a halogen lamp can be used. The light L emitted from the light source 25 is converged by a converging lens 27 and introduced into a receptacle 29 which is connected to an optical fiber connector 31. The light L from the light source 25 is introduced via the optical fiber connector 31 into an optical fiber 33. The light L which has passed through the optical fiber 33 further advances into an optical fiber connector 35 and a receptacle 37 to reach a converging lens 39. The light L which has passed through the converging lens 39 partially passes through a beam splitter 65 and a converging lens 67 to advance into one end of the SPR sensor cell 3d.

The light L introduced into the SPR sensor cell 3d passes through the core, causing a surface plasmon resonance at the thin metal film of Au as has been explained above. The surface plasmon resonance lowers the light intensity of a particular wavelength, and the light is reflected by the core end surface of the SPR sensor cell 3d. The light L reflected by the core end surface goes back through the SPR sensor cell 3d and goes out of the first end of the SPR sensor cell. The light further passes through a converging lens 67 and enters a beam splitter 65. A part of the light L is reflected in the vertical direction by a reflection surface of the beam splitter 65.

The reflected part of light L passes through a predetermined converging lens 69 and advances through a receptacle 71, an optical connector 73, an optical fiber 75 and enters a spectrometer 49.

Figure 24:
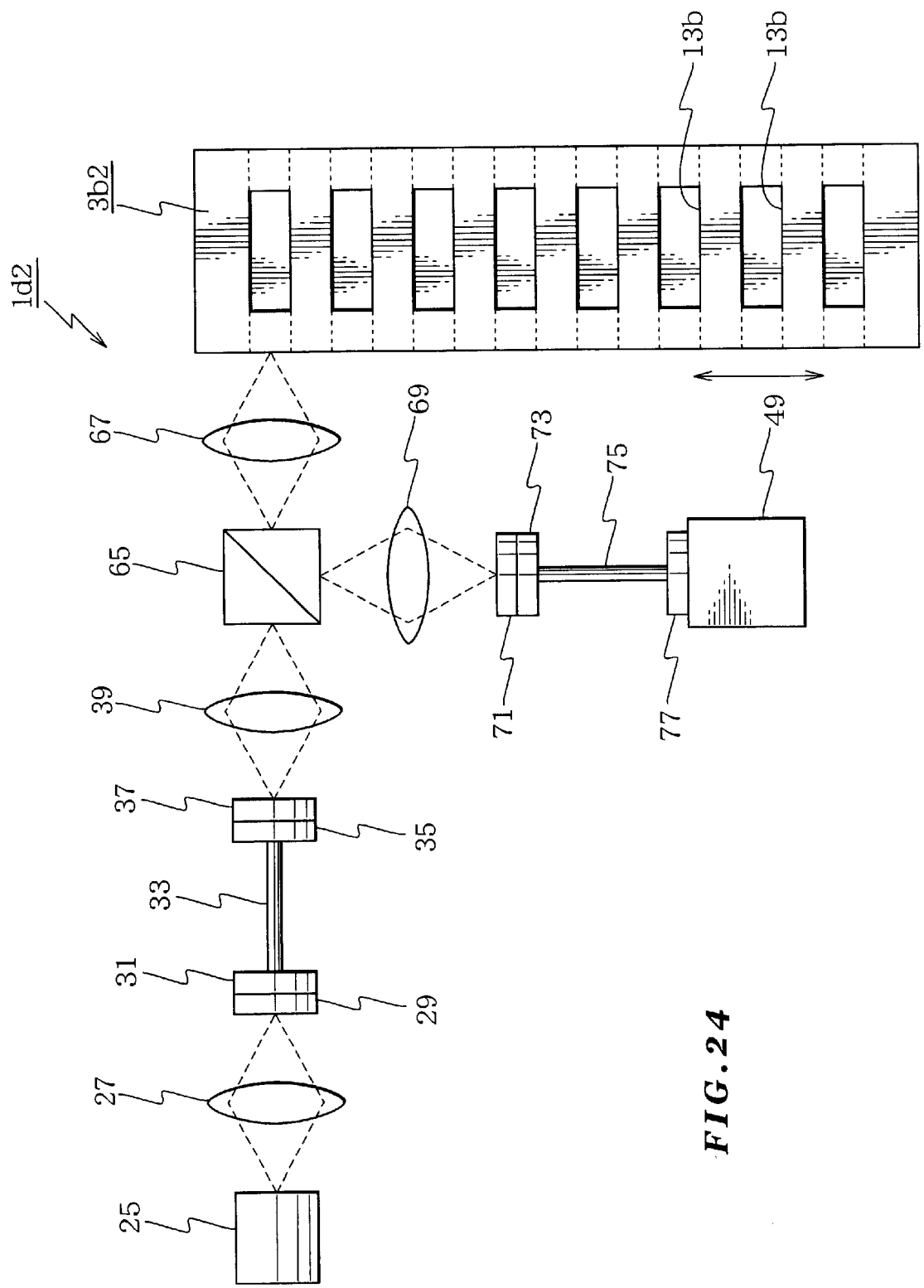
FIG. 24 is a plan view of an immunoassay apparatus comprising a plurality of SPR sensor cells.

FIG. 24 shows configuration of the immunoassay apparatus using the SPR sensor cell 3d1 has a plurality of cores. This configuration has various advantages as follows. If a single antibody is fixed in the respective cores, immunoassay can be quickly performed for a plurality of different samples. Moreover, if different antibodies are fixed in the respective cores, it is possible to quickly perform immunoassay on different antigens in a single sample. For this, the SPR sensor cell can be moved with respect to the optical path from the light source 25.

Next, FIG. 25 shows a modified example of the immunoassay apparatus shown in FIG. 9.

FIG. 25A shows the entire configuration of the immunoassay apparatus 1 explained already. FIG. 25B shows that the light L is introduced into the SPR sensor cell 3 at a predetermined angle. With the configuration of FIG. 25B also, the light is introduced into the core 7 and passes through the core 7 while being totally reflected. That is, the configuration of FIG. 25B also can perform the immunoassay. It is known that when a light is introduced into the core at an angle with respect to the core surface, it is possible to improve a light introduction efficiency under a certain condition.

Embodiment 5

Description will now be directed to a fifth embodiment with reference to FIG. 26.

As shown in FIG. 26, in this embodiment an SPR sensor 3e has inclined end surfaces (first and second end surfaces). That is, the core 7e has inclined end surfaces and the second clad 9e also has inclined end surfaces so as to be flat with the inclined end surfaces of the core 7e. However, the second clad 9e may not have inclined end surfaces.

When the core 7e has end surfaces inclined, it is possible to effectively introduce the light in a normal line direction into the core 7e. Accordingly, the inclination angle to be formed on the core 7e should be set according to the direction of the incident light L from the light source 25. In the example of FIG. 26, the inclination angle is about 45 degrees with respect to the bottom of the SPR sensor cell 3e.

Figure 27:
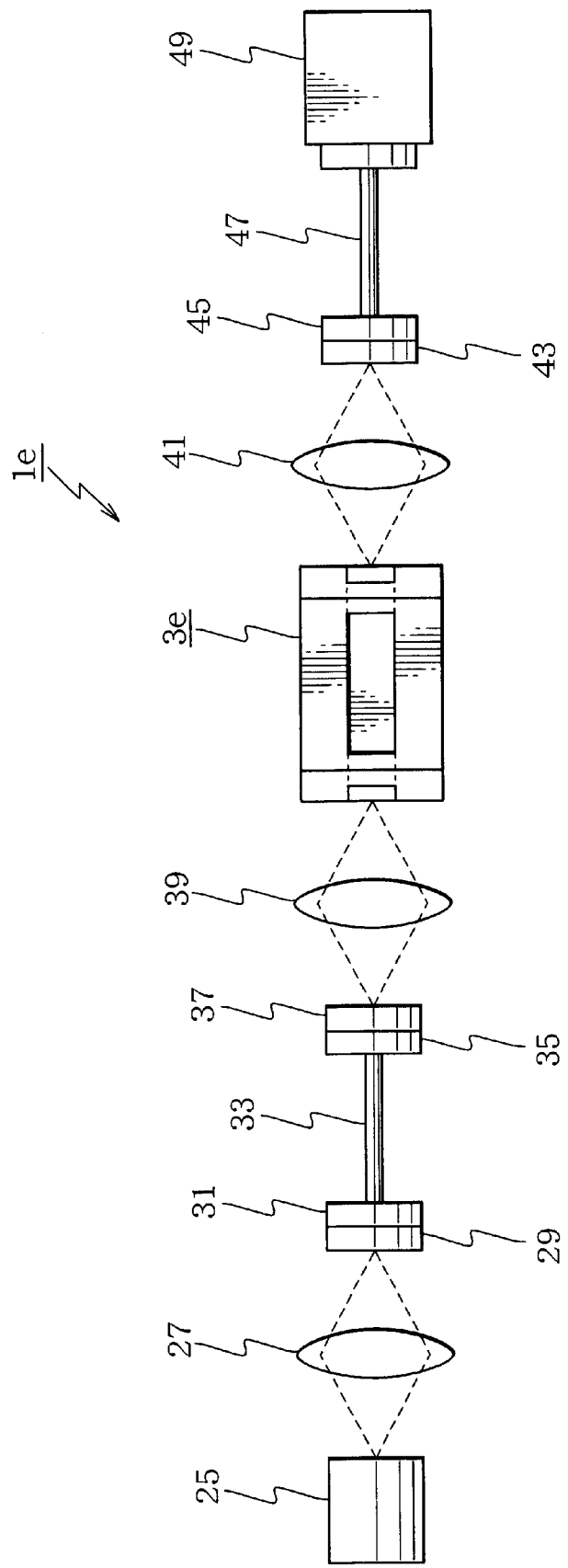
FIG. 27 is a plan view of an immunoassay apparatus comprising the SPR sensor disclosed in FIG. 26.

FIG. 27 shows an entire configuration of the immunoassay apparatus 1e using the SPR sensor cell including the core 7e having inclined end surfaces.

Figure 28:
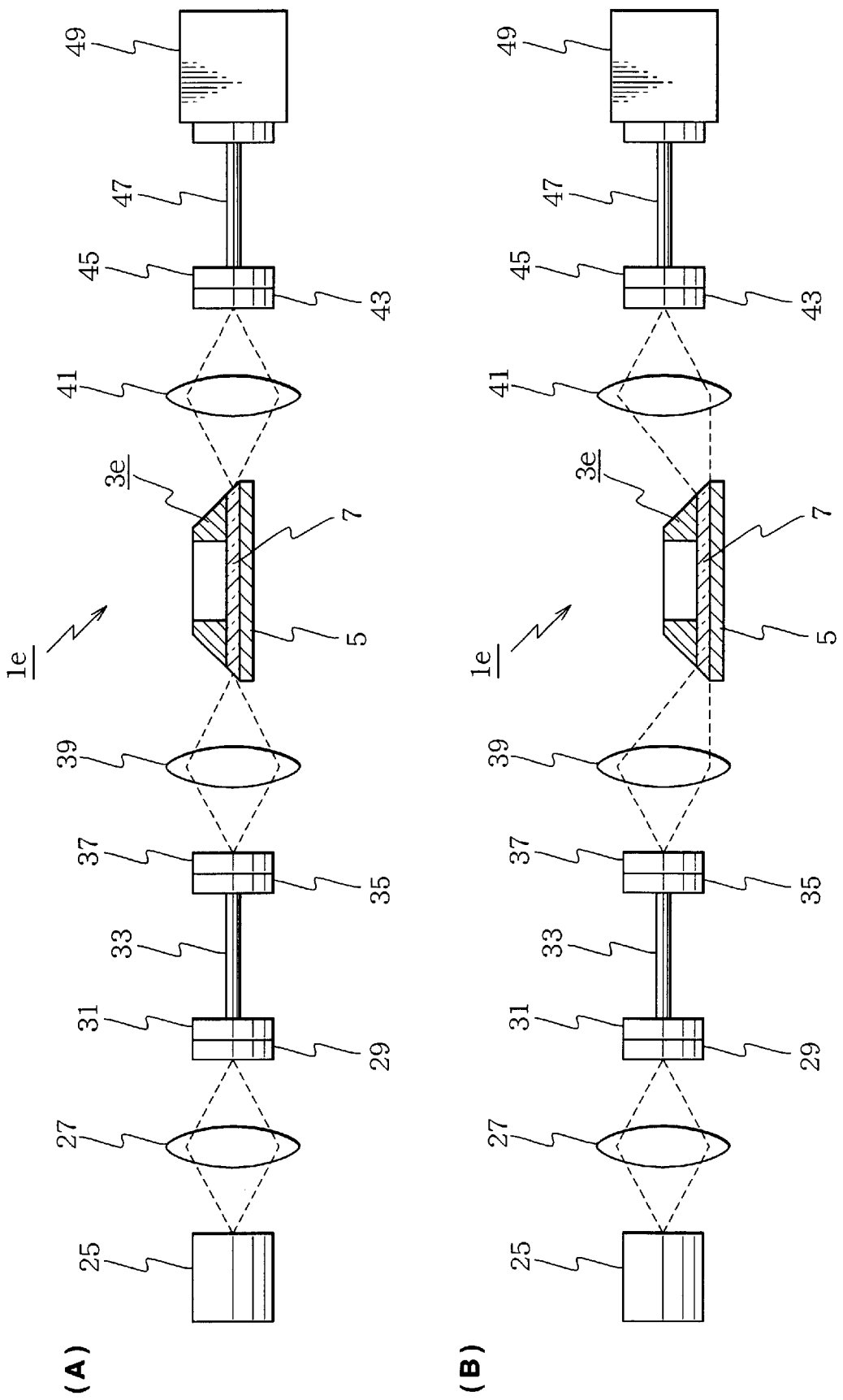
FIG. 28 shows the immunoassay apparatus disclosed in FIG. 27.

FIG. 28 also shows the entire immunoassay apparatus including the SPR sensor cell 3e shown as a cross sectional view. FIG. 28A shows a case when the light center axis from a light source is parallel to the longitudinal direction of the core. FIG. 28B shows a case when light is introduced at a predetermined angle with respect to longitudinal direction of the SPR sensor cell core.

In the case of FIG. 28B, the light L can be effectively introduced because of the inclination formed on the end surface of the core 7e. Moreover, Moreover, in this embodiment, between the light source 25 and the spectrometer 4.9, there are provided a plurality of converging lenses 27, 39, 41, an optical fiber 33, optical fiber connectors 31, 35, 45, and receptacles 29, 37, 43.

However, the present invention is not to be limited to the aforementioned configuration. It is also possible to converge the light directly from the light source 25 so that the light L is introduced into the SPR sensor cell 3e, and to converge the outgoing light L from the SPR sensor cell 3e so that the light is introduced directly into the spectrometer 49.

Furthermore, the converging lens at the upstream side of the SPR sensor cell 3e may be provided with an angle regulation mechanism (not depicted) for changing the emission angle of the light L so that the light is introduced into the core 7e at a predetermined angle as shown in FIG. 28B.

Embodiment 6

Description will now be directed to an SPR sensor cell according to a sixth embodiment of the present invention with reference to FIG. 29 to FIG. 31.

The SPR sensor cell of this embodiment includes a first clad 5f, a second clad 9f, two third clads 8f, core 7f, and a substrate 6f. The core 7f is sandwiched by the third clads 8f, forming a flat plate shape. This plate-shaped member is bonded to the first clad 5f. After bonding the third clads 8f, the core 7f, and the first clad 5f one another, these members are fixed to the substrate 6f and the second clad 9f is fixed onto the core 7f. The second clad 9f has a through hole 13f, reaching the core 7f. However, the first clad 5f may not be provided. That is, the SPR sensor cell can exhibit its function even without the first clad 5f.

In this embodiment, the first clad 5f, the second clad 9f, the third clads 8f, and the substrate 6f are made from glass of plastic.

As for the refraction factor, the core 7f has the greatest refraction factor, and the third clads 8f have the next greatest factor. The first clad 5f has a refraction factor equal to or smaller than the refraction factor of the third clads 8f. Moreover, the substrate 6f has a refraction factor equal to or smaller than the refraction factor of the first clad 5f.

FIG. 31 shows the SPR sensor cell 3f when light L is introduced into the core 7f. The light L is introduced into an end (first end) of the core 7f advances while being totally reflected in the core 7f and goes out from the other end (second end) of the core 7f.

FIG. 32 shows a modification of the second clad. This modified second clad 9f1 has a rectangular through hole and a tip fixing hole 14f formed at one corner of the rectangular hole. This tip fixing hole 14f is used for inserting a tip 81 (see FIG. 33A) for pouring and sucking a sample. The tip 81 is attached to the tip of a pipette (not depicted). The tip 81 can easily be detached from the micro-pipette.

The tip fixing hole 14f1 brings about following advantages. During pouring or suction of a sample into or from the SPR sensor cell 3f, it is possible to prevent contact of the end of the tip 81 with the antibody on the core 7f. The tip 81 is formed so as to correspond to the shape of the tip fixing hole 14f1.

FIG. 33A shows a tip 81 having an identically tapered portion L, i.e., cone shape, which corresponds to the taper of the tip fixing hole 14f2. And FIG. 33B shows a tapered tip fixing hole 14f2. The clad 9f2 has a thickness T which is greater than the tapered portion L of the tip 81. Moreover, the tip 81 has a main part having a greater diameter than the tapered portion, forming a stepped portion. This stepped portion is engaged with the surface of the second clad 9f. Thus the lower end of the tip 81 will not be brought into contact with the core 7f.

Embodiment 7

Figure 35:
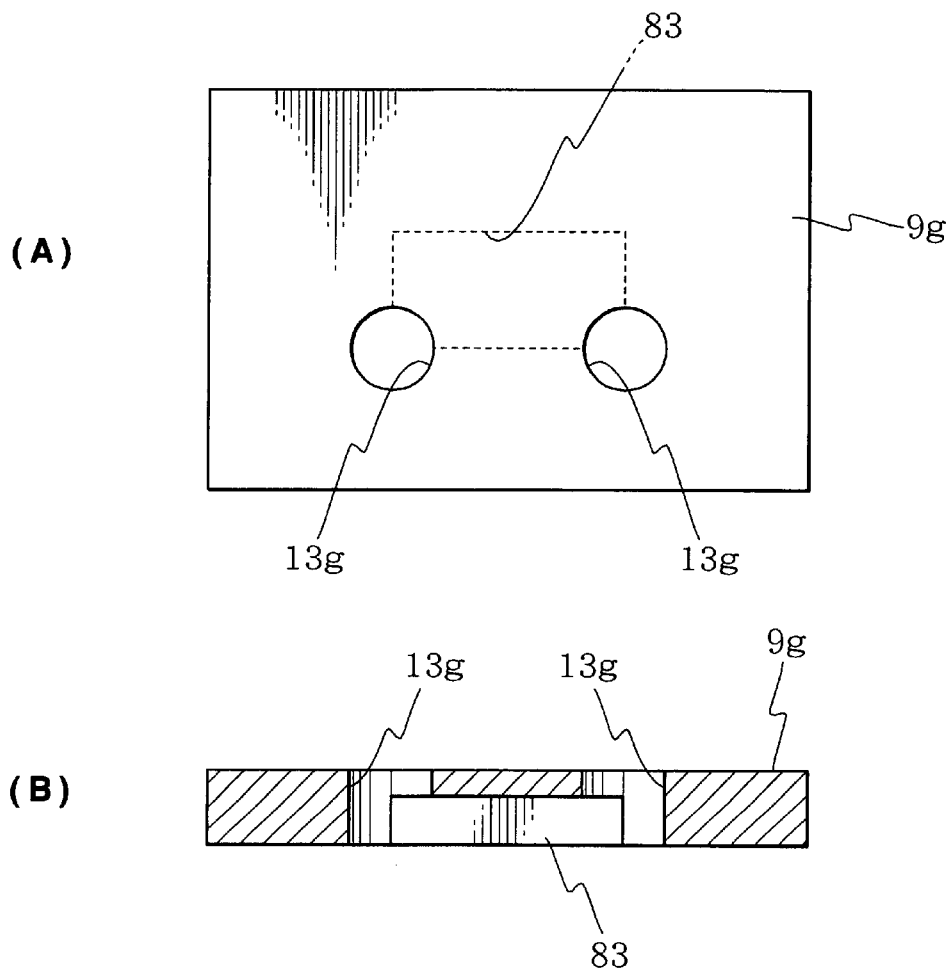
FIG. 35A is a plan view and FIG. 35B is a cross sectional view of the second clad disclosed in FIG. 34.
Figure 36:
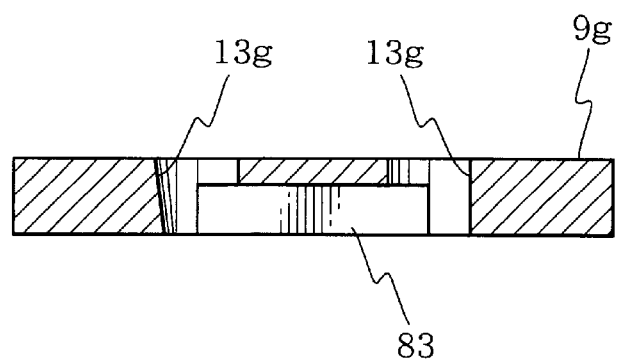
FIG. 36 is a cross sectional view of a modified example of the second clad disclosed in FIG. 35.

Description will now be directed to a seventh embodiment of the invention with reference to FIG. 34 and FIG. 35.

In the SPR sensor cell 3g according to this embodiment, the second clad 9g has two through holes 13g and a void 83 communicating with these through holes 13g. More specifically, the void 83 is formed at the bottom of the second clad 9g at a position corresponding to the core 7g of the SPR sensor cell 3g. That is, a predetermined void is defined between the second clad 9 and the core 7g. This void has a rectangular shape along the core 7g and serves as a reservoir of a sample during an immunoassay. Note that the void 83 may have any shape if formed at a position corresponding to the core 7g.

Moreover, one of the through holes 13g is used for pouring a sample into the void 83 or for sucking the sample. That is, the tip 81 of a micro-pipette (see FIG. 33A) is inserted into one of the holes 13g, leaving the other hole 13g for going out of air. This is because the void is a closed portion excluding the two through holes 13g. Thus, when the void is provided in the second clad 9g, there is no danger of a sample leak. Moreover, when attaching the SPR sensor cell 3g to the immunoassay apparatus or detaching the SPR sensor cell 3g from the immunoassay apparatus, there is no danger of sample leak.

In the aforementioned embodiment, each of the through holes 13g has a cylindrical shape. However, the present invention is not to be limited to the cylindrical shape. One or both of the through holes 13g may also have a tapered shape, i.e., cone shape corresponding to the configuration of the tip 81 of the micro-pipette.

Embodiment 8

Figure 37:
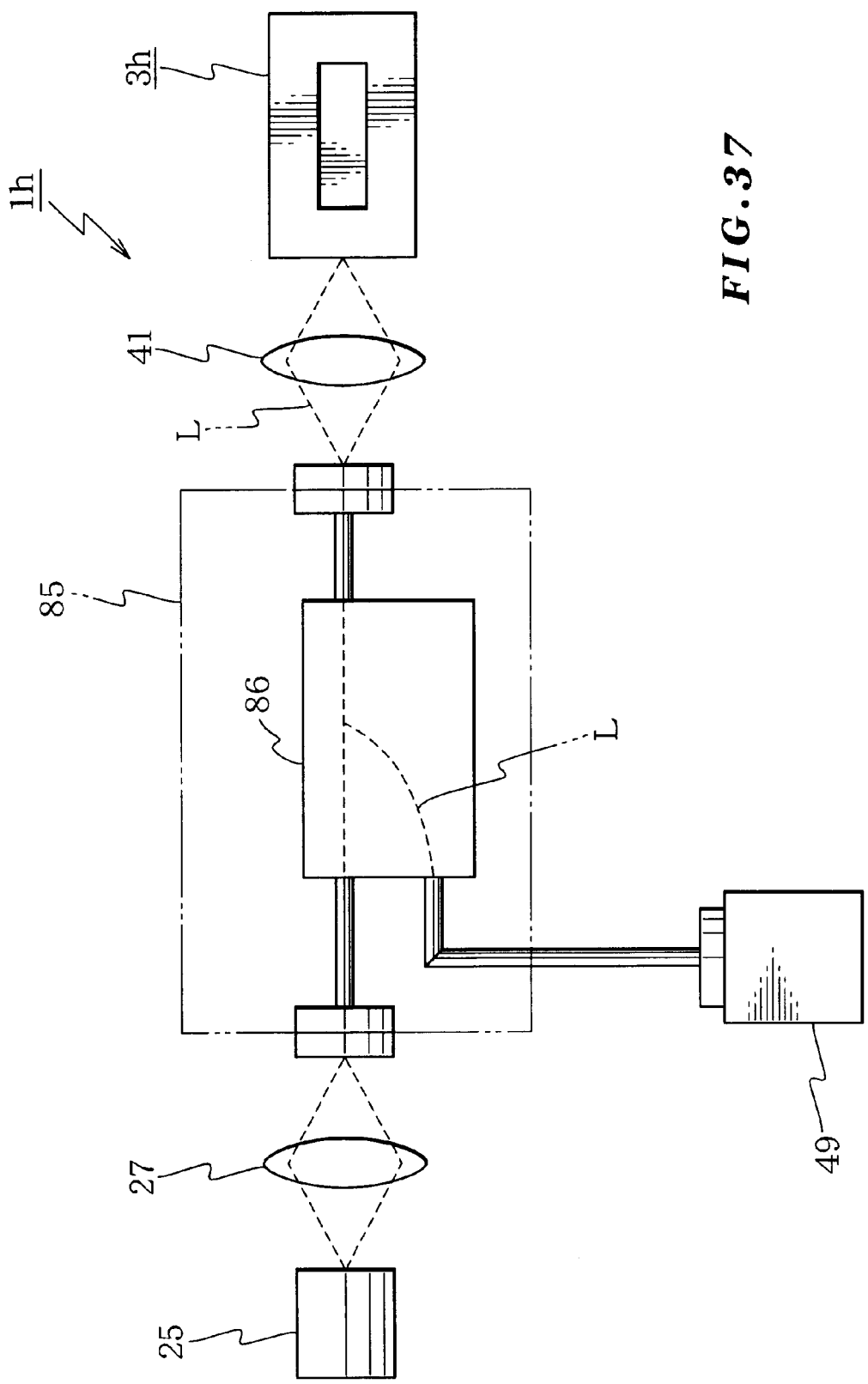
FIG. 37 is a plan view of an immunoassay apparatus according to an eighth embodiment of the present invention.

FIG. 37 shows an entire configuration of an immunoassay apparatus 1h according to an eighth embodiment of the present invention. In this embodiment, an optical coupler 85 is used for branching the light from the light source 25 into an optical path for the SPR sensor cell 3h and an optical path from the SPR sensor cell 3h to the spectrometer 49. That is, the light L from the light source 25 is introduced through the converging lens 27 into the optical coupler 85. In the optical coupler 85, the light advances to the side of the SPR sensor cell 3h. The light L further advances through the converging lens 41 to the SPR sensor cell 3h.

The light L into one end (first end) of the SPR sensor cell 3h advances in the core while repeating total reflection and reaches the other end (second end) of the core. The second end of the core has a thin metal film of Ag, serving as a reflection surface of the light L. Accordingly, the light L which has passed through the core causes a surface plasmon resonance and then is reflected by the reflection surface of the core to return through the core and emitted from the first end of the SPR sensor cell. Here, the returning light L also causes a surface plasmon to attenuate a particular wavelength of the light L. This improves the sensitivity of the SPR sensor.

The light L emitted from the first end of the SPR sensor cell 3h passes through the converging lens 41 and advances into the optical coupler 85. The light L from the SPR sensor is branched by a branching block 86 of the optical coupler 85 to the path leading to the spectrometer 86. The light L is subjected to a wavelength distribution analysis by the spectrometer connected to the optical coupler 85.

Figure 38:
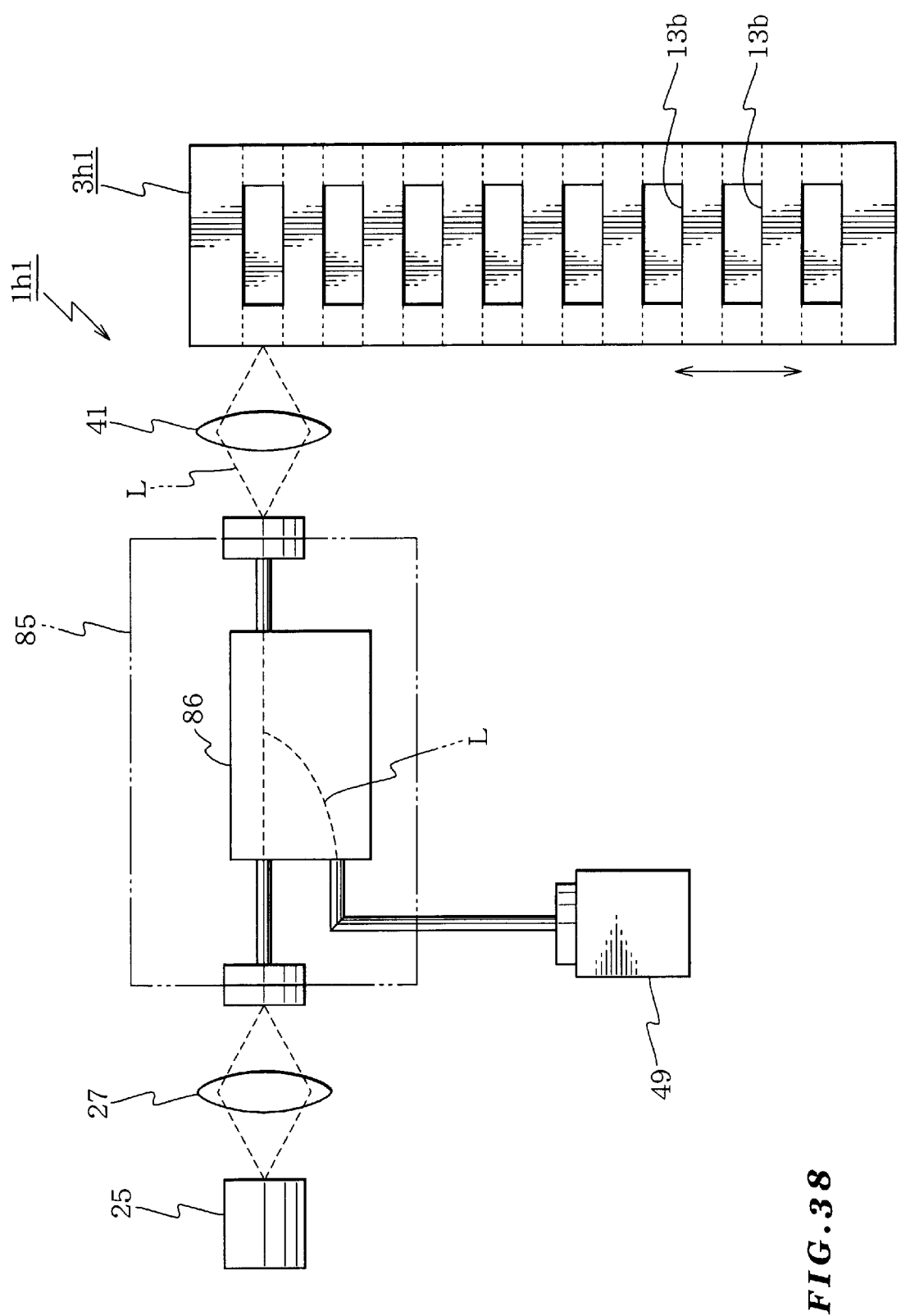
FIG. 38 is a plan view of a modified example of the immunoassay apparatus disclosed in FIG. 37.

FIG. 38 shows an example of the immunoassay apparatus 1h1 having a plurality of cores in the SPR sensor 3h1. As shown in FIG. 38, the SPR sensor cell 3h1 has eight cores. When carrying out immunoassay, the SPR sensor cell 3h1 is positioned at one of the eight cores so that the core is matched with an optical path of the light L from the light source. For a subsequent immunoassay, the position of the SPR sensor cell is shifted.

Thus, shifting the position of the SPR sensor cell 3h, it is possible to successively and rapidly perform the immunoassay for a plurality of samples. Moreover, if different antibodies are fixed for the respective cores, it is possible to rapidly perform the immunoassay of various types of antigens in a single sample. And also, it is possible to rapidly perform the immunoassay of prescribed antigens in a various samples. Note that the number of cores is not to be limited to a particular number.

The aforementioned coupler 85 may be any one of the various types available, such as melting type, electro-optical effect type, temperature regulating type, and stress regulating type.

The melting type is an optical coupler in which two optical waveguides are melted to be collected into a single waveguide.

The electro-optical type is an optical coupler in which voltage is applied to an electro-optical crystal so as to change the wavelength characteristic. This enables to selecct an optical waveguide and determine a dividing ratio of the light L passing through the optical waveguide.

The temperature-regulating type is an optical coupler in which a connected portion between a plurality of optical waveguides is surrounded silicone and a Peltier element is used to regulate the temperature, thus changing the wavelength characteristic.

The stress regulating type is an optical coupler in which the optical waveguide is subjected to twisting and bending so as to change the wavelength characteristic.

Embodiment 9

Figure 39:
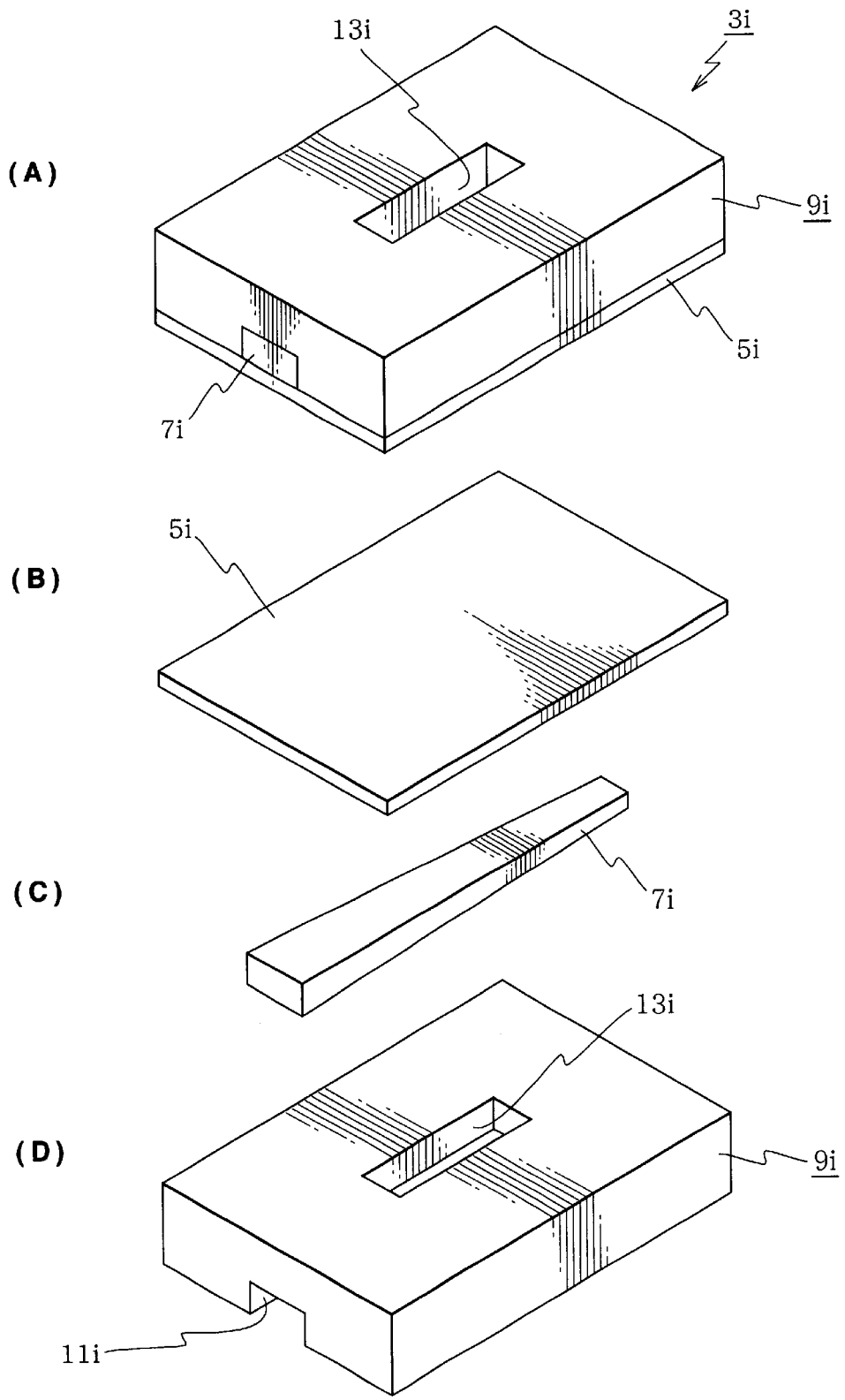
FIG. 39 shows an SPR sensor cell according to a ninth embodiment of the present invention.

FIG. 39 shows an SPR sensor cell 3i used in an immunoassay apparatus according to the ninth embodiment of the present invention.

This SPR sensor cell 3i is characterized by the configuration of the core 7i. That is, as shown in FIG. 39C, the first end (the incident side) and the second end (outgoing side) of the core have different cross sectional areas. In the case of FIG. 39, the first end surface has a greater area than the second end surface, and both of the first and the second end have rectangular cross section.

Thus, when the second end has a smaller cross section than that of the first end of the core 7i, the light L is converted when going out. That is, the light L can be effectively introduced into the spectrometer 49 or the like. Note that the core cross section is not to be limited to a rectangle but also may be a circle, triangle, or other shapes.

FIG. 39A is a perspective view of the SPR sensor cell 3i comprising the components shown in FIG. 39B, FIG. 39C, and FIG. 39D. That is, the SPR sensor cell 3i comprises a first clad 5i made from glass or plastic; a core 7i provided on this first clad 5i; and a second clad 9i to cover the core 7i and the first clad 5i. The second clad 9i has an indentation 11i at its bottom. The first clad 5i, the core 7i, and the second clad 9i are connected to one another using a predetermined adhesive.

These components have different refraction factors. That is, the core 7i is made from a material having the greatest refraction factor. The second clad 9i is made from a material having the next greatest factor. The first clad 5i is made from a material having a refraction factor equal to or smaller than that of the second clad 9i.

Embodiment 10

FIG. 40 shows a configuration of the tenth embodiment. FIG. 40A is a perspective view of a sensor cell fixing table 87. FIG. 40B is a perspective view of an SPR sensor cell 3j fixed on the sensor cell fixing table 87.

The SPR sensor cell 3j according to this embodiment has a plurality of cores 7j and the second clad 9j has a single through hole exposing all of the cores 7j. Accordingly, if different antibodies are fixed to the surface of the cores 7j via a thin metal film and a dielectric film, and a single sample is poured into the through hole 13j, it is possible to quickly perform immunoassays for various antigens contained in the sample. And also, it is possible to rapidly perform the immunoassay of prescribed antigens in a various samples.

Embodiment 11

Description will now be directed to an eleventh embodiment with reference to the attached drawings.

Firstly, referring to FIG. 41 and FIG. 42, explanation will be given on a SPR sensor cell B3 according to the Embodiment 11. Here, FIG. 42A is a cross sectional view of the SPR sensor cell viewed about the line X—X in FIG. 41A.

The SPR sensor cell B3 of Embodiment 11 uses an optical waveguide. More specifically, the SPR sensor B3 comprises:

a sheet-shaped first clad (substrate) B5; two cores B7a and B7b provided on this first clad B5; and a second clad (upper layer sheet) B9 covering the cores B7a and B7b as well as the surface of the first clad B5. It should be noted that there are various types available such as a planer type, a strip type, an embedded type, and a lens type.

The first clad B5 is a thin sheet or plate made from a glass or the like. The two cores B7a and B7b are mounted on this first clad, for transmitting light. The cores B7a and B7b are made from glass or plastic and extend over the total length of the SPR sensor cell B3.

Moreover, the second clad B9 is arranged over the cores B7a and B7b and the exposed surface of the first clad B5. More specifically, the second clad B9 has two grooves B11a and B11b on its bottom so as to correspond to the cores B7a and B7b. When the second clad B9 is arranged on the first clad B5, the cores B7a and B7b are engaged with the grooves B11a and B11b while the bottom of the second clad B9 is brought into abutment with the surface of the first clad B5.

The cores B7a and B7b may be attached to the first clad B5 using an adhesive or by way of heating for melting the boundary surfaces between the first clad B5 and cores B7a and B7b. This also applies to the mounting of the second clad B9 on the first clad B5. When an adhesive is used, light attenuation by the adhesive should be considered, and it is necessary to use an adhesive having a lower refraction factor than the refraction factor of the cores B7a and B7b.

Moreover, a through hole B13 is formed in the center portion of the second clad B9. More specifically, the through hole extends from the upper surface of the second clad B9 to the intermediate portion sandwiched by the two cores B7a and B7b. That is, the cores B7a and B7b are arranged at a predetermined distance and parallel to each other. The through hole B13 has a width almost identical to the distance between the B7a and B7b. Accordingly, the cores B7a and B7b have surface portions exposed to this through hole B13. As will be detailed later, those surfaces are covered with a thin metal film, thus constituting an SPR sensing portion B8.

It should be noted that the through hole B13 can be formed in a sheet-type second clad B9 on which two grooves B11a and B11b have been formed. That is, the through hole B13 is formed at a position between the grooves.

As the second clad B9 is formed as has been described above, a rectangular parallelopiped space is defined by the through hole B13, the two cores B7a and B7b and the surface of the first clad B5. This space serves as a sample reservoir B14 for immunoassay.

Here, the first clad B5, the two cores B7a and B7b, and the second clad B9 should have refraction factors in a predetermined relationship, so that the cores B7a and B7b function as optical waveguides.

More specifically, the cores B7a and B7b should have a greatest refraction factor, and the second clad B9 should have a second greatest refraction factor. The refraction factor of the first clad 5B may be equal to or smaller than the refraction factor of the second clad B9.

This can be expressed as follows:

$$N2>N1=N4 \text{ or } N2>N4 \text{ and } N2>N1$$

wherein N1 is the refraction factor of the first clad B5, N2 is the refraction factor of the cores B7a and B7b, and N4 is the refraction factor of the second clad B9.

Description will now be directed to the sample reservoir B14, serving as the SPR sensor (SPR sensing portion B8).

FIG. 42A is a cross sectional view of the through hole, and FIG. 42B is an enlarged cross sectional view. As shown in FIG. 42B, the surface of the core is covered with a thin metal film B15 and a dielectric film 17 in this order, and an antibody (or antigen) is fixed to the surface of the dielectric film B17.

More specifically, the thin metal film B15 is formed from Au by way of deposition or the like, so as to constitute the SPR sensing portion. Note that instead of Au, Ag can also be used to constitute the SPR sensor portion. Here, in the case of the core B7b made from glass and the thin metal film B15 formed from Au, it is recommended to coat the surface of the core B7b with chrome (Cr) of several nm thickness. When the chrome film is present, the Au coating can be made more stable.

Next, an antibody (or antigen) is fixed via the dielectric film B17 on the thin metal film of Au. This antibody (or antigen) B19 is selected in accordance with an antigen (or antibody) contained in a sample for immunoassay, which enables to decide whether a particular antigen is contained in the sample.

Next, explanation will be given on the SPR sensor cell B3. Firstly, a sample containing a predetermined antigen is introduced into the sample reservoir B14 of the SPR sensor cell B3. If the sample contains an antigen specifically reacts to the antibody B19 fixed on to the dielectric film B17, an immune reaction is caused. This immune reaction changes the light wavelength generating a surface plasmon resonance.

Consequently, a wavelength distribution of the light coming out of the cores B7a and B7b after the immune reaction is different from the wavelength distribution when no immune reaction is caused. More specifically, a particular wavelength causing a surface plasmon resonance is attenuated. Therefore, by identifying the wavelength attenuated, it is possible to carry out an immunoassay.

Embodiment 12

Figure 43:
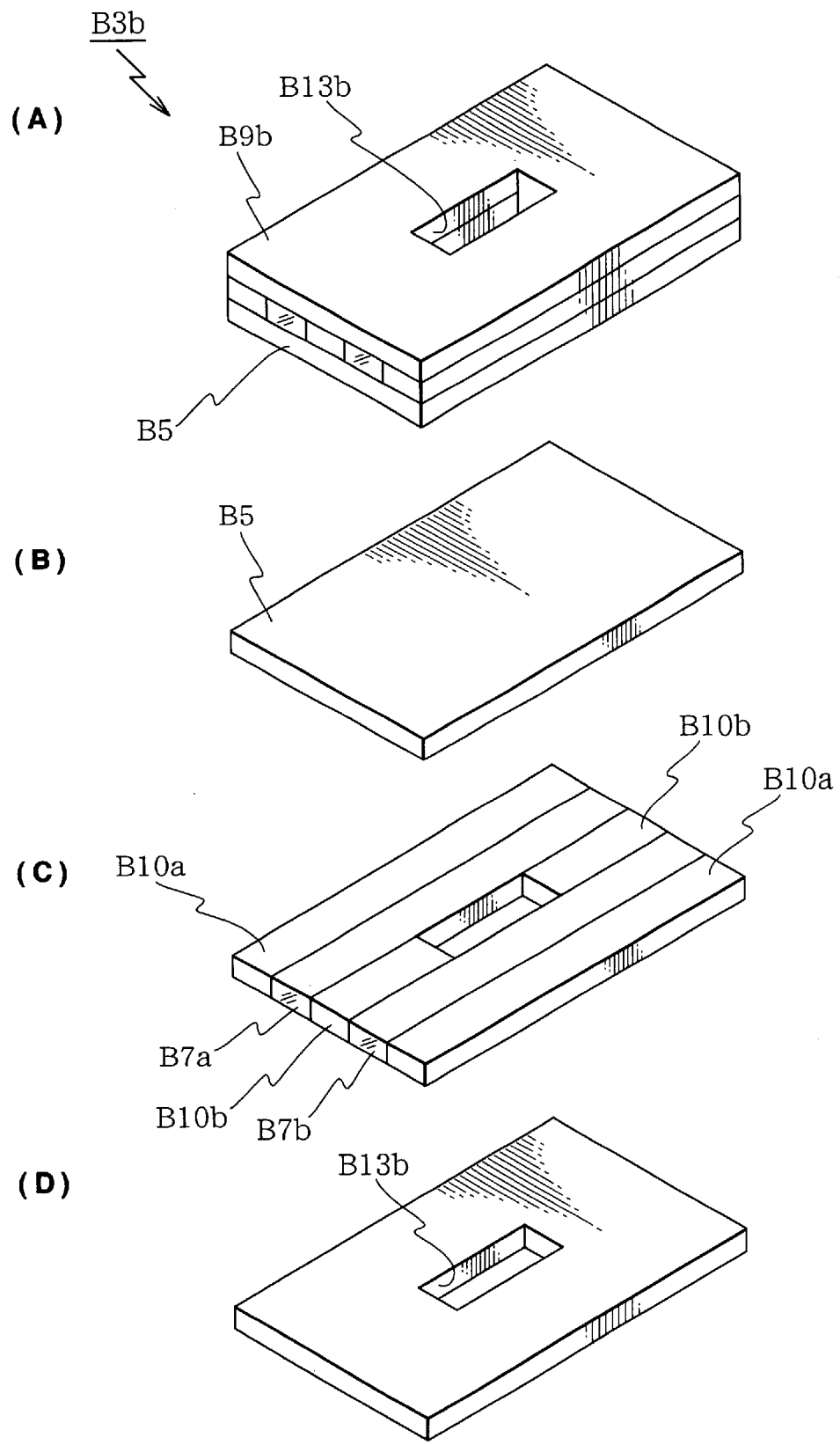
FIG. 43 is a perspective view an SPR sensor cell according to Embodiment 12.

FIG. 43 is a perspective view of an SPR sensor cell B3b according to a twelfth embodiment of the present invention. Here, like components as in the Embodiment 11 are denoted by like reference symbols.

The SPR sensor cell B3b has a basic configuration identical to the eleventh embodiment except for that the SPR sensor cell B3b is formed by three layers instead of two layers.

As shown in FIG. 43B, the first clad B5 is a sheet-shaped member like in the eleventh embodiment. The second, i.e. intermediate layer containing the cores B7a and B7b is constituted by combination a plurality of clads.

Here the cores B7a and B7b having an identical length and thickness are arranged in parallel to each other while sandwiching two shorter clads B10b arranged in the length direction and the cores B7a and B7b themselves are sandwiched by longer clads B10a. The total length of the two shorter clads B10b is smaller than each of the longer clads B10a, so as to obtain a vacant center portion between the two shorter clads B10b. That is, there is no shorter clads at the center portion of the cores B7a and B7b.

This vacant space, i.e., this void serves as a sample reservoir, constituting the SPR sensing portion. The sample reservoir has a length equal to a difference between the longer clad B7a or B7b and the total length of the two shorter clads B10b. Note that the thickness of the shorter clads B10b is identical to that of the cores B7a and B7b.

As for the longer clads B10a, each has a length identical to that of the core B7a or B7b, and a thickness identical to that of the cores B7a and B7b. Thus, the combination of the cores B7a and B7b, the shorter clads B10b, and the longer clads B10a constitutes a sheet-shaped member as the second layeer having a predetermined thickness. Moreover, the width of this sheet-shaped member is identical to the width of the aforementioned first clad B5. Note that the short clads B10b and the longer clads B10a have a refraction factor equivalent to that of the second clad B9.

Furthermore, the third layer is constituted by the second clad B9b, which is a sheet-shaped member having a constant thickness and a through hole B13b at the center thereof. The length of this through hole corresponds to the sample reservoir and almost identical to the distance between the shorter clads B10b. Moreover, this second clad B9b has a width identical to that of the first clad B5. Note that, location of the through hole B13b may be other than the center portion if it corresponds to the sample reservoir.

As has been described above, the SPR sensor cell B3b according to the eleventh embodiment is constituted by three layers: the first layer constituted by the first clad B5, the second layer constituted by cores B7a, B7b, and longer and shorter clads; and the third layer constituted by the second clad. These members may be attached to each other using an adhesive or oil. Thus, in this embodiment, the second layer and the third layer are separately formed. Accordingly, there is no need of forming grooves B11a, B11b (see FIG. 41), thus facilitating to prepare the SPR sensor cell.

Embodiment 13

Referring to FIG. 44, explanation will be given on a thirteenth embodiment. In this embodiment, the second clad B9b is prepared by a method different from that of the Embodiment 12. As shown in FIG. 44A and FIG. 44B, the second clad B9c1 and B9c2 are respectively constituted by four members.

Firstly, as shown in FIG. 44A, the second clad B9c1 is constituted by two shorter clads B9c11 arranged so as to sandwich the through hole B13c1 in the longitudinal direction and two longer clads B9c12 arranged so as to sandwich the through hole B13c1 in the width direction.

Each of the two shorter clads B9c11 has a length smaller than the half of the core length and is arranged at a predetermined distance from each other. This distance defines the length of the through hole B13c1.

Moreover, each of the two longer clads B9c12 has a length identical to that of the cores and arranged so as to sandwich the shorter clads B9c11. That is, the through hole B13c1 is defined by the two shorter clads B9c11 and the two longer clads B9c12. These clads have an identical thickness and they constitute a sheet-shaped clad when they are attached to one another.

FIG. 44B shows a modified example of FIG. 44A. The second clad B9c2 is constituted by shorter clads B9c21 arranged so as to sandwich the through hole B13c2 in the width direction and two longer clads B9c22 arranged so as to sandwich the through hole B13c2 and the shorter clads B9c21 in the longitudinal direction.

Each of the shorter clads B9c21 has a length identical to that of the through hole B13c2 and arranged at a predetermined distance which defines the width of the through hole B13c2.

Moreover, each of the longer clads B9c22 has a length equal to the width of the SPR sensor cell and is arranged so as to sandwich the shorter clads B9c21 from both sides. That is, the through hold B13c2 is defined by the two shorter clads B9c21 and the two longer clads B9c22. These clads all have an identical thickness and become a plain sheet when attached to one another.

Thus, by combining a plurality of members having an identical thickness, it is possible to easily obtain the second clad B9c1 or B9c2 respectively having the through hole B13c1 or B13c2. This eliminates a difficult and troublesome work for forming a through hole in a sheet-shaped clad.

Embodiment 14

Referring to FIG. 45, explanation will be given on a fourteenth embodiment, wherein the second clad B9d of the eleventh embodiment is made in a different way. That is, the second clad B9d is constituted by six members having different thickness values. The two cores B7a and B7b and the first clad B5 are identical to those of the Embodiment 11.

In this embodiment, firstly, the through hole B13d is defined: by two shorter clads B9d1 which are arranged in their length direction (in series) at a distance corresponding to the length of the through hole B13d; and intermediate clads B9d2, each having a length almost identical to the cores B7a and B7b and arranged to sandwich the shorter clads B9d1. Thus, the through hole B13d is defined by the shorter clads B9d1 and the intermediate clads B9d2.

Here the shorter clads B9d1 and the intermediate dads B9d2 have different thickness values. That is, each of the intermediate clads B9d2 has a thickness smaller than that of the shorter clads B9d1 by a value corresponding to the thickness of the cores B7a an d B7b. That is, when the c ores B7a and B7b are angaged with the intermediate clads B9d2, the total thickness is identical to the thickness of the shorter clads B9d1.

Moreover, the intermediate clads B9d2 are sandwiched are sandwiched by longer clads B9d3 having a length almost identical to the length of the cores B7a and B7b and a thickness identical to the thickness of the shorter clads B9d1.

Accordingly, when the cores B7a and B7b, the shorter clads B9d1, the intermediate clads B9d2, and the longer B9d3 are all attached to one another, it is possible to obtain a sheet-shaped member having a predetermined thickness. By attaching this sheet-shaped member to the first clad B5, it is possible to obtain an SPR sensor cell like the SPR sensor of Embodiment 11.

This embodiment increases the steps of attachment but does not need the formation of the grooves B11a, B11b, or the formation of the through hole B13. Especially if the clads are made from glass, cracks may be caused when forming the grooves B11a, B11b and the through hole B13, thus lowering the production yield. On the other hand the SPR sensor cell according to the present embodiment has no such problem.

Embodiment 15

Figure 46:
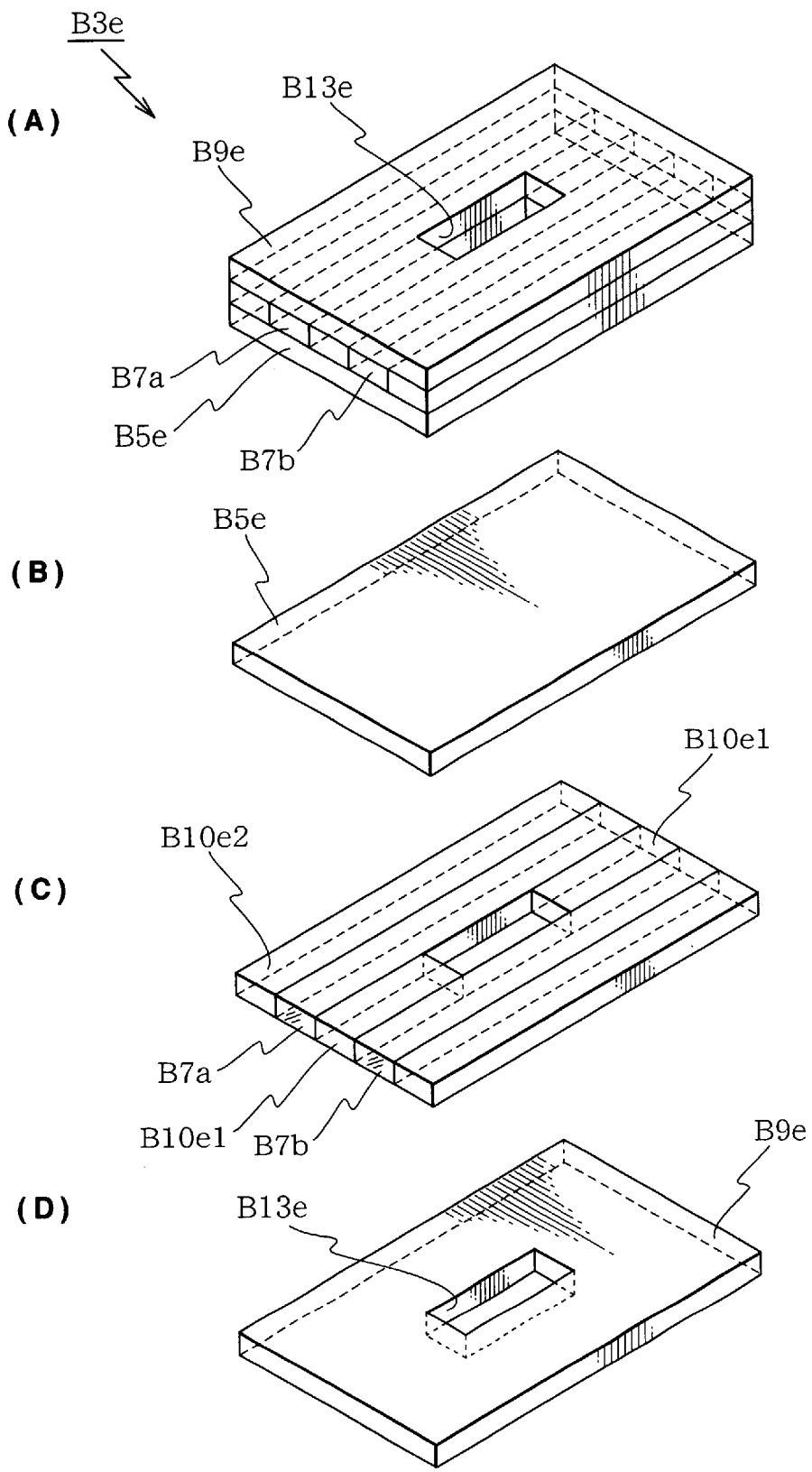
FIG. 46 shows a configuration of an SPR sensor cell according to Embodiment 15.

Referring to FIG. 46, explanation will be given on a fifteenth embodiment.

Embodiment 15 has a configuration identical to Embodiment 12 except for that the first clad B5e and the second clad B9e including the shorter clads B10e1 and the longer clads B10e2 all have end surfaces obscured, or covered by aluminum (Al) coating, or painted with a black paint.

When one of these processes is performed, it becomes difficult for light to pass through these end surfaces, and the light is introduced only into the cores B7a, B7b. If the light passes through other than the cores B7a, B7b, the light may come into the cores B7a and B7b, which may lower the immunoassay accuracy (sensitivity).

The light-passing inhibiting process may be other than those aforementioned. For example, it is also possible to attach a plate-shaped member (made from rubber or plastic for example) to the end surfaces of the clads. The material may be anything if it makes light-passing difficult.

Figure 47:
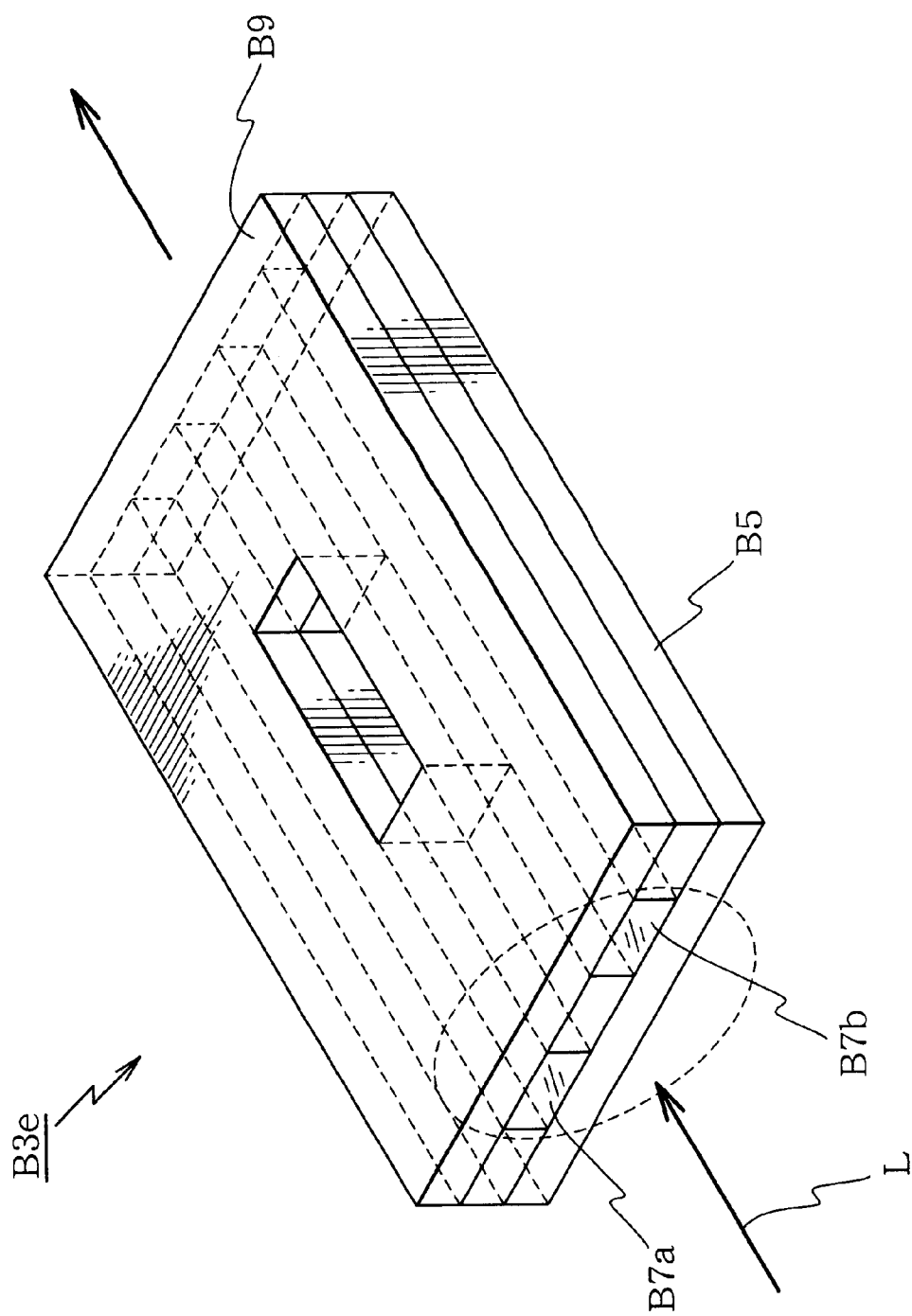
FIG. 47 shows the SPR sensor of FIG. 46 in a state when light is introduced.

FIG. 47 shows the SPR sensor cell B3e according to this embodiment when light is introduced for immunoassay. This SPR sensor cell has two cores B7a and B7b, and the light is introduced simultaneously into two of the cores B7a and B7b (as shown by a dotted line of ellipse).

When the light is simultaneously introduced into the two cores B7a, B7b, it is possible to use only optical system including a light source and a converging lens. If an antibody is fixed to each of the cores B7a, B7b, it is possible to improve the immunoassay accuracy (sensitivity). Moreover, if different antibodies are fixed in the cores B7a and B7b, it is possible to simultaneously perform a sample immunoassay for different antigens.

Moreover, it is possible to successively introduce light in the core B7a and B7b, thus enabling to perform two immunoassay processes for one sample. Alternatively, it is possible one or the cores as a reference.

Furthermore, immunoassay results can be obtained as a change in wavelength distribution of the light coming out from the SPR sensor cell. For example, when an antibody is fixed in both of the cores B7a and B7b, the light emitted from these cores B7a and B7b is collected into one to be subjected to wavelength distribution analysis using one spectrometer. On the other hand, when different antibodies are fixed in the cores B7a and B7b, it is necessary to perform immunoassay separately from each other. In this case, the optical waveguide is switched between the cores B7a and B7b and wavelength distribution is determined using one spectrometer.

Moreover, if it is possible to use a plurality of spectrometers, they can be arranged corresponding to the cores B7a and B7b, respectively. Thus, it is possible to simultaneously perform an immunoassay for each of the cores B7a and B7b.

Embodiment 16

Figure 48:
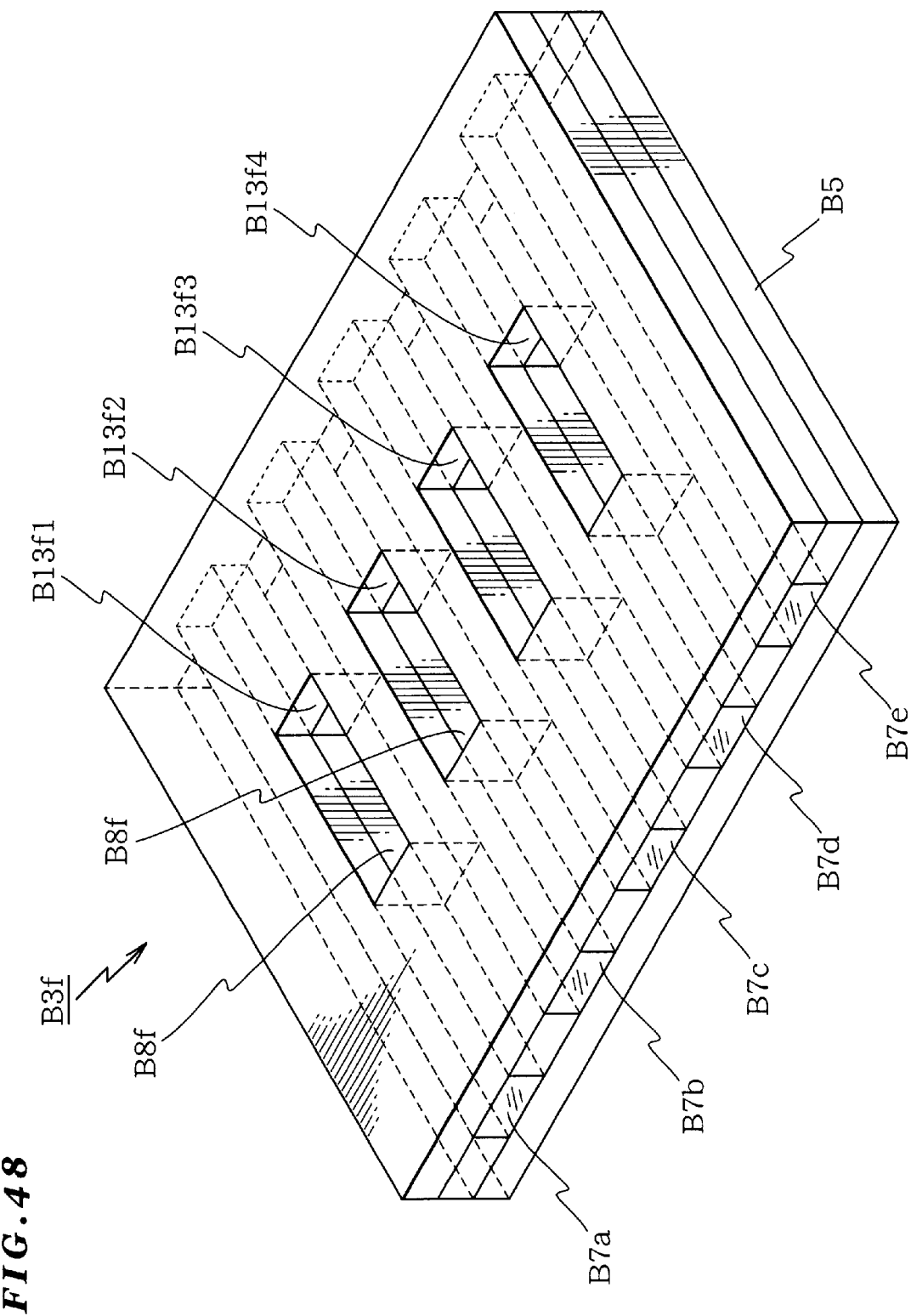
FIG. 48 is a perspective view of an SPR sensor cell according to Embodiment 16 having a plurality of cores and a plurality of through holes.

FIG. 48 is a perspective view of an SPR sensor cell according to a sixteenth embodiment of the present invention. This embodiment is characterized in that there are provided five cores B7a to B7e and four through holes B13f1 to B13f4. That is, the through hole B13f1 is formed between the adjacent cores B7a and B7b, and the through hole B13f2 is formed between the cores B7b and B7c. Thus, the five cores B7a to B7e alternate with the four through holes B13f1 to B13f4.

This configuration of the SPR sensor cell has an advantage as follows. A part of the surface of the core B7a exposed to the through hole B13f1 serves as an SPR sensing portion. Similarly, a part of the surface of the ore B7b exposed to the through hole B13f1 also serves as an SPR sensing portion. In addition to this, apart of the surface of the core B7b exposed to the through hole B13f2 also serves as an SPR sensing portion. The same applies to the other holes and cores.

In this embodiment, the five cores B7a to B7e and the four through holes B13f constitute quasi-eight SPR sensing portions. Note that although each core has an SPR sensing portion at two sides, the light coming from the core is subjected a wavelength distribution analysis by one spectrometer. Actually, it is impossible to simultaneously perform eight immunoassays. It can be considered to fix one and the same antibody to the SPR sensing portions of a single core, so as to improve the immunoassay accuracy.

In this embodiment, the number of through holes is smaller by one than the number of cores. However, the present invention is not to be limited to such a configuration. That is, the number of through holes may be greater than the number of the cores by one. For example, if there are provided five cores and six through holes. Two sides of each core, i.e., 10 sides can be used as the SPR sensing portions.

Moreover, the number of cores is not to be limited to five, but may be three, four, or six or more. Note that it is also possible to further provide cores under the through holes. That is, by exposing three cores to each of the through holes, it is possible to perform a number of immunoassays.

It should be noted that in the aforementioned Embodiments 11 to 16, the light introduced into the SPR sensor cell for immunoassay is emitted out from the opposite side of the SPR sensor cell. However, the present invention is not to be limited to such a configuration. For example, it is possible to cover the opposite end (second end) of the core with a thin metal film made from Ag or the like by deposition, so that the second end of the core is used as a reflection surface of the light. When the second end has a reflection surface, the light introduced from one end (first end) causes the surface plasmon resonance at the center portion of the core and the light is reflected by the thin metal film 61 of the second end.

By analyzing the light reflected by the thin metal film at the second end, it is possible to identify a particular wavelength whose intensity has been lowered. When the thin metal film is present, so as to reflect the light, the light intensity is further lowered because the light causes a surface plasmon resonance not only when reaching the second end but also when coming back from the second end. Thus, the SPR sensor cell substantially improves its sensitivity.

Embodiment 17

Figure 49:
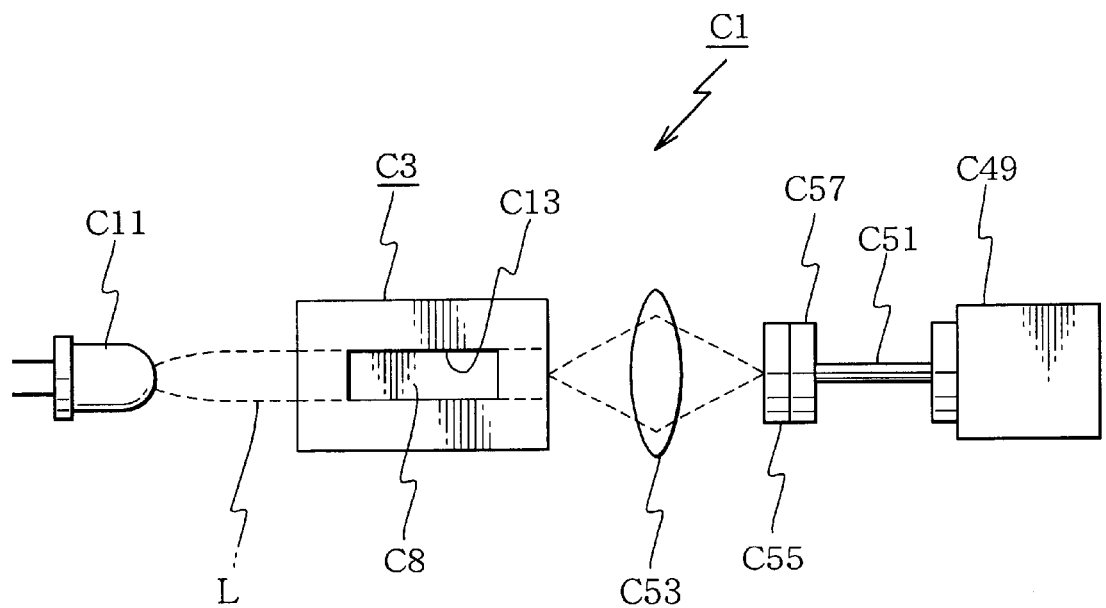
FIG. 49 schematically shows an entire configuration of an immunoassay apparatus according to Embodiment 17.

Description will now be directed to Embodiment 17 with reference to FIG. 49.

FIG. 49 shows an entire configuration of an immunoassay apparatus C1, which comprises: a white LED lamp as a light source C11; an SPR sensor cell C3 for introducing light so as to generate a surface plasmon resonance (SPR); and light analyzing means C49. These components will be detailed below.

Firstly, explanation will be given on the light source C11 for emitting light L for immunoassay. The light source C11 is a white LED lamp for emitting the light L having a predetermined wavelength distribution. The immunoassay apparatus C1 according to the present embodiment of the invention analyzes a light wavelength distribution change before and after an immune reaction so as to identify the immune reaction. Accordingly, it is preferable that the light source C11 can emit light L having a stable wavelength distribution. The white LED lamp on market normally has a wavelength in the order from 450 nm to 750 nm. Note that the light source C11 may be other than the aforementioned white LED lamp if it can emit light of a predetermined wavelength.

Figure 50:
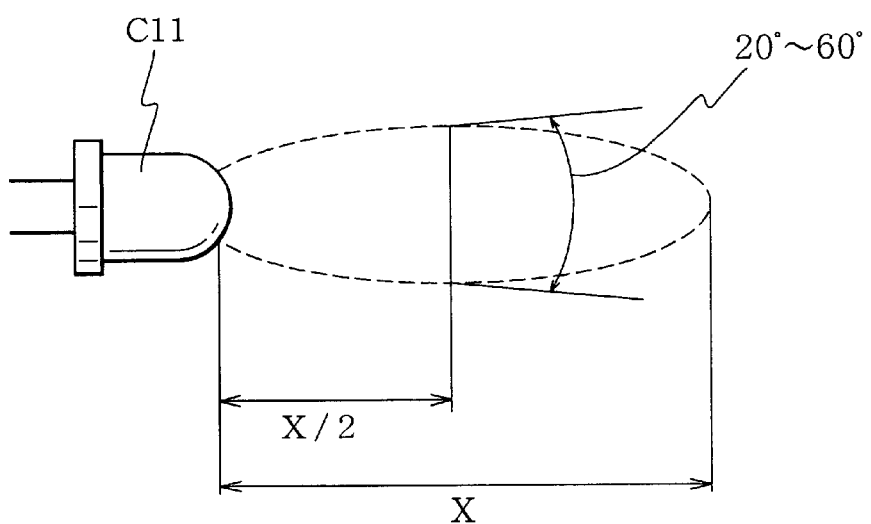
FIG. 50 shows a light source (white LED lamp) used in the immunoassay apparatus of FIG. 49.

FIG. 50 shows a directivity (light emission angle) of the white LED lamp which is 20 to 60 degrees. This is different from a halogen lamp having an emission angle of 180 degrees or more. Here, the emission angle is determined at an intermediate point in the emission direction of a portion having a predetermined luminance. When using the light source C11 having a high directivity, a converging lens which will be detailed later may not be needed. It should be noted that there is also a white LED lamp having an emission angle in the order of 140 degrees. Such a white LED lamp can be used when applying the light L to a plurality of cores of the SPR sensor cell C3.

When using a white LED lamp, the cost is about 1/10 of a halogen lamp, and power consumption is about 1/30 of the halogen lamp. The drive voltage of the white LED lamp is also sufficiently low enabling to use a battery. It is also possible to reduce the entire size of the immunoassay apparatus.

In the light analyzing means C49 shown in FIG. 49 analyzes a wavelength distribution of the incident light L. More specifically, a wavelength distribution prior to an immunoassay is checked beforehand. That is, a wavelength distribution is measured with no sample (or a sample containing no antigen) in the sample reservoir. Next, a sample to be measured is introduced into the sample reservoir 14 to cause an immune reaction. After this, the wavelength distribution after the immune reaction is checked.

According to a difference between the wavelength distributions before and after the immune reaction, it is possible to decide whether an immune reaction has been actually present or to determine the immune reaction state.

For the actual determination of the wavelength distribution, a spectrometer is used.

Moreover, instead of using a spectrometer, it is also possible to use a photo diode. in this case, a filter is mounted to pass a particular wavelength assumed to be attenuated by the immunoassay. Alternatively, it is also possible to provide a plurality of photo diodes and filters for the respective photo diodes so as to pass light of different wavelength, so that attenuation of each of the wavelengths can be determined for an immunoassay.

FIG. 51 is a perspective view of modified examples of the SPR sensor cell. These sensor cells C3C and C3D are subjected to a surface processing excluding the end surfaces of the cores C7 and C7a. More specifically, the first clad, the second clad, and the intermediate clad have end surfaces processed so that light cannot pass through. For example, the end surfaces are processed to be obscured by sand blast or the like, or covered with an aluminum (Al) coating, ore painted with a black paint.

Embodiment 18

Figure 52:
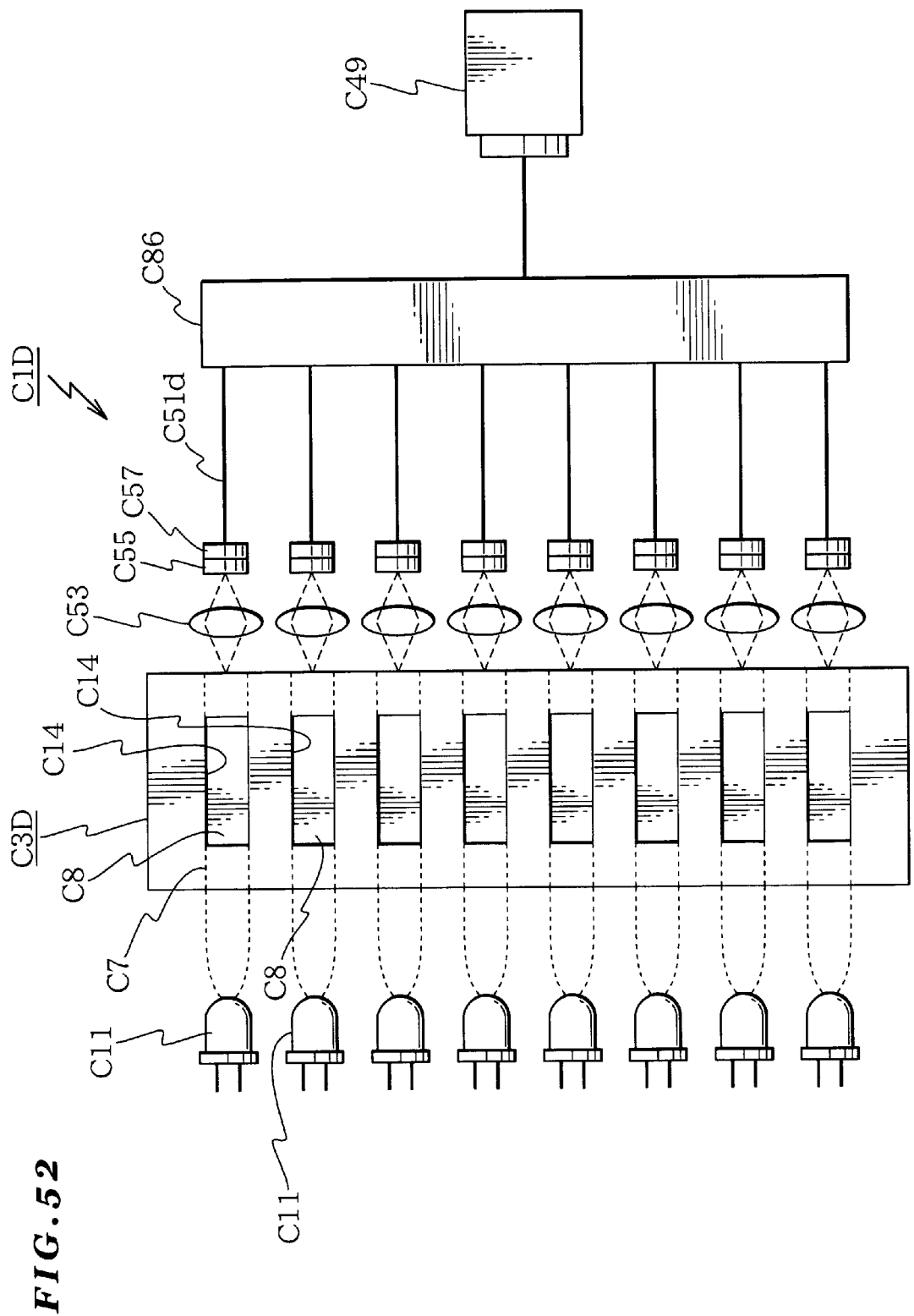
FIG. 52 schematically shows an entire configuration of an immunoassay apparatus according to Embodiment 18 of the present invention.
Figure 53:
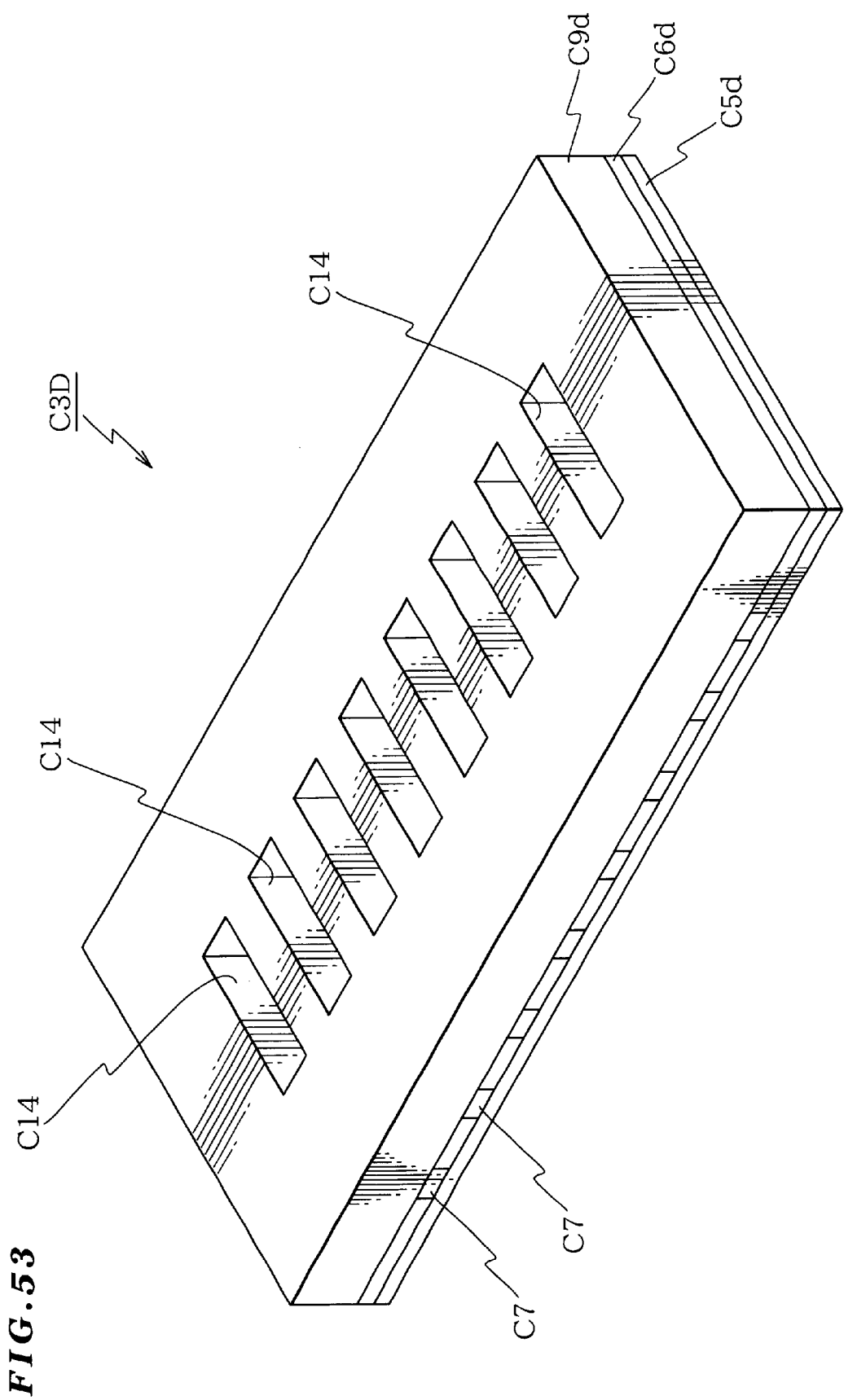
FIG. 53 is a perspective view of the SPR sensor used in the immunoassay apparatus shown in FIG. 52.

FIG. 52 and FIG. 53 shows an entire configuration of an immunoassay apparatus C1D according to Embodiment 18 of the present invention. This embodiment is characterized in that the SPR sensor cell C3D has a plurality of sample reservoirs C14 as will be detailed below.

Firstly, the SPR sensor cell C3D has eight sample reservoirs C14. Correesponding to the eight sample reservoirs C14, eight cores C7 are mounted. In this embodiment the cores C7 constitute the bottom of the sample reservoir 14. Thus, the bottom serves as an SPR sensing portion C8. The SPR sensing portions, as has been described above, is constituted by a thin metal film and a dielectric film, to which an antibody (or antigen) is fixed.

It should be noted that in the immunoassay apparatus C1D of the present embodiment, eight cores 7 are arranged in parallel to one another on the first clad C5d, and intermediate clads C6d are mounted between the respective cores and at positions to sandwich the outer cores. Then, the second clad C9d is mounted on the cores and and the intermediate clads C6d.

Moreover, the immunoassay apparatus C1D includes a light source (white LED lamp) C11, a converging lens C53, a receptacle C55, and an optical fiber C51d for each of the cores C7. That is, there provided eight sets of these members.

Each of the optical fibers C51d is connected to an optical coupler C86. This optical coupler transmits the light from the eight optical fibers C51d to the light analyzing means (Spectrum Anlyzer). Here, the white LED lamps are turned on one after another so that the lights passing through the cores C7 are successively transmitted to the optical analyzing means.

When using the SPR sensor cell C3D having a plurality of cores C7, it is possible to perform in a short time a series of immunoassay for various samples (different antigens or antibodies).

Thus, the case of eight cores C7 has been explained. However, the number of cores may be two to seven or more than nine. In such a case, the number of the converging lenses C53 and the optical fibers 51d should be determined according to the number of cores.

Embodiment 19

Figure 54:
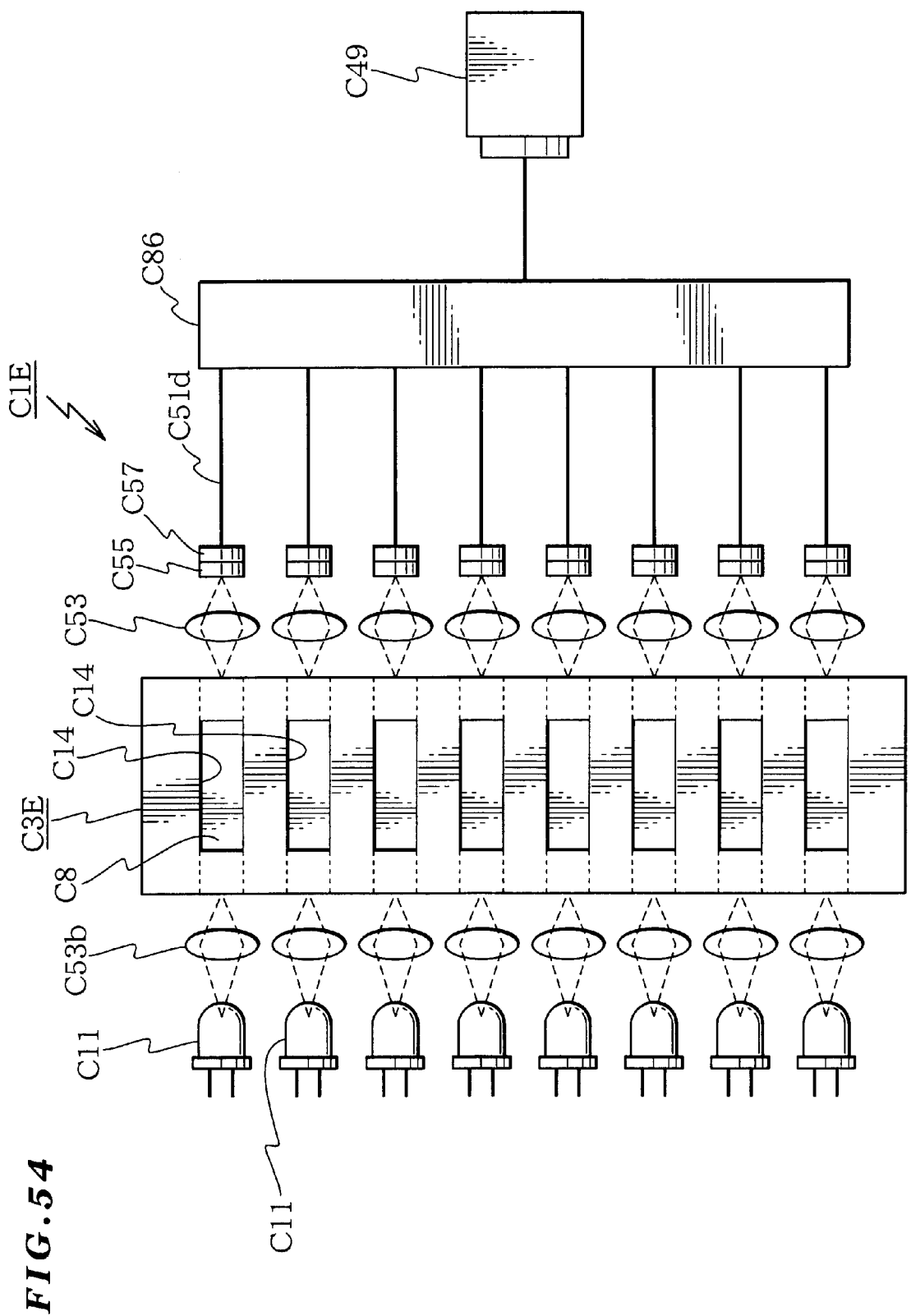
FIG. 54 schematically shows an entire configuration of an immunoassay apparatus according to Embodiment 19 of the present invention.

FIG. 54 schematically shows an immunoassay apparatus C1E according to Embodiment 19 of the present invention. This immunoassay apparatus has almost identical configuration as the immunoassay apparatus of Embodiment 18 except for that a converging lens is provided between each of the light sources C11 and the SPR sensor cells C3E. In this configuration, the light emitted from the light source C11 can be effectively collected to be introduced into the SPR sensor cell C3E.

Embodiment 20

Figure 55:
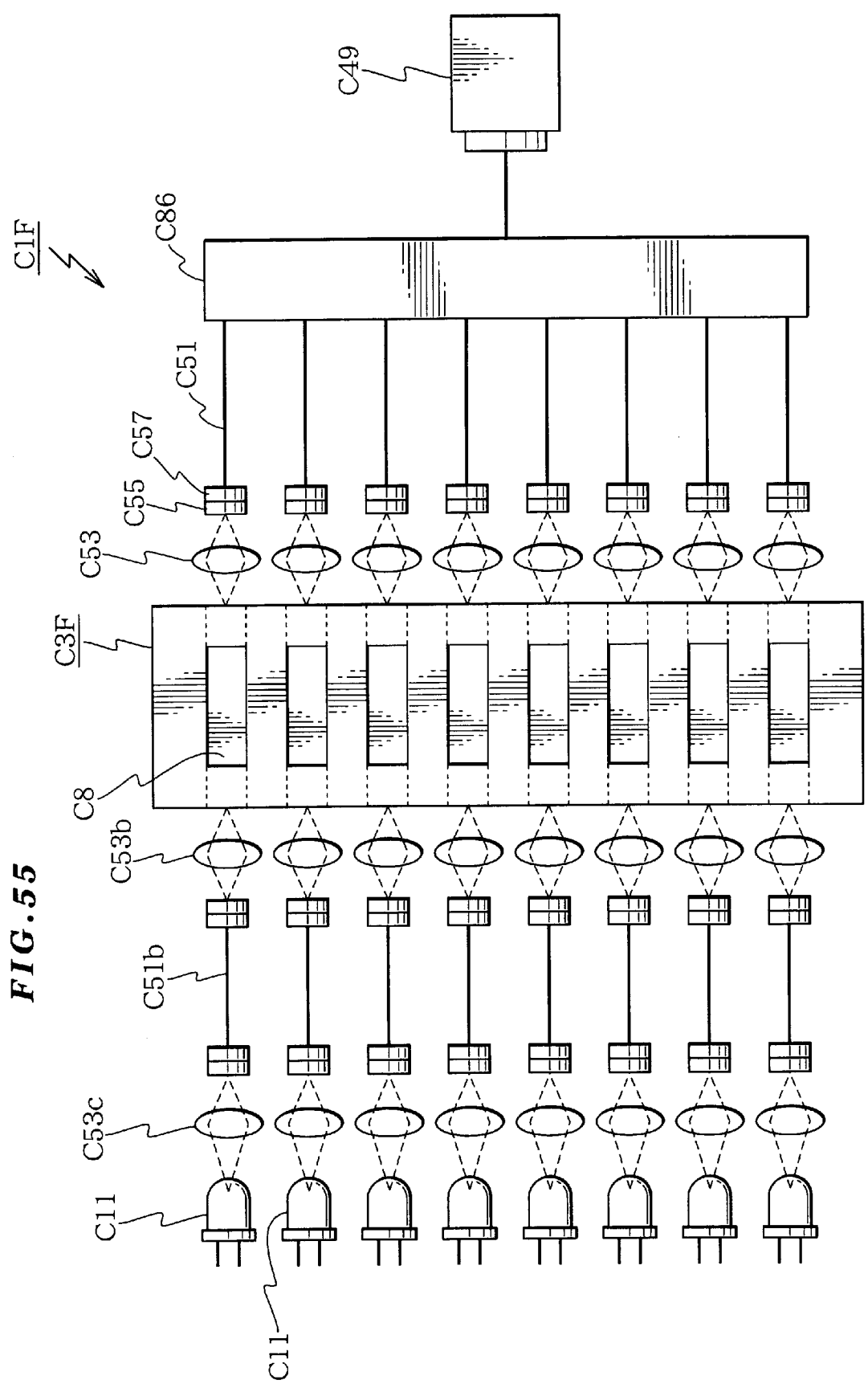
FIG. 55 schematically shows an entire configuration of an immunoassay apparatus according to Embodiment 20 of the present invention.

FIG. 55 schematically shows an immunoassay apparatus C1F according to Embodiment 20 of the present invention. This immunoassay apparatus has almost identical configuration as the immunoassay apparatus of Embodiment 19 except for that an optical fiber C51b is provided between each of the light sources C11 and the SPR sensor cells C3F. In this configuration, it is possible to arrange the light source C11 and the SPR sensor cell C3F at a certain distance, thus enabling various configuration for reducing the entire size of the immunoassay apparatus C1F.

Embodiment 21

Figure 56:
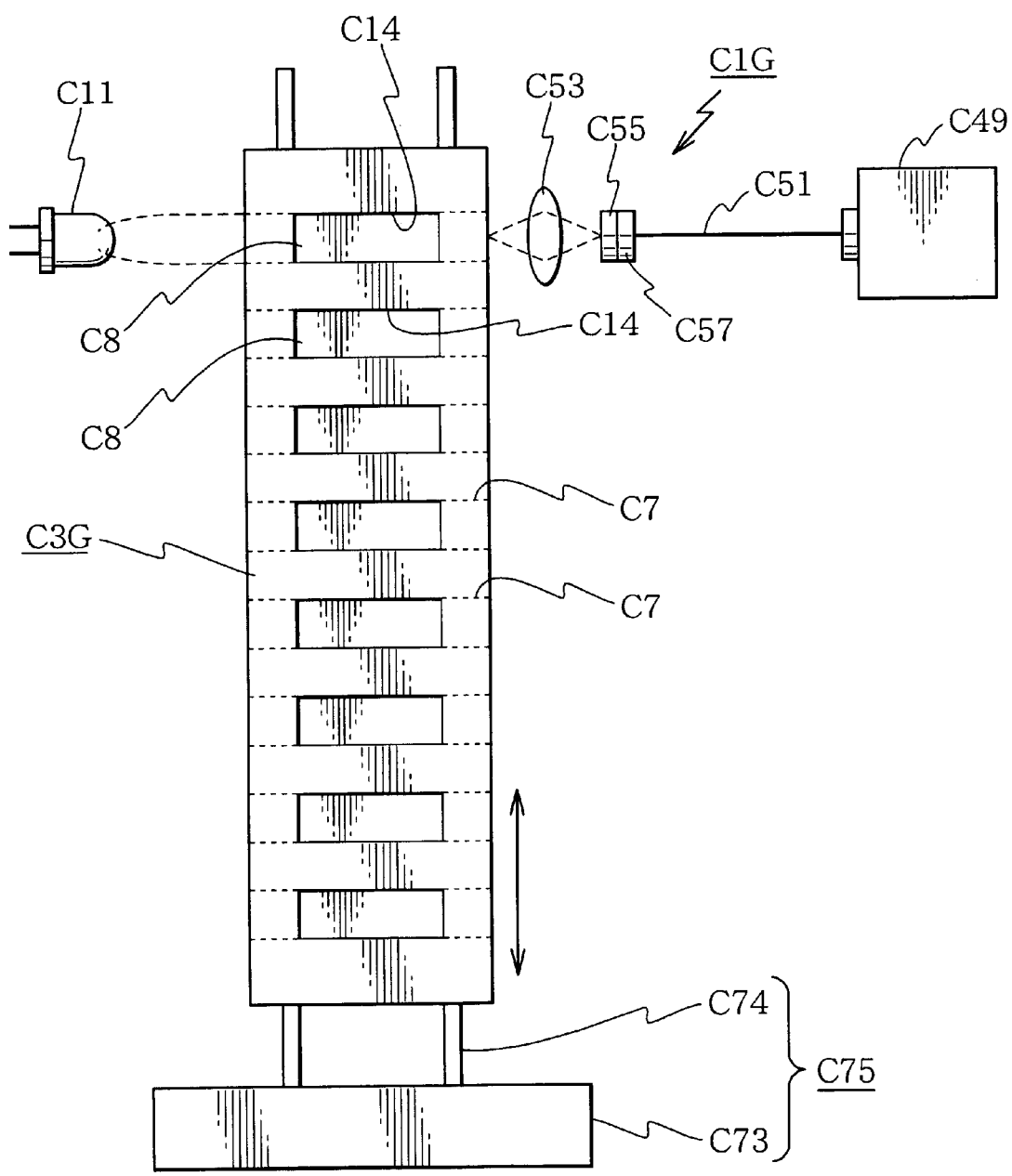
FIG. 56 schematically shows an entire configuration of an immunoassay apparatus according to Embodiment 21 of the present invention.

FIG. 56 schematically shows an entire configuration of an immunoassay apparatus C1G according to Embodiment 21 of the present invention comprising an SPR sensor cell C3G having a plurality of sample reservoir 14 and a set of light source C11 and a converging lens C53.

In an actual immunoassay, the SPR sensor cell C3G is moved so that different samples reservoirs 14 are subjected to the immunoassay.

The SPR sensor cell C3G used in this embodiment has eight cores and eight sample reservoirs C14 corresponding to the respective cores. The SPR sensing portion is identical to the aforementioned SPR sensing portion. The SPR sensor cell C3G is mounted on a predetermined cell movement mechanism C75. This cell moving mechanism 75 shifts the SPR sensor cell C3G in the direction of the core arrangement. More specifically, the SPR sensor cell C3G is moved along two rails C74.

Moreover, the cell moving mechanism C75 has predetermined stop positions where the respective cores or the SPR sensor cell C3G can be stopped. Actually, in order to move the SPR sensor cell C3G an external force should be applied to the SPR sensor cell C3G. For example, a wire or belt may be attached to the SPR sensor cell C3G to move, or the rail C74 may be constituted by a ball bearing screw so that the rail 74 is rotated to move the SPR sensor cell C3G.

On the other hand, it is also possible to fix the SPR sensor cell C3G while moving the set of the light source C11 and the converging lens C53. Here, with the movement of the converging lens, the receptacle C55 is also moved. Since the receptacle C55 is connected via an optical fiber C51 to the light analyzing means C49, the receptacle can be moved with a great flexibility. It should be noted that when moving the set of the light source C11 and the converging lens C53, it is necessary to maintain the optical system setting such as a distance between the light source C11 and the SPR sensor cell C3G, and the distance between the converging lens 53 and the SPR sensor cell C3G.

Embodiment 22

Figure 57:
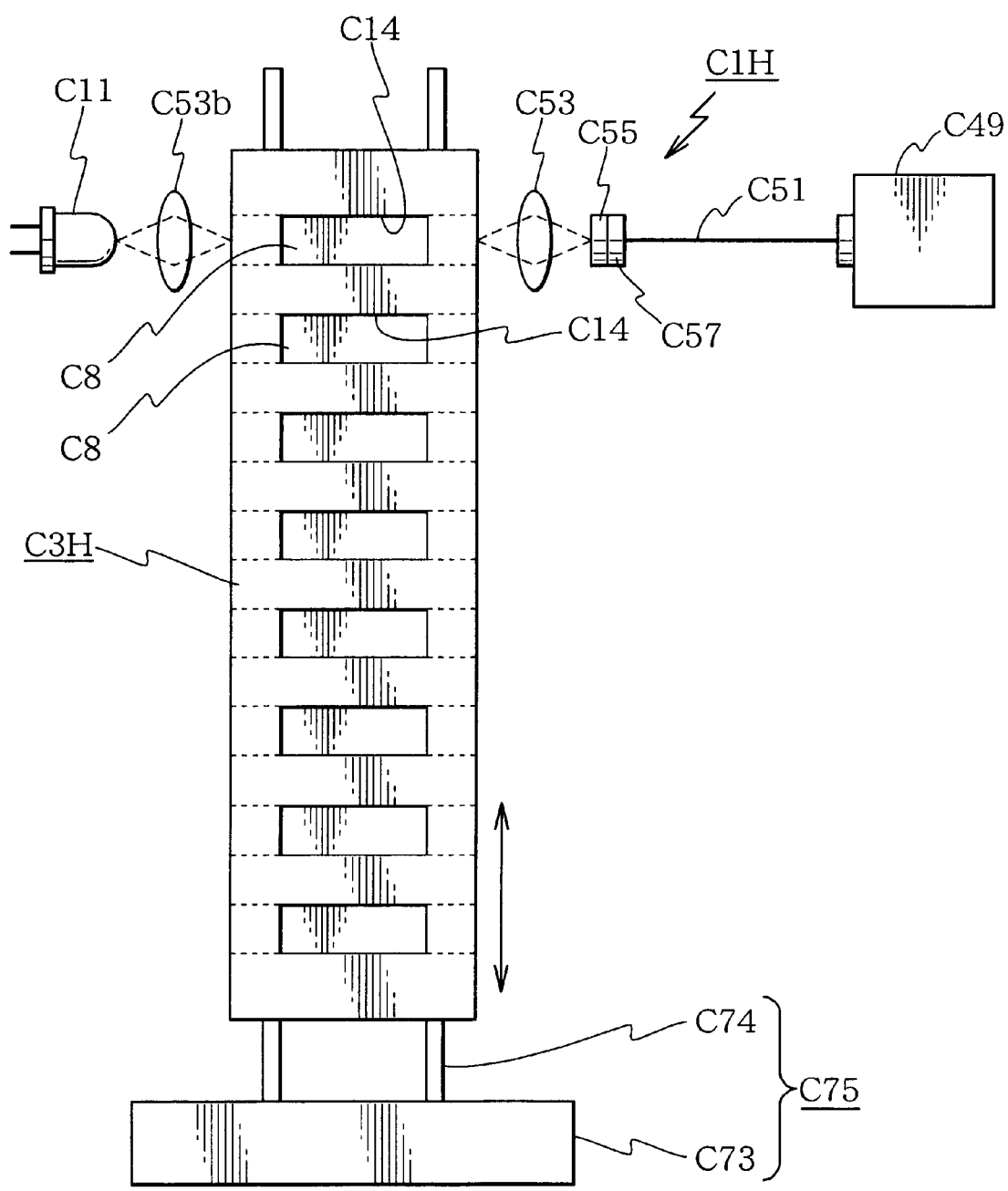
FIG. 57 schematically shows an entire configuration of an immunoassay apparatus according to Embodiment 22 of the present invention.

FIG. 57 schematically shows an entire configuration of an immunoassay apparatus C1H according to Embodiment 21 of the present invention. Embodiment 22 has an identical configuration as Embodiment 21 except for that a converging lens C53b is provided between the light source C11 and the SPR sensor sell C3H. This converging lens C53b converges the light L emitted from the light source (white LED lamp) C11 so as to effectively introduce the light into a core.

The converging lens C53b has a diameter and curvature determined in accordance with the emission angle (directivity). Note that in this embodiment, the converging lens C53b allocated between the SPR sensor cell C3H and the receptacle C55 is identical to the converging lens C53 allocated between the SPR sensor cell C3H and the receptacle C55. However, the converging lenses C53 and C53b may also be different according to the characteristics of the white LED lamp and the SPR sensor cell C3.

Embodiment 23

Figure 58:
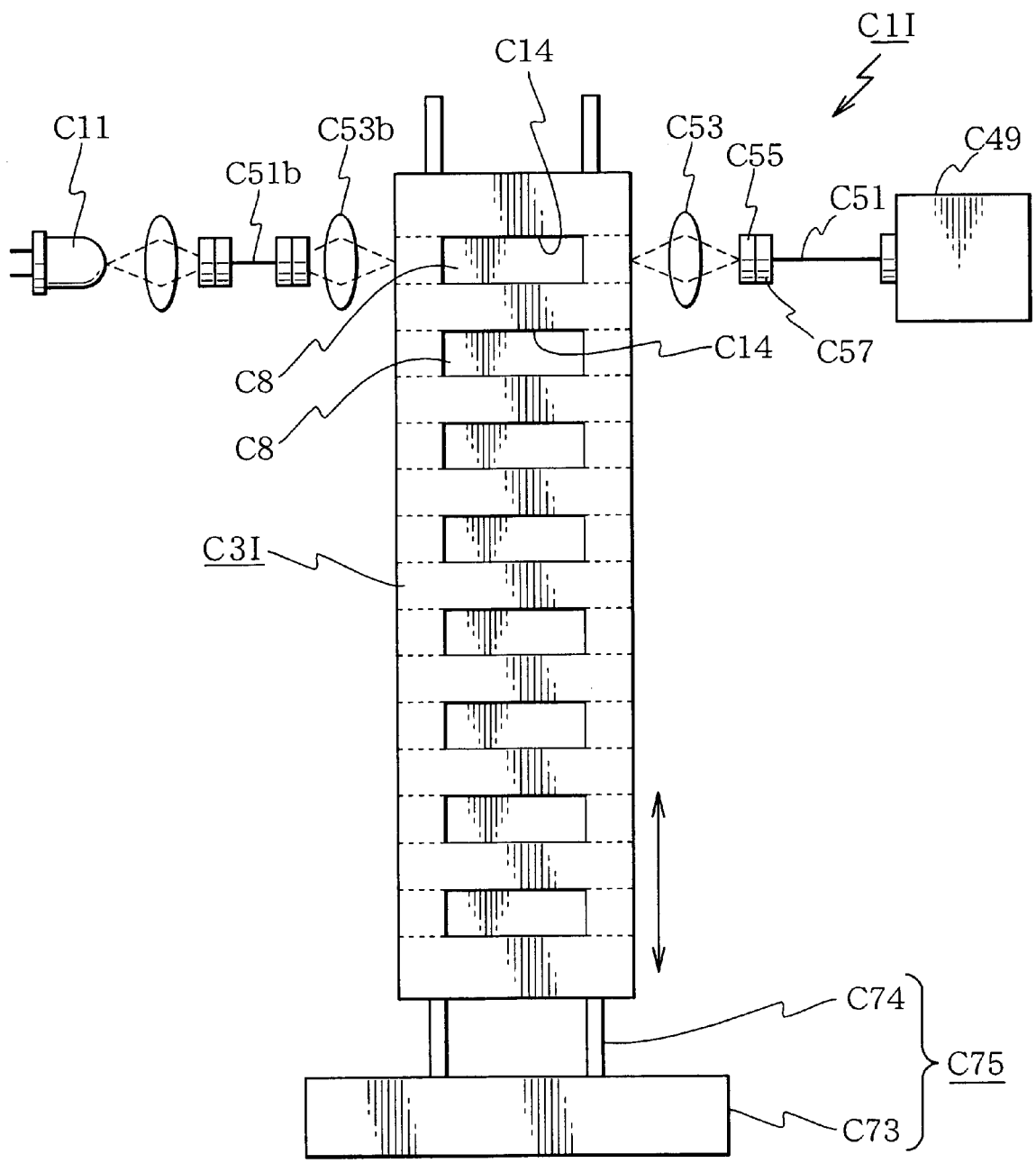
FIG. 58 schematically shows an entire configuration of an immunoassay apparatus according to Embodiment 23 of the present invention.

FIG. 58 schematically shows an entire configuration of an immunoassay apparatus C1I according to Embodiment 23 of the present invention. Embodiment 23 has an identical configuration as the Embodiment 22 except for that an optical fiber C51b is provided between the light source C11 and the SPR sensor cell C3I. When the optical fiber C51b is provided between the light source C11 and the SPR sensor cell C3I, it is possible to arrange the light source at a distance from the SPR sensor cell C3I. This enables to arrange the immunoassay apparatus C1I in various way so as to reduce the entire size of the immunoassay apparatus.

Embodiment 24

Figure 59:
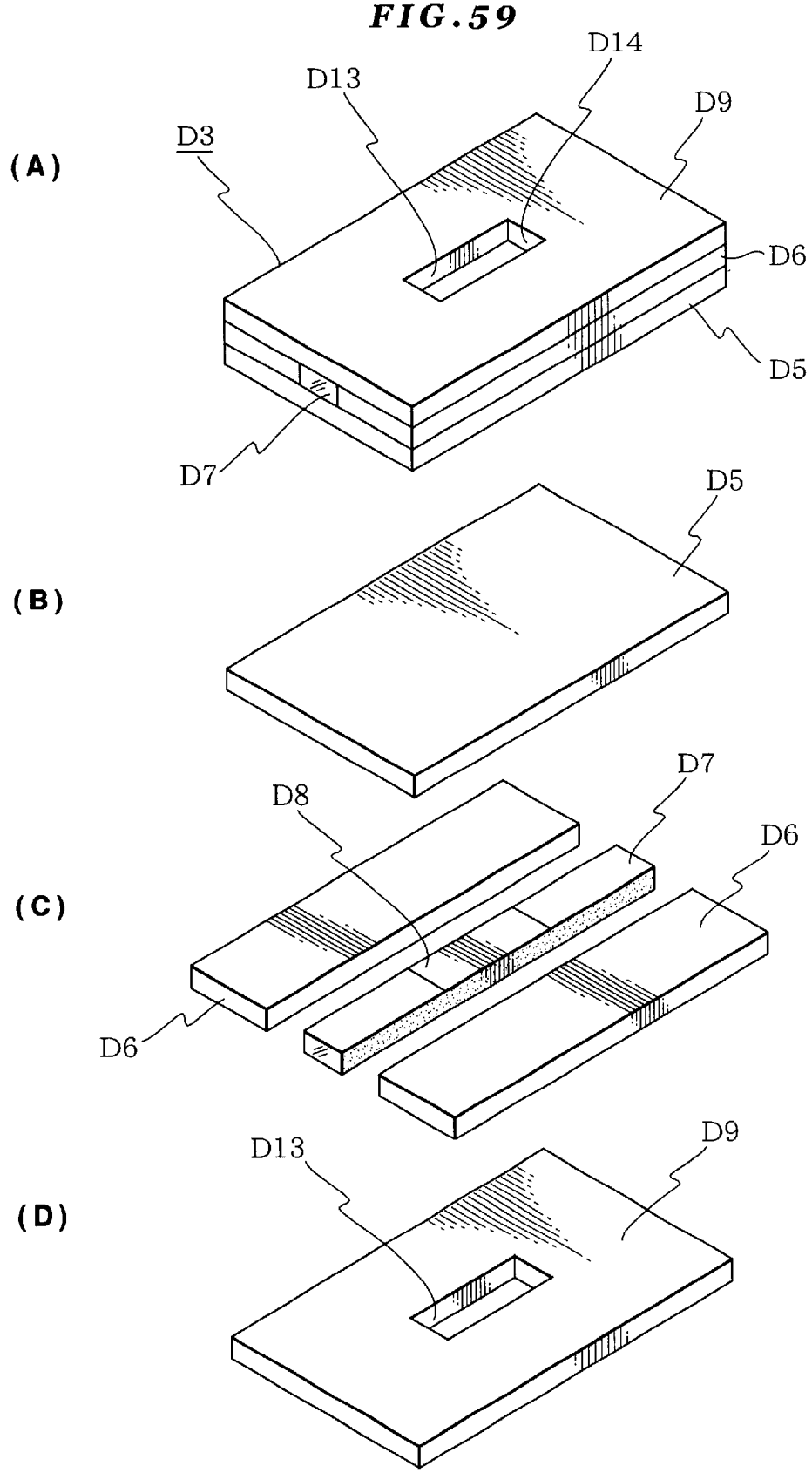
FIG. 59 is a perspective view of an SPR sensor according to Embodiment 24 of the present invention.

Description will now be directed Embodiment 24 with reference to FIG. 59.

FIG. 59 is a perspective view of the SPR sensor according to Embodiment 24. The SPR sensor of this embodiment uses an optical waveguide (core). More specifically, the SPR sensor D3 is constituted by a sheet-shaped first clad (substrate) D5, a core D7 arranged on this first clad, and two intermediate clads D6 to sandwich this core D7 from both sides, and a second clad (upper plate) D9 to cover the core D7 and the intermediate clad D6. It should be noted that the optical waveguide may be planer type, strip type, embedded type, lens type, or the like.

The first clad D5 is made from glass or the like and formed into a thin sheet shape. The core D7 is placed on this first clad D5. The core extend over the entire length of the SPR sensor cell D3. This core is made from glass, plastic, or the like.

The core D7 may be attached to the first clad D5 using an adhesive or by way of heating for melting the boundary surfaces between the first clad D5 and core D7. The same applies to the mounting of the second clad D9 on the core D7 and the intermediate clad D6. When an adhesive is used, light attenuation by the adhesive should be considered, and it is necessary to use an adhesive having a lower refraction factor than the refraction factor of the cores D7.

More specifically, it is possible to use a UV adhesive. Alternatively, it is also possible to use a so-called matching oil for attaching the core D7 to the clads. In this case, too, the refraction factor should be correctly selected.

The intermediate clads D6 is arranged so as to sandwich the core from both side. These intermediate clads D6 have a thickness identical to that of the core D7. Accordingly when the core D7 and the intermediate clads D6 are attached to one another, they constitute a sheet-shaped member having a uniform thickness.

Moreover, a predetermined through hole D13 is formed at the center of the second clad D9. The through hole extends from the upper surface of the second clad D9 reaches the upper surface of the core D7. Accordingly, a part of the surface of the core D7 is exposed to the through hole D13. This part of the core D7 corresponding to the through hole D13 is covered with a thin metal film as will be detailed later.

Here, the through hole D13 may be formed by drilling the second clad D9 of a single sheet shape. That is, the through hole D13 may be formed by using a predetermined drilling machine.

The through hole D13 thus prepared and the surface of the core D7 constitute a void space of a rectangular parallelopiped. This void space serves as a sample reservoir for an immunoassay.

It should noted that instead of drilling the second clad D9 of a single sheet, it is possible to constitute the sheet by combining a plurality of members. In this case the step of drilling the through hole is not necessary. Moreover, it is preferable to constitute the second clad D9 and the intermediate clad D6 as a unitary block. This reduces the number of steps of assembly.

Moreover, in the core D7 having a rectangular cross section, the two opposing side surfaces to be attached to the intermediate clads are subjected to a predetermined surface treatment. More specifically, two opposing side surfaces of the core D7 having no SPR sensing portion are obscured, or coated with an aluminum (Al) coating or black paint. Such a surface treatment prevents light reflection from the aforementioned side surfaces of the core D7.

With the aforementioned surface treatment, it is possible to emit from the SPR sensor cell only the light reflected by the SPR sensing portion and the side surface opposing to SPR sensing portion. This light is subjected to an analysis by the light analyzing means, so as to determine only the wavelength distribution of the light used for the surface plasmon resonance.

In this embodiment, two side surfaces of the core are subjected to the surface treatment. However, the present embodiment is not limited to the aforementioned. For example, if the SPR sensing portion is formed on the upper surface of the core, the lower side surface of the core may be subjected to the surface treatment.

In a case when the side surfaces of the core are already obscured when produced, there is no need of surface treatment (polishing). That is, it is possible to polish only the side surface corresponding to the SPR sensing portion and a surface opposing to it. Thus, if a core has obscured side surfaces when produced, what is needed is only to polish a necessary side surface. This reduces the total number of steps for production.

Here, a light portion which has entered the core D7 and is reflected by the SPR sensing portion and the surface opposing to it. On the other hand, almost all of light portions which have reached the obscured side surfaces are not reflected. Thus, the light portions not used for surface plasmon resonance are eliminated.

The light emitted from the SPR sensor cell is introduced into the light analyzing means so as to determine a wavelength distribution of the light L after an immune reaction to be compared to a wavelength distribution when no immune reaction is caused.

Thus, explanation has been given on a case that a low-reflection surface is formed on the core D7 of the SPR sensor cell D3. However, it is also possible to perform the surface treatment on the clads. When the low-reflection surface is formed on the clads, it is possible to obtain the same effect as when the low-reflection surface is formed on the core.

Modified Example 1 of Embodiment 24

Figure 60:
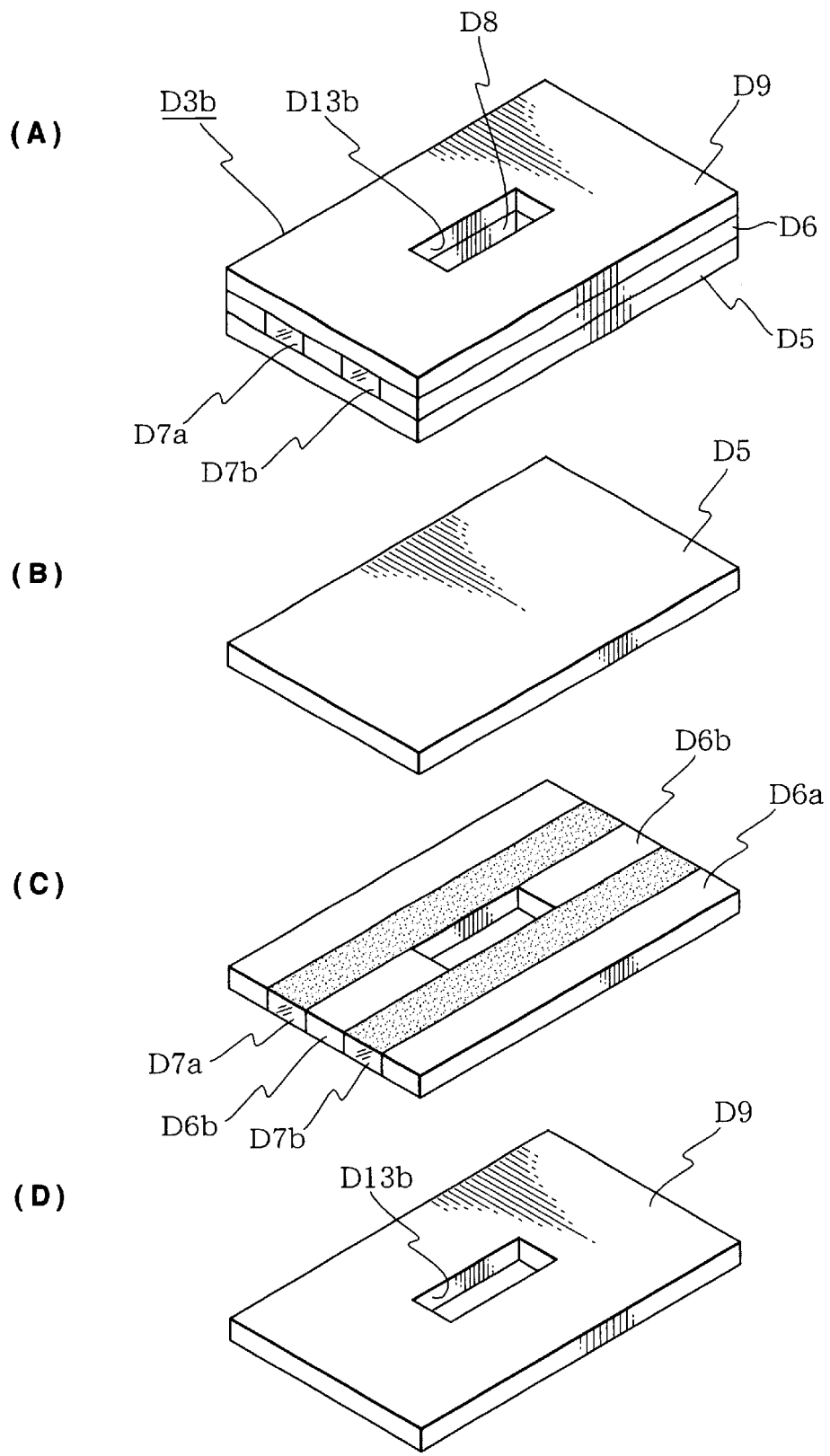
FIG. 60 is a perspective view of a modified example of the SPR sensor according to Embodiment 24.

Next, referring to FIG. 60, explanation will be given on a modified example of the SPR sensor cell. The sensor cell D3*b* differs from the SPR sensor cell of the aforementioned sensor cell in that two cores are used.

More specifically, this SPR sensor cell D3*b* is constituted by: a sheet-shaped first clad (substrate) D5, two cores D7*a* and D7*b* mounted on this first clad Dd5; a center clad D6*b* sandwiched by the cores D7*a* and D7*b*; side clads D6*a* to sandwich the two cores D7*a* and D7*b* from outside; and a second clad (upper plate) D9 to cover the cores D7*a*, D7*b*, the center clad D6*b* and the side clads D6*a*.

Moreover, the center clad D6*b* is divided into two blocks so as to define a void space between them. This void space corresponds to the predetermined through hole D13*b* formed at approximately center of the second clad D9. More specifically, the through hole extends from the upper surface of the second clad to the position defined by the two cores D7*a* and D7*b*. That is, the cores D7*a* and D7*b* are arranged at a predetermined distance from each other and parallel to each other. The through hole D13 has a width approximately identical to the distance between the cores D7*a* and D7*b*. Accordingly, a part of surfaces of the cores D7*a* and D7*b* are exposed to the through hole D13*b*.

Because the second clad D9 is constituted as described above, a void space of rectangular parallelopiped is defined by the through hole D13*b* of the second clad D9, two cores D7*a* and D7*b*, the center clads D6*b*, and the surface of the first clad D5. This void space serves as a sample reservoir for containing a sample for immunoassay. The side of the SPR sensor cell core which is exposed to the sample reservoir serves as an SPR sensing portion. More specifically, two opposing side surfaces facing the sample reservoir respectively serve as the SPR sensing portions.

On the other hand, the upper and lower surfaces of the respective cores have been subjected to a surface treatment so as to have a low-reflection surface. More specifically, the upper and lower surfaces of the cores shown in FIG. 60C have a low-reflection surface. On the contrary, the side surfaces of the sensing portion and the side surface opposing to it have a normal surface. That is, the surfaces other than the SPR sensing portion and its opposing surface are made to have a low reflection, which in turn enables to improve the immunoassay.

Modified Examples 2 and 3 of Embodiment 24

FIG. 61 is a perspective view of another modification of the SPR sensor cell according to Embodiment 24. The SPR sensor cell shown D3C shown in FIG. 61A has one core and the SPR sensor cell D3D shown in FIG. D61B has two cores. In these SPR sensor cells, surface treatment has been performed to the end surfaces excluding the end surface of the cores. More specifically, the first clad, the second clad, and intermediate clad have end surfaces subjected to surface treatment so that light cannot pass. The surface treatment may be obscuring by sandblast or the like, or coating with aluminum (Al) or applying a black paint.

When such a surface treatment has been performed, the light comes into only the cores D7 and D7*a*. If the light passes through the end surfaces of the clads, the light may come into the cores D7 and D7*a*, which may lower the immunoassay accuracy (sensitivity).

Embodiment 25

Figure 62:
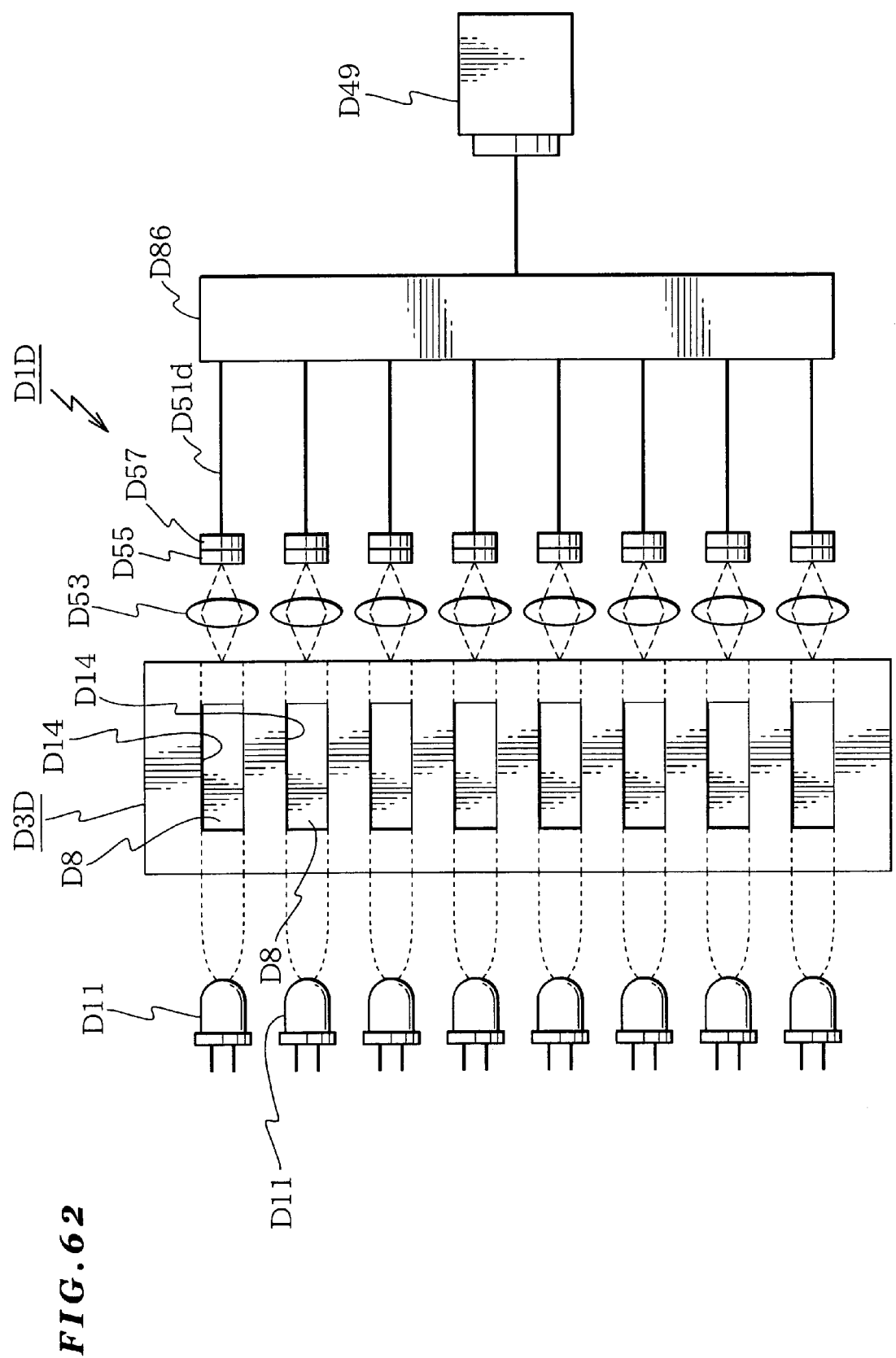
FIG. 62 is a plane view of an entire configuration of the immunoassay apparatus according to Embodiment 25 of the present invention.
Figure 63:
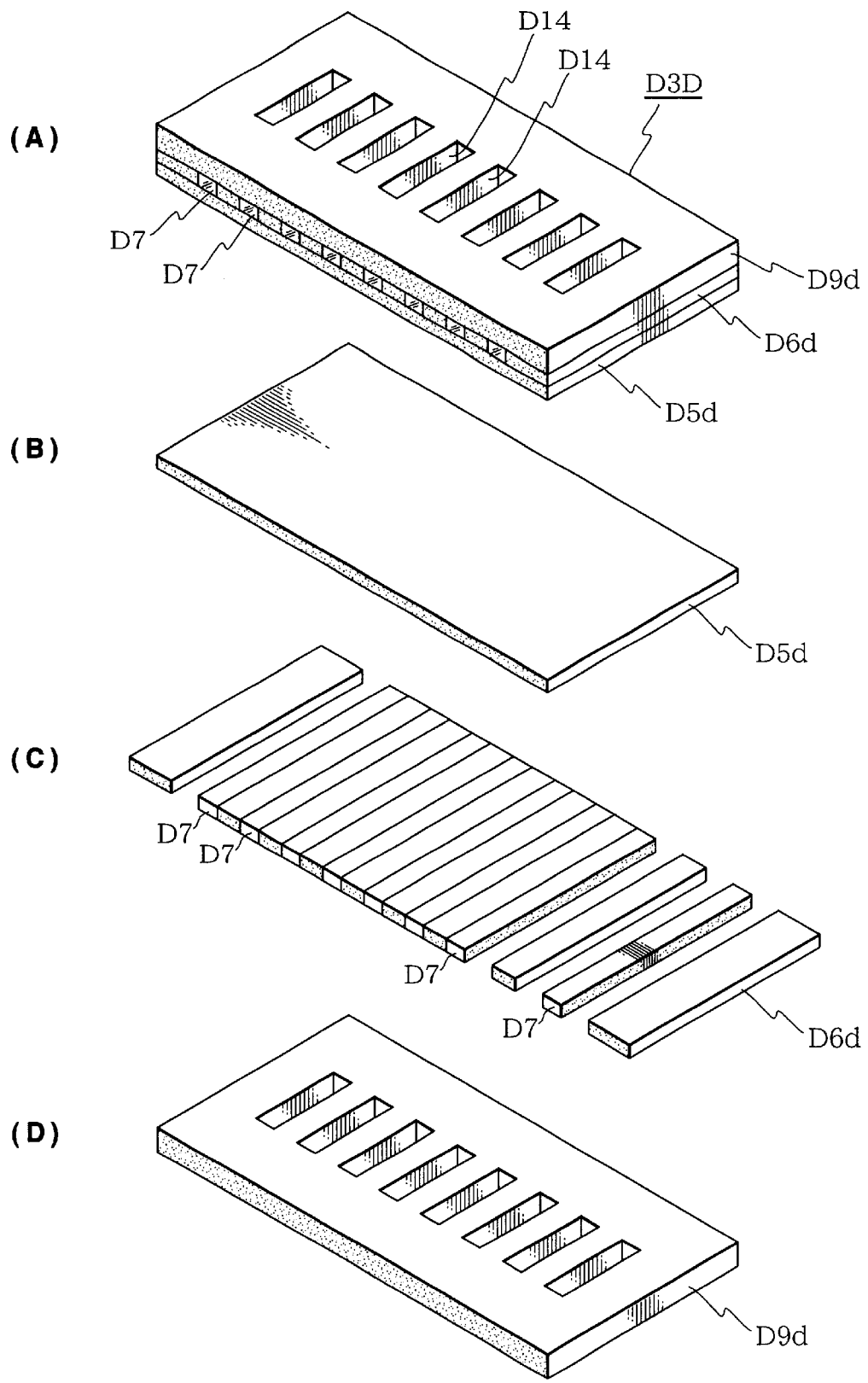
FIG. 63 is a perspective view of the SPR sensor cell used in the immunoassay apparatus shown in FIG. 62.
Figure 64:
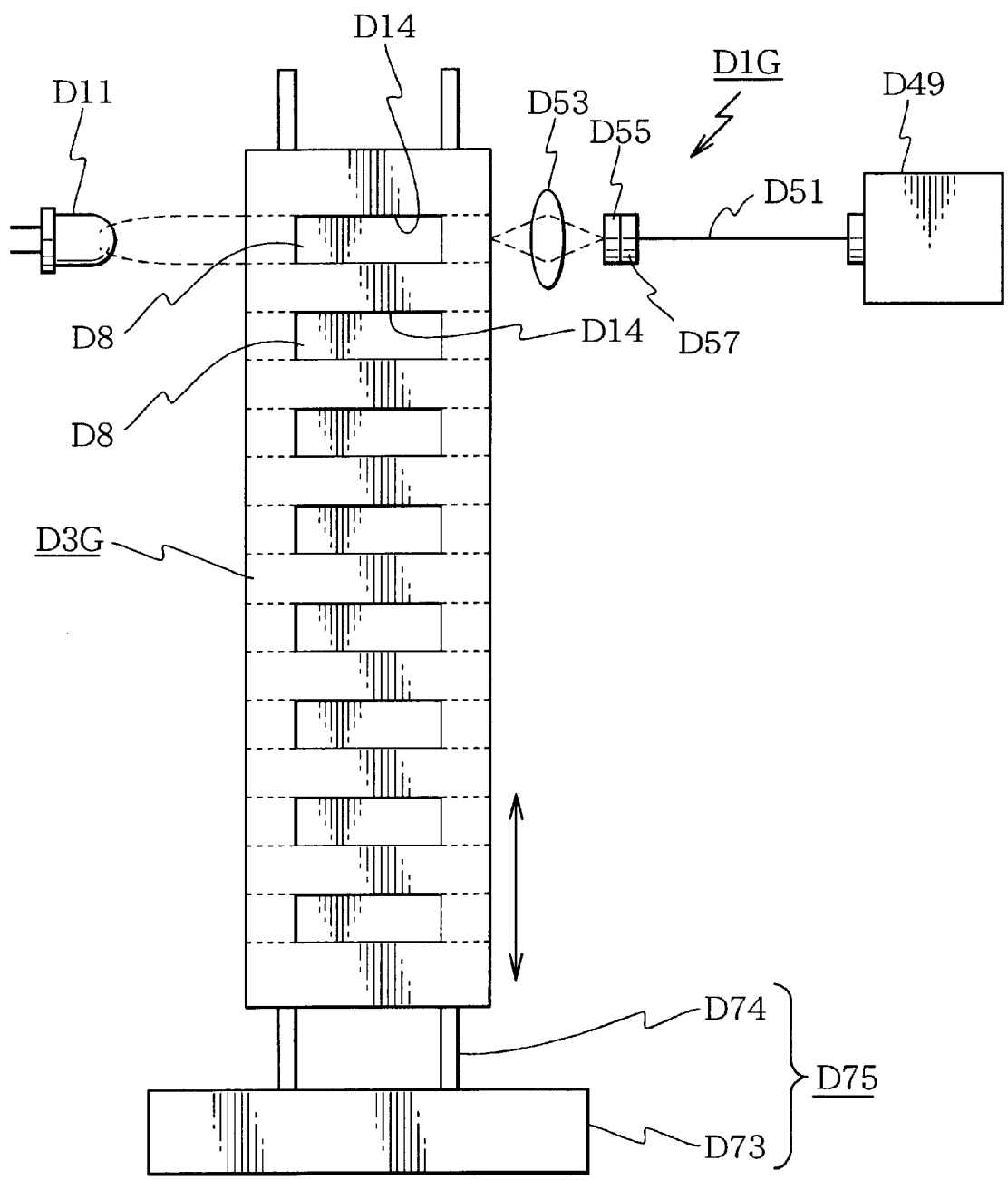
FIG. 64 schematically shows an entire configuration of a modified immunoassay apparatus according to Embodiment 25.

Description will now directed to an immunoassay apparatus according to Embodiment 25 with reference to FIG. 62, FIG. 63. And FIG. 64 shows modification of immunoassay apparatus showing in FIG. 62.

This immunoassay apparatus is characterized in that the SPR sensor cell has a plurality of sample reservoirs. Hereinafter, the SPR sensor cell will be detailed.

Firstly, the SPR sensor has eight sample reservoirs D14 and eight cores D7 corresponding to the respective sample reservoirs D14. In this embodiment, each of the cores D7 constitutes the bottom of the respective sample reservoirs D14. This bottom serves as the SPR sensing portion D8. In this SPR sensing portion D8, a thin metal film and dielectric film are formed, and antibody (or antigen) is fixed.

It should be noted that in the immunoassay apparatus D1D according to the present embodiment, the eight cores D7 are arranged on the first clad D5 in parallel to one another, and intermediate clads are arranged between adjacent cores D7 and also arranged outside so as to sandwich the cores D7. These cores D7 and the intermediate clads D6*d* are covered by the second clad D9*d*.

The aforementioned surface treatment has been performed to the side surfaces of the cores which side surfaces (16 in total)are in contact with the intermediate clads D6*d*, so that these side surfaces have a low reflection ratio. The surface treatment may be obscuring by sand blast or the like, or coating with an aluminum (Al) coating, or application of a black paint. All of the cores D7 have identical characteristics.

Moreover, in the immunoassay apparatus D1D, for each of the cores D7, there are provided a light source (white LED lamp) D11, a converging lens D53, a receptacle D55, and an optical fiber D51*d*. That is, there are provided eight such sets. Each of the optical fibers D51*d* is connected to an optical coupler D86. This optical coupler D86 receives light from the eight optical fibers D51*d* and transmit the light to a light analyzing means.

When using the SPR sensor cell D3D having a plurality of cores D7, it is possible to perform a plurality of assays (for different antigens or antibodies) in a short time. In this embodiment, eight cores D7 are provided. However, the number of cores D7 may be two to seven or more than eight. In such case, it is necessary to provide a corresponding number of sets of the light source D11, the converging lens 53, and the optical fiber D51d.

In FIG. 64, the immunoassay apparatus D1G use same SPR sensor cell D3G above described SPR sensor cell D3D. But immunoassay apparatus D1G uses two parallel rails to move the SPR sensor cell D3G.

Embodiment 26

Description will now be directed to Embodiment 26 with reference to FIG. 65 to FIG. 70.

Figure 65:
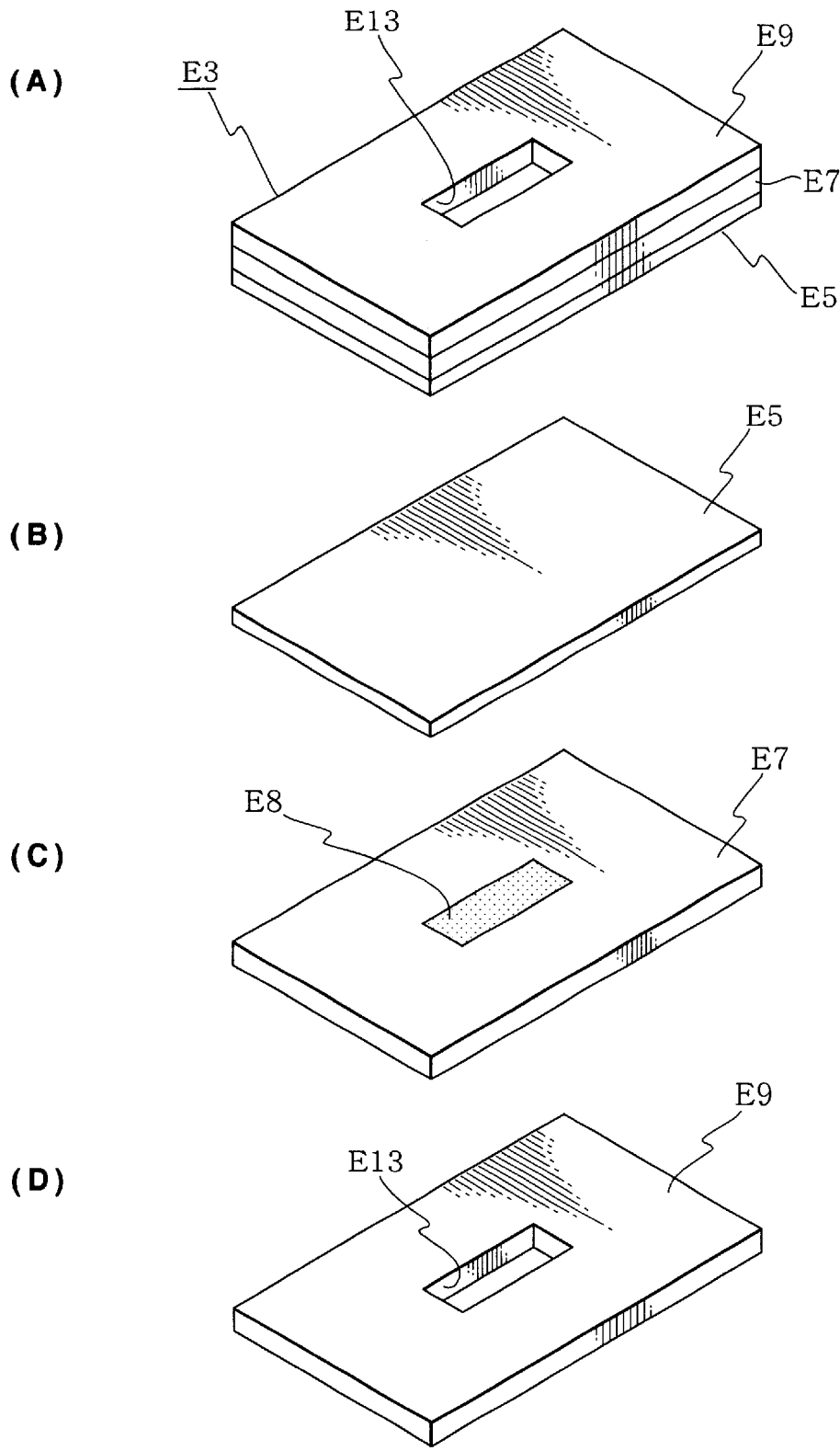
FIG. 65 is a perspective view of an SPR sensor cell according to Embodiment 26.

FIG. 65 is a perspective view of an SPR sensor cell according to this embodiment. The SPR sensor cell E3 according to this embodiment uses an optical waveguide (core). More specifically, the SPR sensor E3 is constituted by: a sheet-shaped first clad (substrate) E5; a sheet-shaped core E7 placed on the first clad; and a second clad (upper plate) E9 placed on this core E7. Note that the optical waveguide may be a plane type, strip type, embedded type, lens type, or the like.

The first clad E5 is made from glass or the like and formed into a thin plate. The first clad E5 has an upper surface polished smooth because the core E7 is mounted on this first clad E5. The lower surface and side surfaces or the end surfaces of this first clad E5 may not be polished. This is because no light should need not be introduced from the end surface of the first clad E5.

The core E7 is a sheet-shaped member made from glass, plastic, or the like for passing the light for immunoassay. The core E7 has a width and length approximately identical to the width and length of the first clad E5. Accordingly, the core E7 covers the entire surface of the first clad E5. Moreover, the core E7 has a lower surface which is polished smooth so as to be incomplete contact with the first clad E5. The core end surfaces from which the light comes in and goes out are also polished smooth. When mounting the core E7 on the first clad E5, it is possible to use an adhesive or to use heat to melt the boundary portion.

It should be noted that an adhesive is used to attach the core E7 onto the first clad E5, it is necessary to consider a light attenuation by the adhesive. That is, it is necessary to use an adhesive having a lower refraction factor than that of the core E7. For example, it is possible to use a UV adhesive.

Moreover, it is possible to use a so-called matching oil for attaching the core E7 to the respective clads. In this case also, the refraction factor should be considered.

Moreover, the core E7 has an upper surface which is also polished smooth, so that a second clad E9 can be attached to the upper surface of the core E7. And each end of the core E7 is also polished. But it is not need to polish each side surface.

The second clad E9 is also sheet-shaped member made from glass or plastic and has width and length almost identical to the core E7. The lower surface of the second clad E9 is also polished smooth and attached to the upper surface of the core E7. But it is not need to polish each end of the second clad E9. And also it is not need to polish upper surface and side surface of the second clad E9.

Moreover, a predetermined through hole E13 is formed approximately at the center of the second clad E9. More specifically, the through hole E13 extends from the upper surface of the second clad E9 to the upper surface of the core E7. Accordingly, a part of the upper surface of the core E7 is exposed to this through hole E13. The surface of the core E7 exposed to this through hole E13 has a thin metal film so as to serve as an SPR sensing portion E8 as will be detailed later.

Next explanation will be given on the relationship between the refraction factors of the first clad E5, the second clad D9, and the core E7. In the SPR sensor E3, the first clad has a refraction factor n1, the core has a refraction factor n2, and the second clad has a refraction factor n3 defined as follows.

$n2>n3=n1$ or $n2>n3$ and $n2>n1$

When this relationship is satisfied, the light introduced into the core E7 advances in the core while being totally reflected repeatedly.

When the core is constituted by a single sheet-shaped member, it is possible to obtain following advantage compared to a combination of a plurality of members. That is, when polishing a core surface, it is possible to polish the entire core surface as a single step. Moreover, there is no need of combining a plurality of members, or a precision processing of the contact surfaces. Accordingly, it is possible to reduce the production cost of the SPR sensor cell. Moreover, it is possible to suppress irregularities in the performance of the SPR sensors.

Next, explanation will be given on a sample reservoir E14, serving as or including an SPR sensing portion E8.

Figure 66:
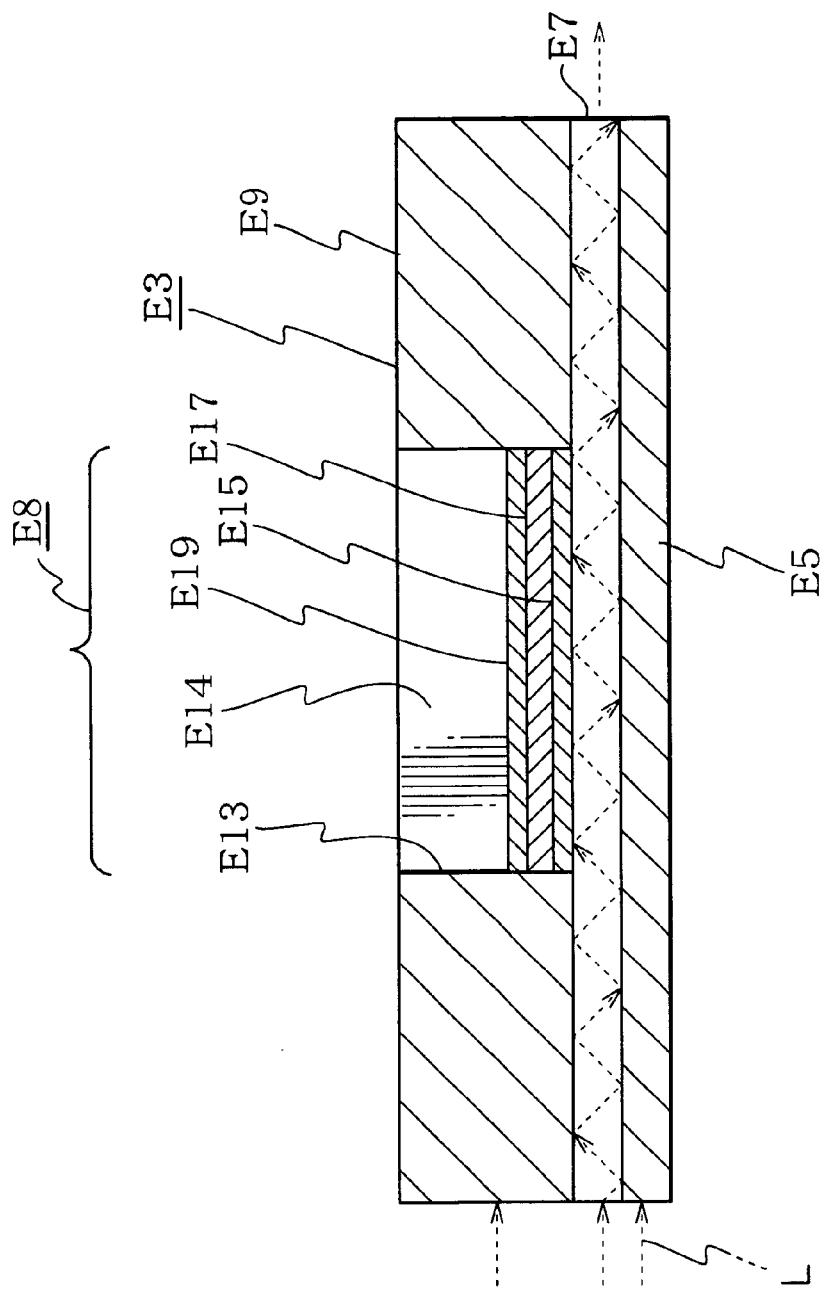
FIG. 66 is a cross sectional view of the SPR sensor shown in FIG. 65.

FIG. 66 is a cross sectional view of the SPR sensor cell E3. The core E7 surface exposed to the through hole E13 is coated by a thin metal film E15 and a dielectric film E17, and an antibody (or antigen) is arranged on this dielectric film E17. The thin metal film may be formed before or after the second clad is mounted on the core E7.

Next, explanation will be given on the function of the SPR sensor cell E3. Firstly, a sample containing a predetermined antigen is introduced into the sample reservoir E14 of the SPR sensor cell E3. If the sample contains an antigen specifically reacting to the antibody E19, an immune reaction is caused, which in turn causes a surface plasmon resonance in the SPR sensing portion E8. This reduces the light intensity of a particular wavelength causing the surface plasmon resonance.

Among the light portions introduced into the core E7, the light portion L having a relation with the surface plasmon resonance passes through the core E7 and comes out of the SPR sensor cell. This light portion L is introduced into a light analyzing means. The light wavelength distribution is different before and after the immune reaction.

Next, explanation will be given on an immunoassay apparatus E1 using the SPR sensor cell E3 according to the present invention, referring to FIG. 67.

Figure 67:
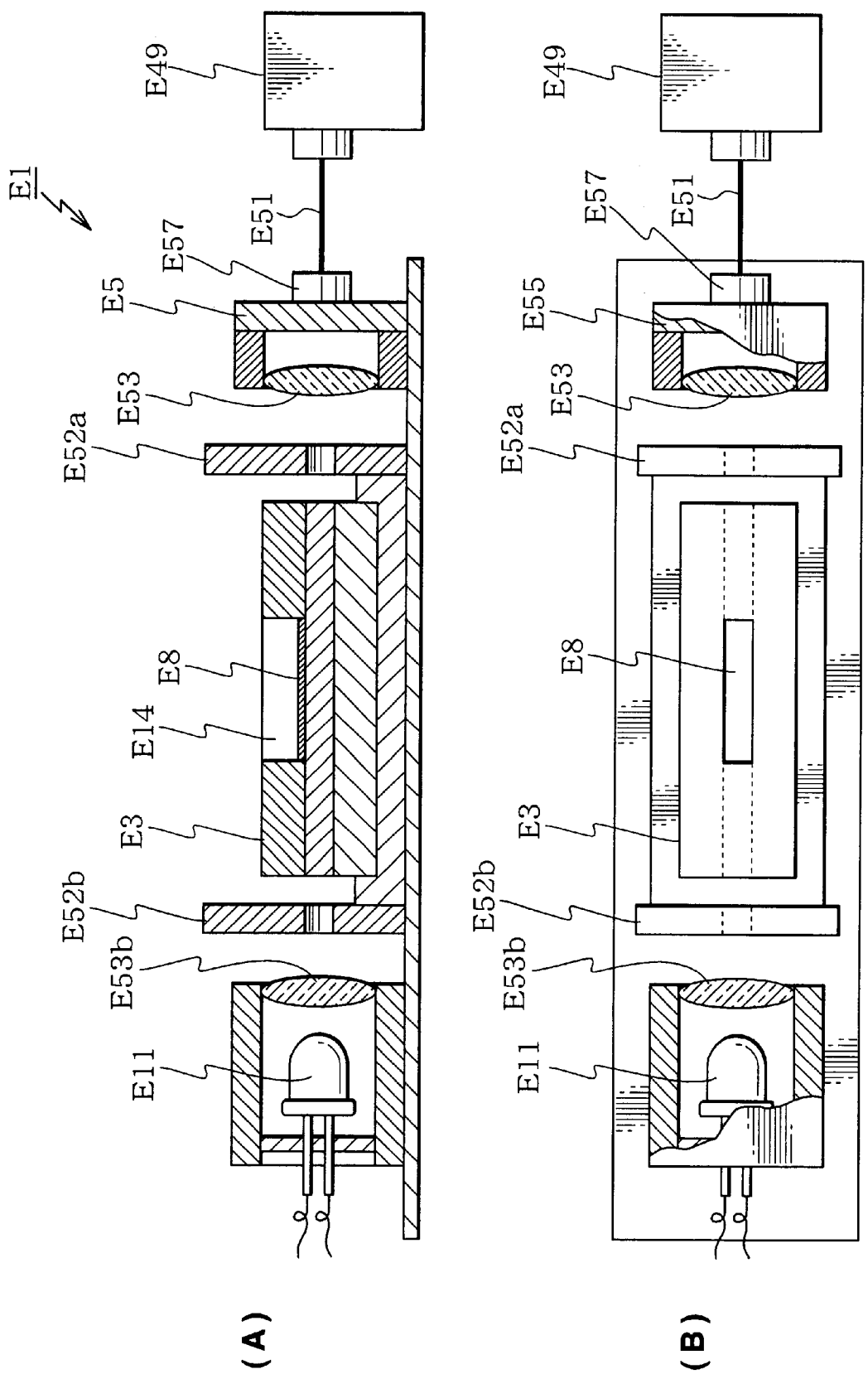
FIG. 67 shows an immunoassay apparatus using the SPR sensor cell shown in FIG. 65.

FIG. 67 schematically shows the entire configuration of the immunoassay apparatus E1. FIG. 67A is a side view and FIG. 67B is a plan view of this immunoassay apparatus E1. As shown here, a light source E11 is provided in the vicinity of the SPR sensor cell E3. A converging lens E53b is also provided between the SPR sensor cell E3 and the light source E11. Moreover, on the opposite side of the SPR sensor cell E3, a converging lens E53, an optical fiber E51, and a light analyzing means E49 are arranged in this order. Note that the light which has passed through the converging lens E53 is introduced into the optical fiber D51 via a receptacle E51 and an optical connector E57.

Furthermore, a pin hole plate E52b is provided between the SPR sensor cell E3 and the converging lens E53b. This pin hole plate is used to improve parallelism of the light which has been converged by the converging lens E52b.

FIG. 68A shows a pin hole plate E52b having a single pin hole, and FIG. 68B shows a pin hole plate having a plurality of pin holes. The latter is used in an immunoassay apparatus having a plurality of light sources a will be detailed later.

Figure 69:
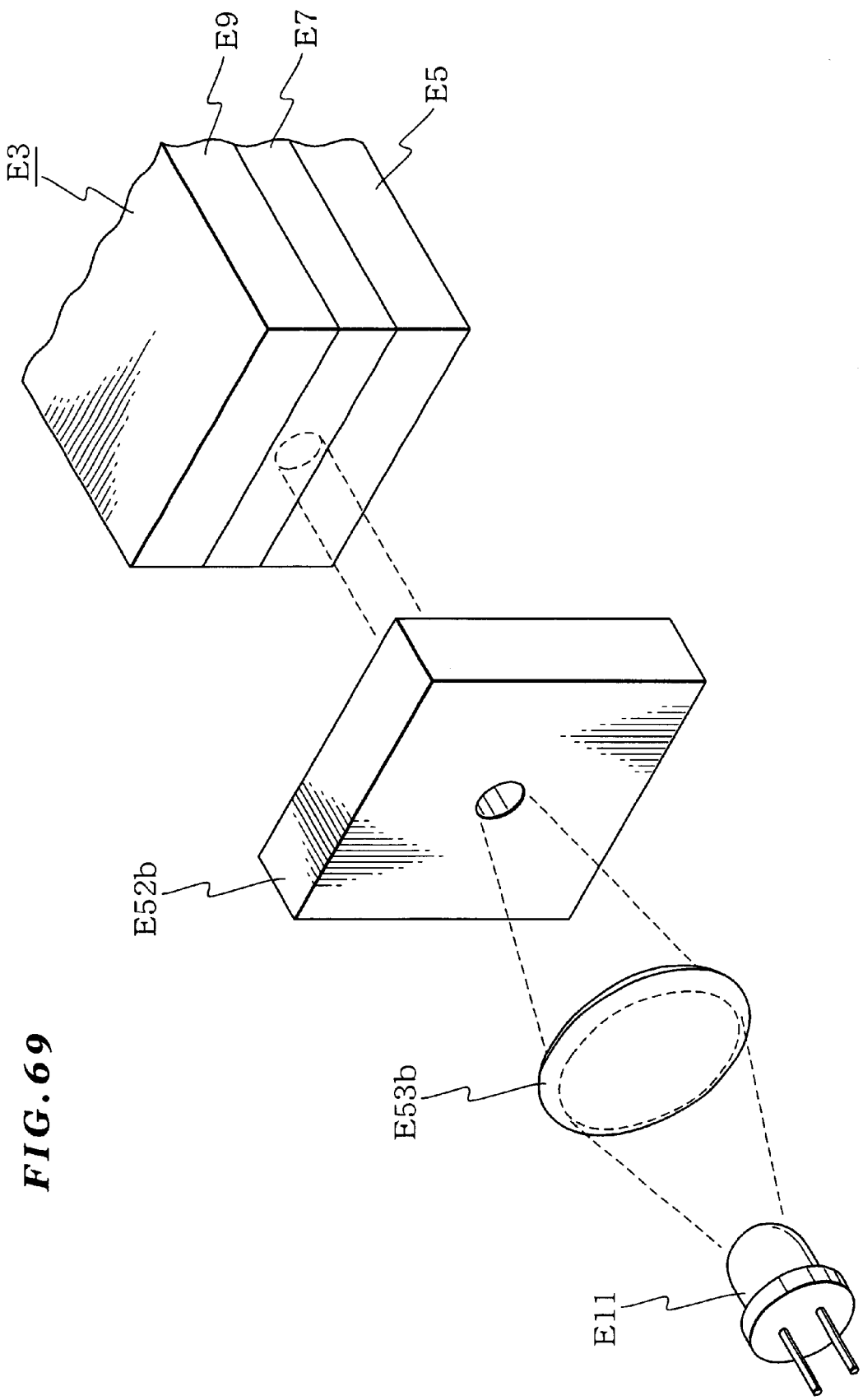
FIG. 69 schematically shows an optical path from the light source to the SPR sensor cell.

Moreover, FIG. 69 shows a light from the light source E11 which is converged by the converging lens E53 and passes through the pin hole plate E52b before entering the core E7. FIG. 69 shows a case when the light from the light source E11 is converged by the converging lens E53 to a diameter equal to or slightly smaller than the diameter of the pin hole of the pin hole plate E52b. In this case, reduction of the light intensity is very small and it is possible to obtain an immunoassay of high accuracy.

Figure 70:
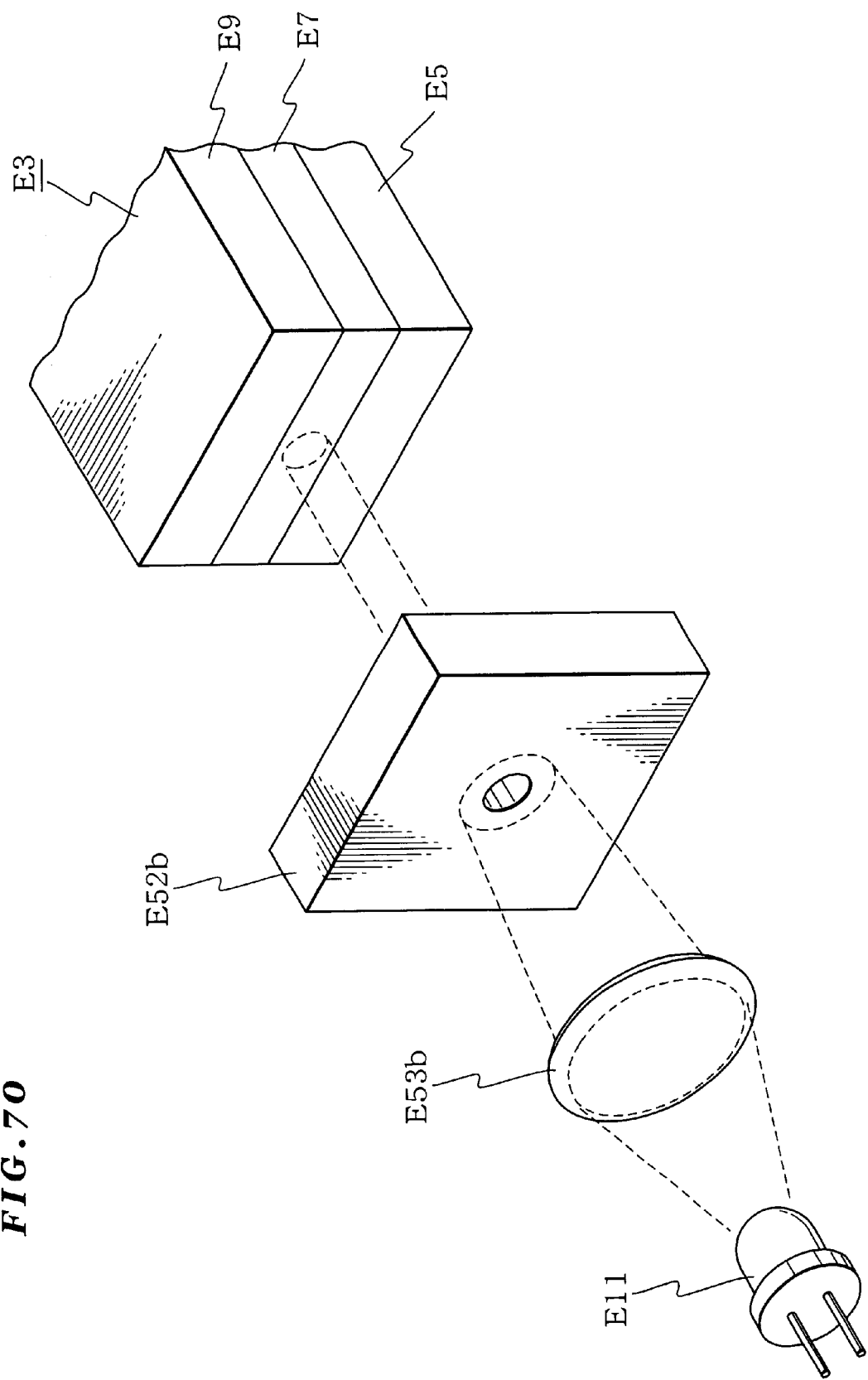
FIG. 70 schematically shows an optical path from the light source to the SPR sensor cell.

Moreover, FIG. 70 shows a case when the light from the light source E11 is converged by the converging lens E53 to a diameter slightly greater than the diameter of the pin hole of the pin hole plate E52b. In this case, setting of the optical axis with respect to the pin hole becomes easier. Even if the optical axis is slightly shifted, the light can fill the entire pin hole, and the light necessary for an immunoassay can reach the core E7.

Modified Examples of Embodiment 26

Figure 71:
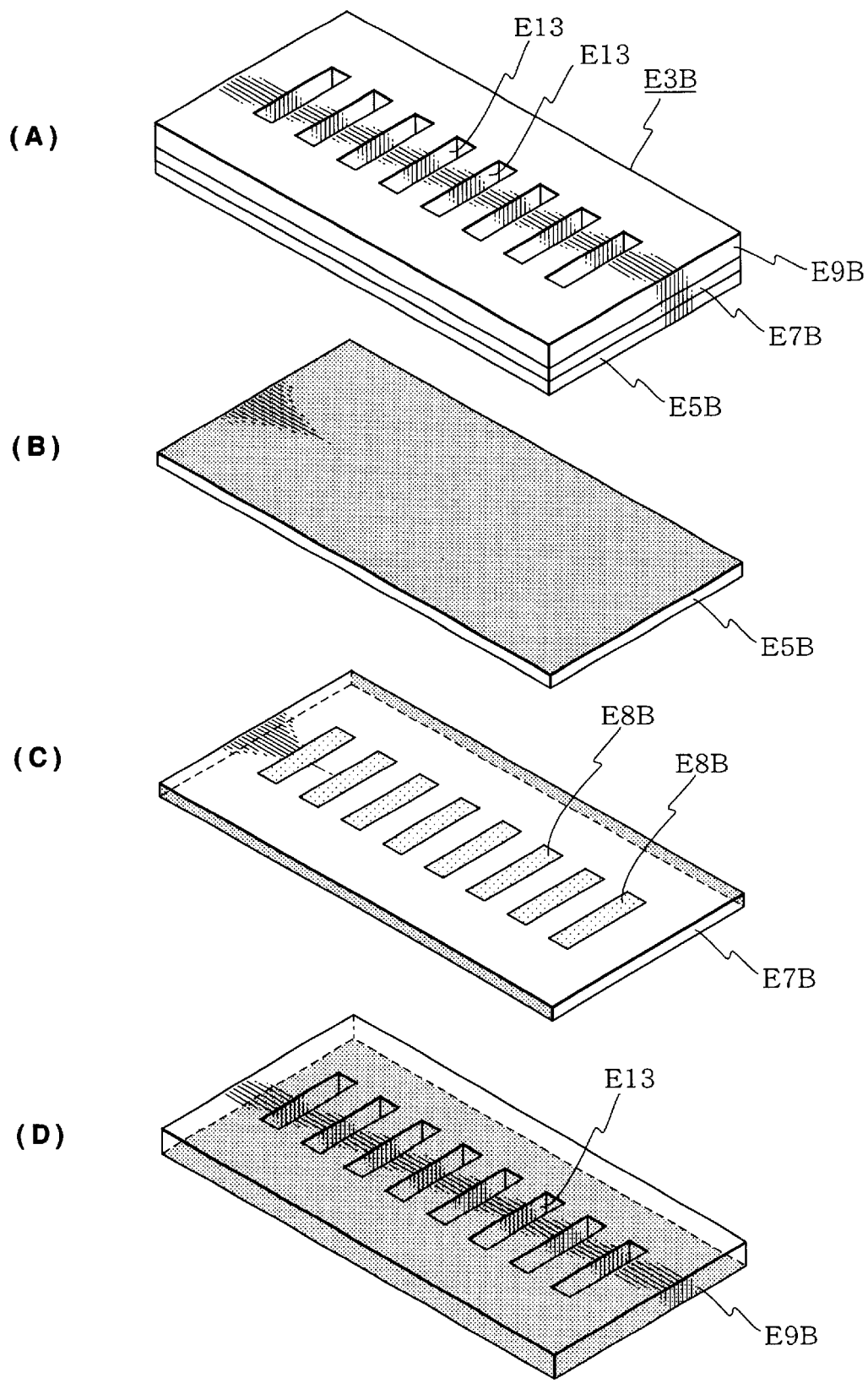
FIG. 71 shows a modified example of the SPR sensor cell.

FIG. 71 shows a modified example of the SPR sensor cell of Embodiment 26. This SPR sensor cell E3B has eight sample reservoirs. More specifically, a core E7B is placed on the first clad E5B, and on the upper surface of this core E7B, the second clad E9B is mounted. The second clad E9B has eight through holes E13 reaching the upper surface of the core E7B. That is, the upper surface of the core E7B serves as the bottoms the sample reservoirs. These bottoms serve as the SPR sensing portion. Similarly as in the aforementioned embodiment 26, the sensing portion is constituted by the core surface coated with a thin metal film and a dielectric film to which an antibody (or antigen) is attached.

When using the SPR sensor cell E3B having a sheet-shaped core E7B and a plurality of sample reservoirs, it is possible to perform various immunoassays (for different antigen or antibody) in a short time. Although the explanations has been given for a case having eight sample reservoirs, the number of the sample reservoirs may be two to seven or more than eight.

Figure 72:
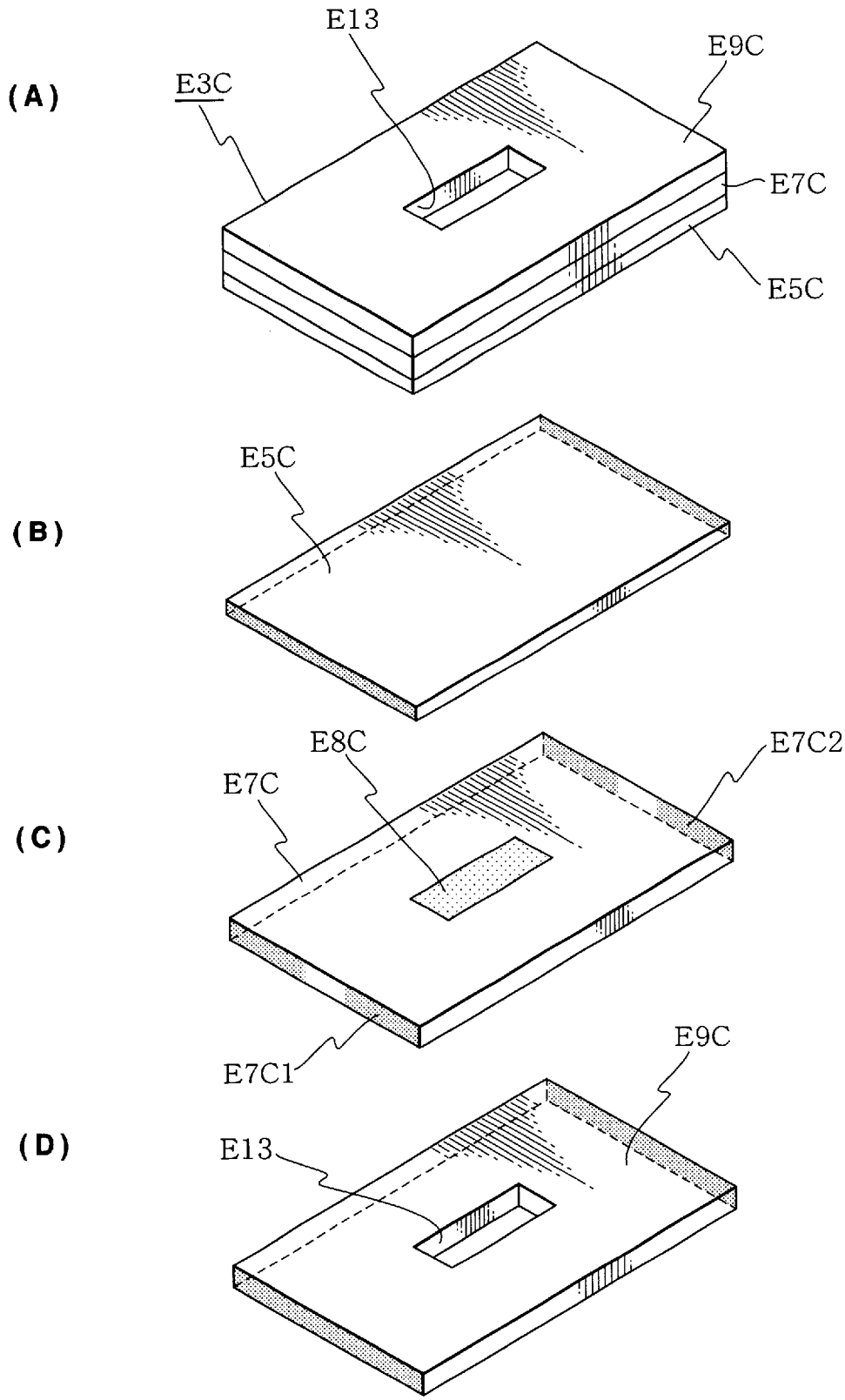
FIG. 72 shows another example of the SPR sensor cell.

FIG. 72 shows another modification of the SPR sensor cell of Embodiment 26. In this example, the core E7C has surfaces partially subjected to surface treatment. More specifically, surface treatment is performed to the end surfaces E7C1 from where the light comes into the SPR sensor cell and the end surface E7C2 from where the light goes out, excluding center portions corresponding to the position of the through hole E13. The surface treatment may be obscuring, or aluminum coating, or black paint application. This surface treatment is performed so that unnecessary light cannot intrude into the core E7C.

Moreover, the first clad E5C and the second clad E9C are also subjected to the surface treatment. More specifically, the first clad E5C and the second clad E9C have end surfaces which have been subjected to the aforementioned surface treatment. This eliminates unnecessary light coming into the first clad E5C and the second clad E9C. If an unnecessary light comes into the core E7C, this causes adverse affect to the accuracy of the immunoassay.

Figure 73:
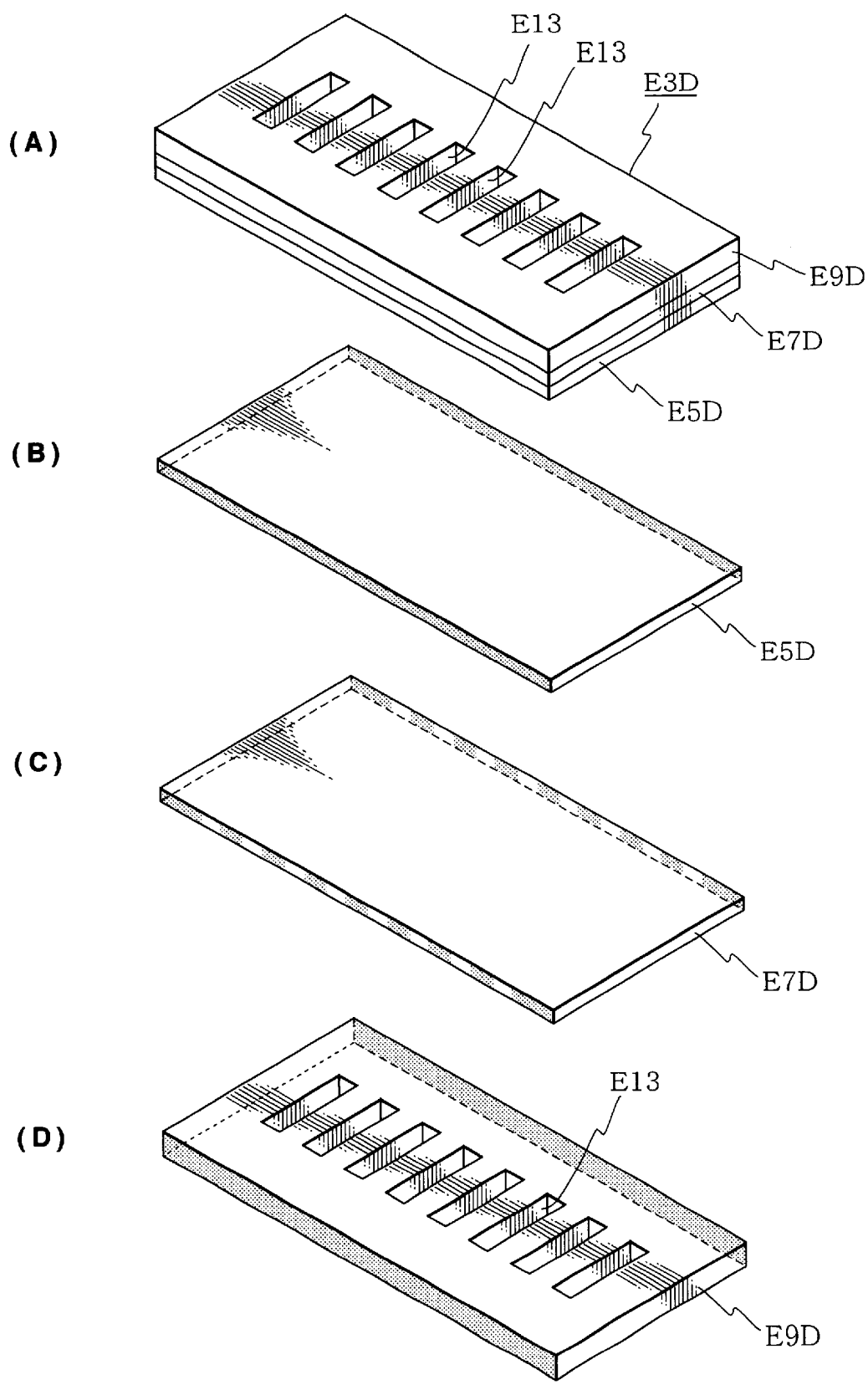
FIG. 73 shows still another example of the SPR sensor cell.

FIG. 73 shows a yet another modification of an SPR sensor cell E3D having eight through holes E13 corresponding to eight sensing portions. In this SPR sensor cell E3D, the core E7D are partially subjected to a surface treatment excluding the positions corresponding to the respective through holes E13.

Figure 74:
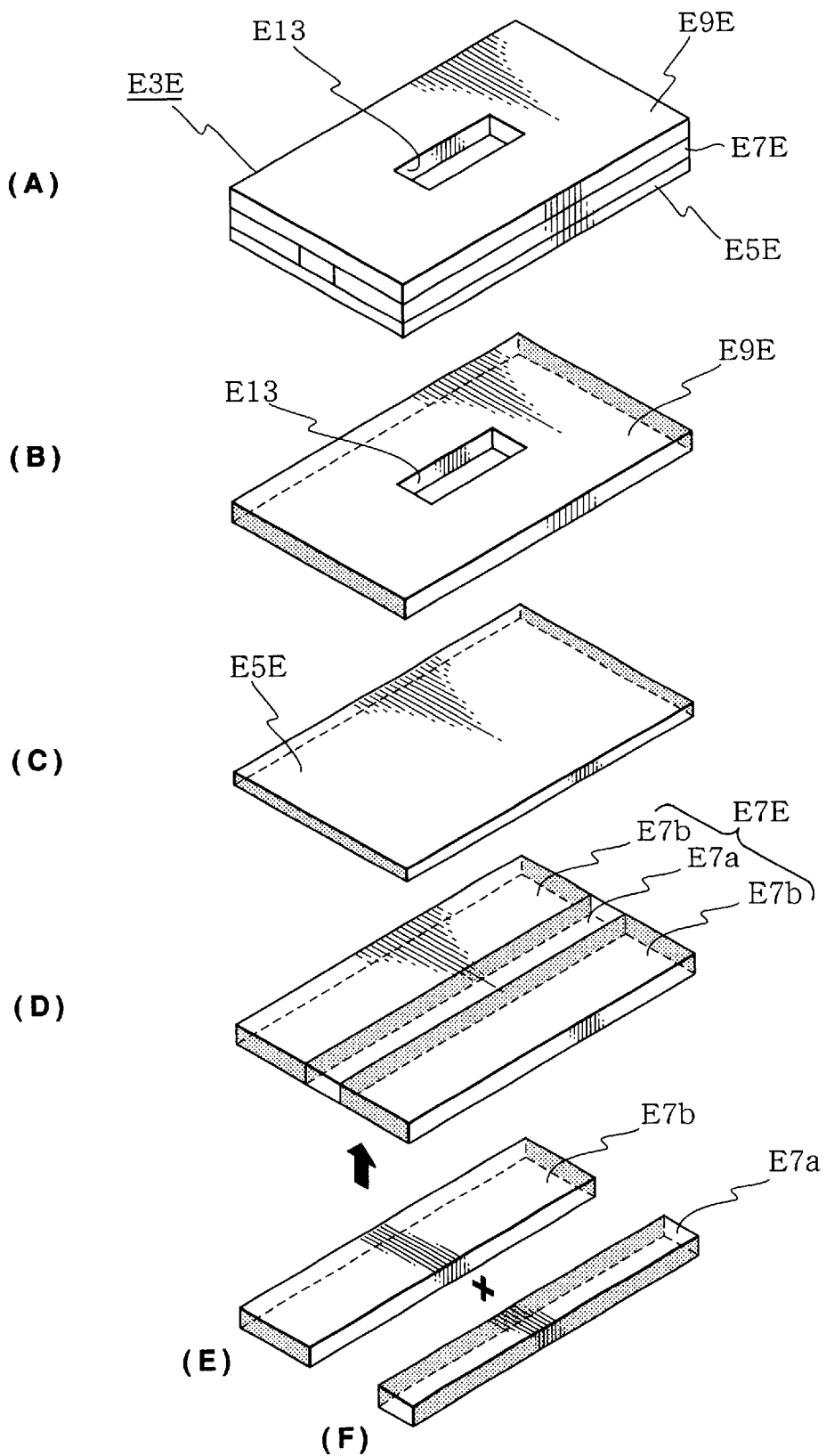
FIG. 74 shows yet another example of the SPR sensor cell.

FIG. 74 shows yet another modification of the SPR sensor cell E3D. This SPR sensor cell E3E has a core E7E divided into three members which are made from an identical light-transparent material. As shown in FIG. 74D, the core E7E is constituted by a light-transparent core E7a which is sandwiched by the two side cores E7b. As shown in FIG. 74F, the light-transparent core E7a has two opposing sides which have been subjected to a surface treatment so that the light reflection will not be caused by these two sides. The side cores E7b are attached to these opposing sides of the light-transparent core E7a, by using an adhesive or heat for melting. And surface treatment is applied to each end surfaces of the side cores E7b not to through the light. Also, surface treatment is applied to side surface of the side core E7b not to reflect the light.

FIG. 75A shows an SPR sensor cell E3F having two light-transparent cores for passing light and four non-light-passing cores which are arranged alternately as shown in FIG. 75D. More specifically, the non-light transparent cores are divided into two longer corers E7F1 shown in FIG. 75E and two shorter cores E7F3 shown in FIG. 75G. The shorter cores E7F3 are arranged in the longitudinal direction at a predetermined distance from each other. These shorter cores E7F3 are sandwiched from both sides by the light-transparent cores E7F2, which are further sandwiched by longer cores E7F1.

In FIG. 75D, void space serving as a sample reservoir is defined by width of the shorter cores and the distance between the shorter cores. Each of the light-transparent cores E7F2 has one side serving as a wall of the sample reservoir. These sides serve as SPR sensing portions. Accordingly, the both sides of the light-transparent cores E7F2 have been polished smooth. On the other hand, the upper and lower surfaces of the light-transparent cores have been subjected to a surface treatment so as to suppress the light reflection.

Figure 75:
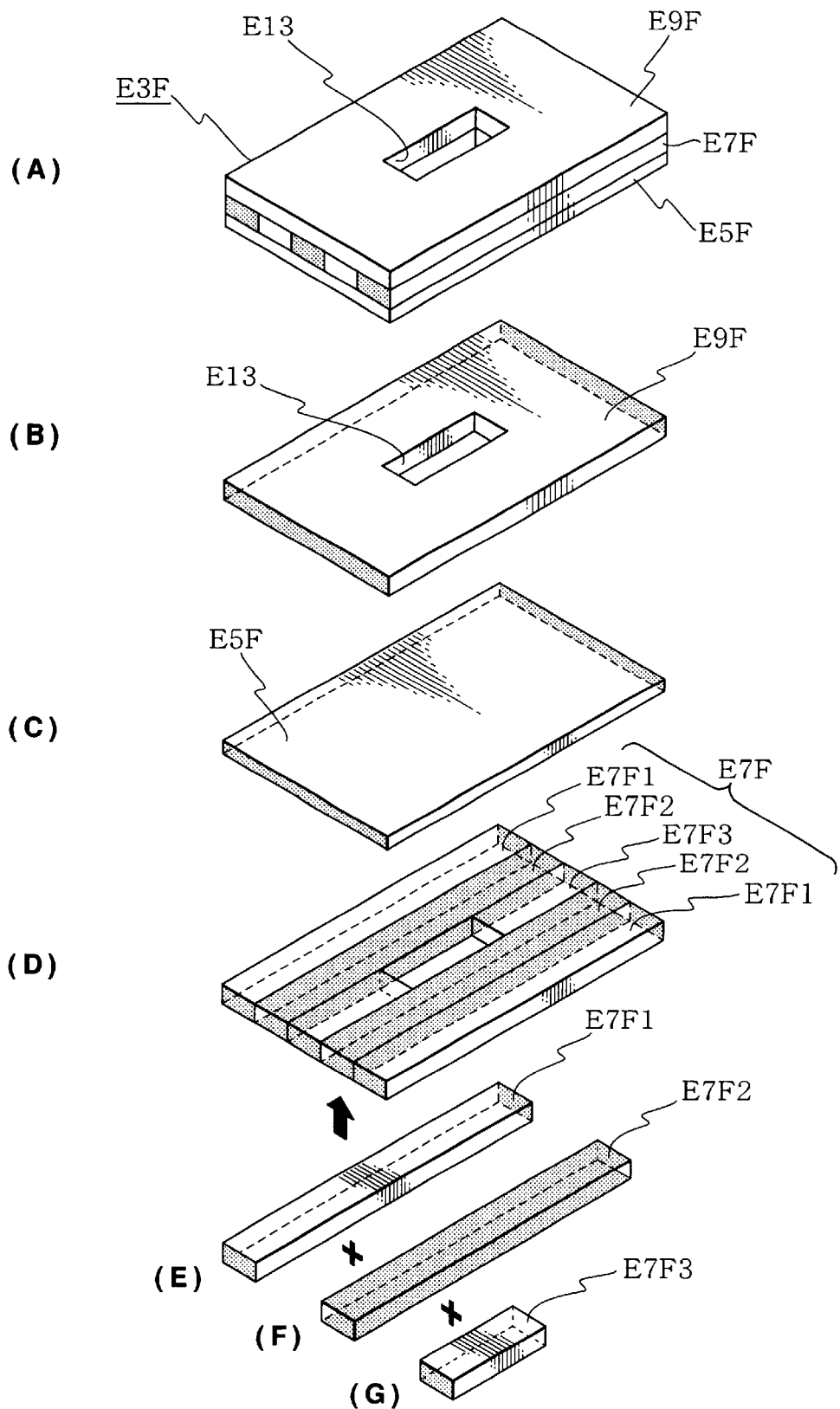
FIG. 75 shows yet another example of the SPR sensor cell.

It should be noted that the SPR sensor cell E3E shown in FIG. 74 and the SPR sensor cell E3F shown in FIG. 75, all the cores excluding the light-transparent cores, have end surfaces which have been subjected to a surface treatment so as to eliminate intrusion of light, by way of obscuring, aluminum coating, black paint application, or the like.

Figure 76:
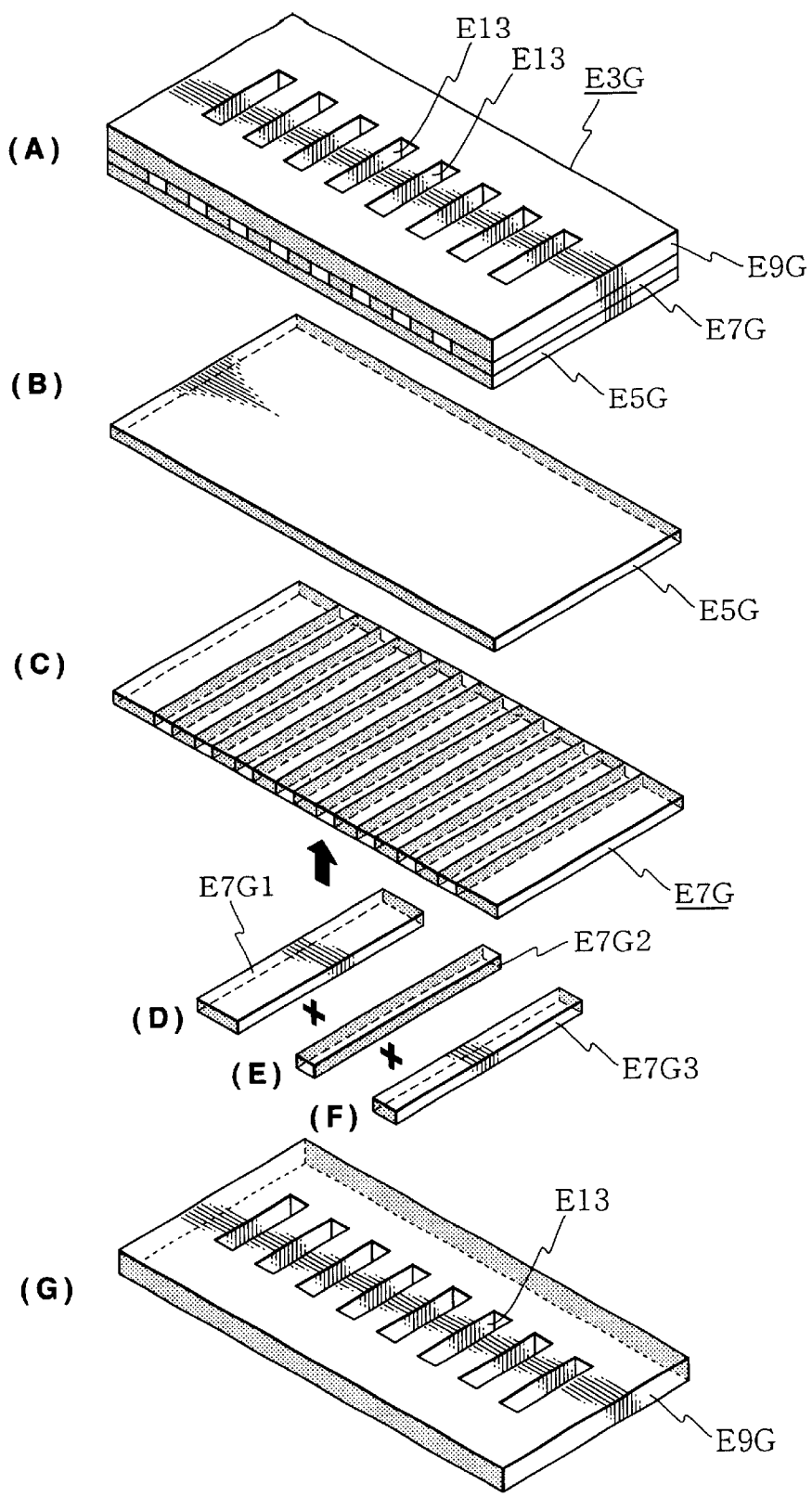
FIG. 76 shows yet still another example of the SPR sensor cell.

FIG. 76 shows an SPR sensor cell E3G having eight light-transparent cores for passing light, i.e., eight of the light-transparent cores E7G2 shown in FIG. 76E, which are alternately arranged with non-light transparent intermediate cores E7G3. Moreover, these alternating cores are sandwiched by two non-light-transparent side cores E7G1. Each of the light-transparent cores has two side surfaces which have been subjected to the aforementioned surface treatment. Furthermore, the intermediate cores and the side cores have end surfaces subjected to the surface treatment.

The aforementioned cores, i.e., the light-transparent cores and non-light transparent cores (intermediate cores and side cores) are attached to one another, constituting a sheet-shaped core E7G, which is attached onto the upper surface of the first clad E5G. And the second clad E9G is attached onto the upper surface of the cores (assembly) EG7. The second clad E7G has through holes 13 at the positions corresponding to the light-transparent cores E7G2. These through holes 13 and the upper surface of the light-transparent cores E7G2 define sample reservoirs. The surfaces of the light-transparent cores E7G2 exposed to the through hole E13 are covered with a thin metal film and a dielectric film (not depicted) so as to serve as the SPR sensing portions. With the aforementioned configuration of the SPR sensor cell, it is possible to successively perform eight immunoassays. Note that the number of the light-transparent cores E7G2 is not to be limited to eight but may bee smaller than or greater than eight.

As has been described above, the different core members may be produced from one and same material. This contributes reduction of production cost. Moreover, when performing a surface treatment or polishing for smoothness, it is possible to set like processing conditions because the material has the same characteristics (hardness, fragility, surface smoothness).

Embodiment 27

Figure 77:
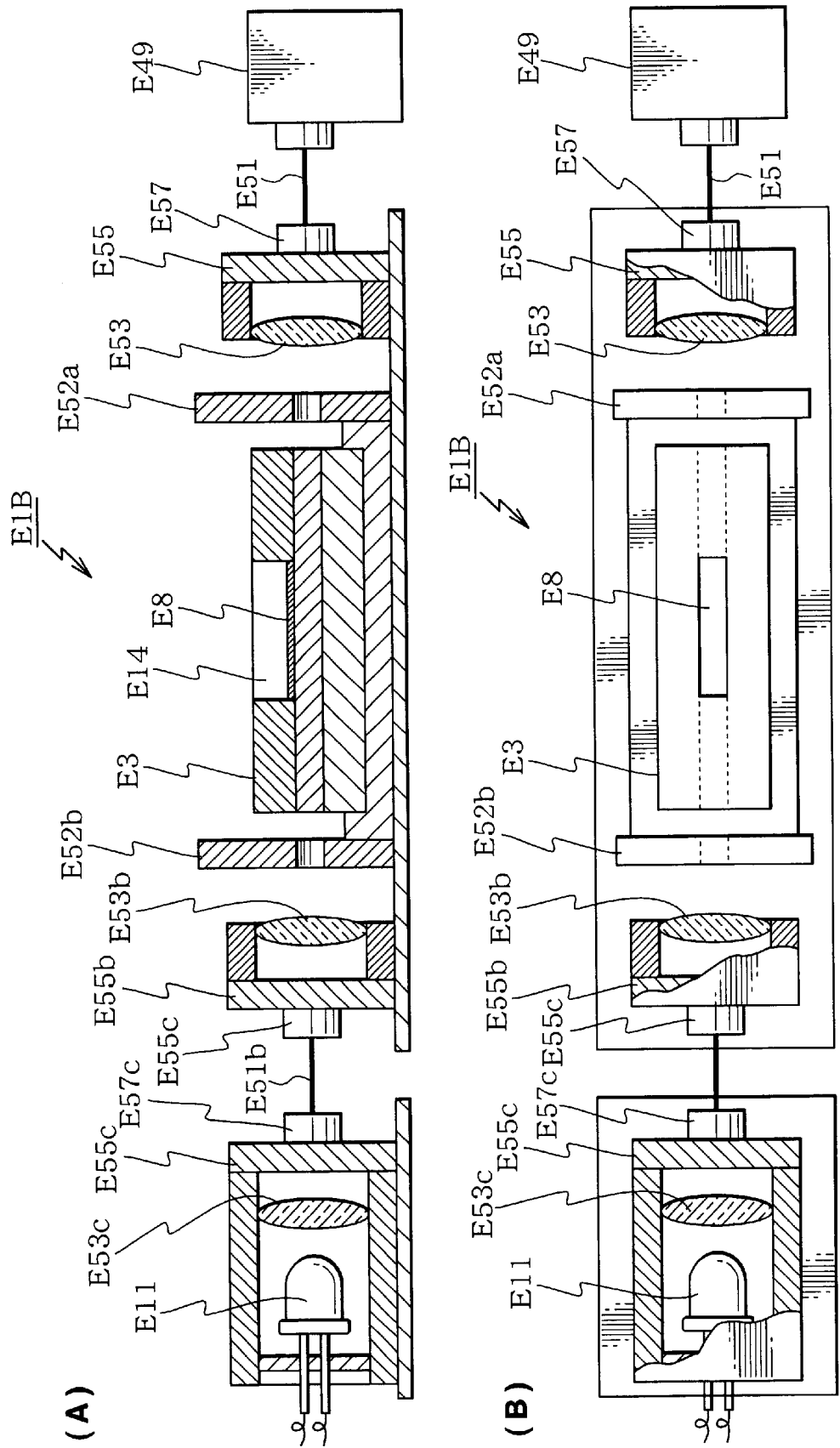
FIG. 77 shows an entire configuration of an immunoassay apparatus according to Embodiment 27.

FIG. 77A is a side view and FIG. 77B is a plan view of an immunoassay apparatus E1B according to another embodiment of the present invention. This immunoassay apparatus E1B has almost identical configuration as the immunoassay apparatus E1 shown in FIG. 67, except for that an optical fiber E51b is provided between the light source E11 and the converging lens E53b. More specifically, the light emitted from the light source E11 is converged by the converging lens E53C and passes through the receptacle E55c before coming into the optical fiber E51b.

The light which has passed through the optical fiber then passes through a receptacle E55b and comes into a converging lens E53b. The converged light further passes through a pin hole plate E52b before entering the SPR sensor cell E3. After this, the aforementioned process is performed for an immunoassay.

When the light source E11 is connected to the SPR sensor cell E3 via the optical fiber E51b. The light source E11 and the SPR sensor cell E3 can be arranged in various layouts. Moreover, optical connectors E55C and E57c are used for connection of the optical fiber E51b. Accordingly, it is possible to readily detach the light source E11 and the SPR sensor cell E3.

Embodiment 28

Figure 78:
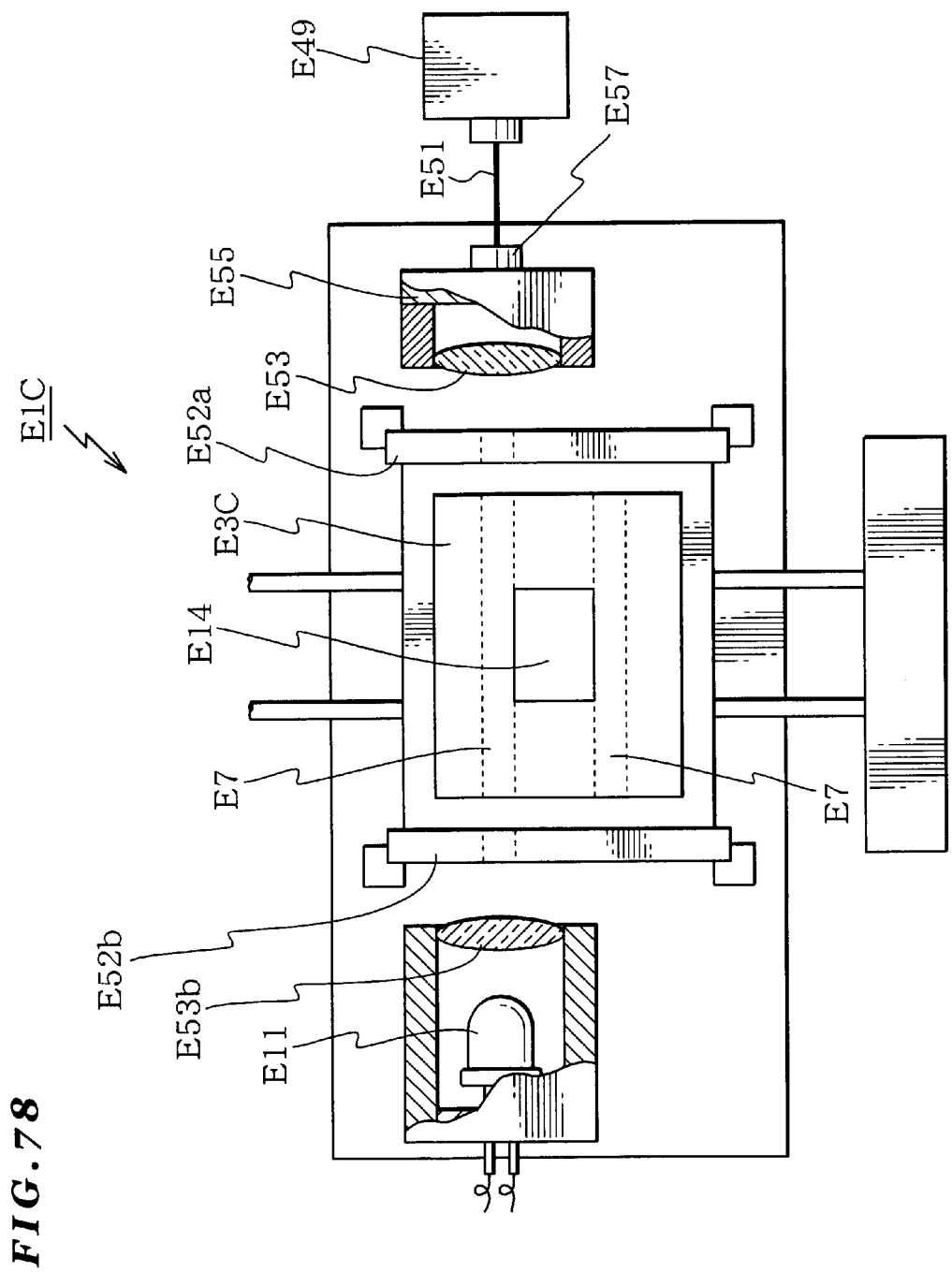
FIG. 78 shows an entire configuration of an immunoassay apparatus according to Embodiment 28.

FIG. 78 is a plan view of an immunoassay apparatus E1C comprising an SPR sensor cell E3C having two light-transparent cores E7. As shown in this figure, a sample reservoir E14 is formed between the two light-transparent cores E7. The SPR sensor cell E3C itself are mounted on a predetermined pair of rails so as to be movable in a direction vertical to the optical axis from the light source E11 to the SPR sensor cell E3C.

Moreover, the SPR sensor cell E3C is sandwiched by two pin hole plates E52a and E52b. The pin hole plates are fixed to predetermined positions with respect to the light source E11. That is, the SPR sensor cell E3C is moved in relation to the pin hole plates E52a and E52b.

In FIG. 78, one of the two cores E7 is positioned to match with the optical axis of the light source E11. In this state, the light analyzing means checks the wavelength distribution of the light passing through the SPR sensor cell E3, thus performing an immunoassay. Next, the SPR sensor cell E3 is moved (upward in this figure) and stopped where the other core E7 is matched with the optical axis of the light source E11 for another immunoassay.

Embodiment 29

Figure 79:
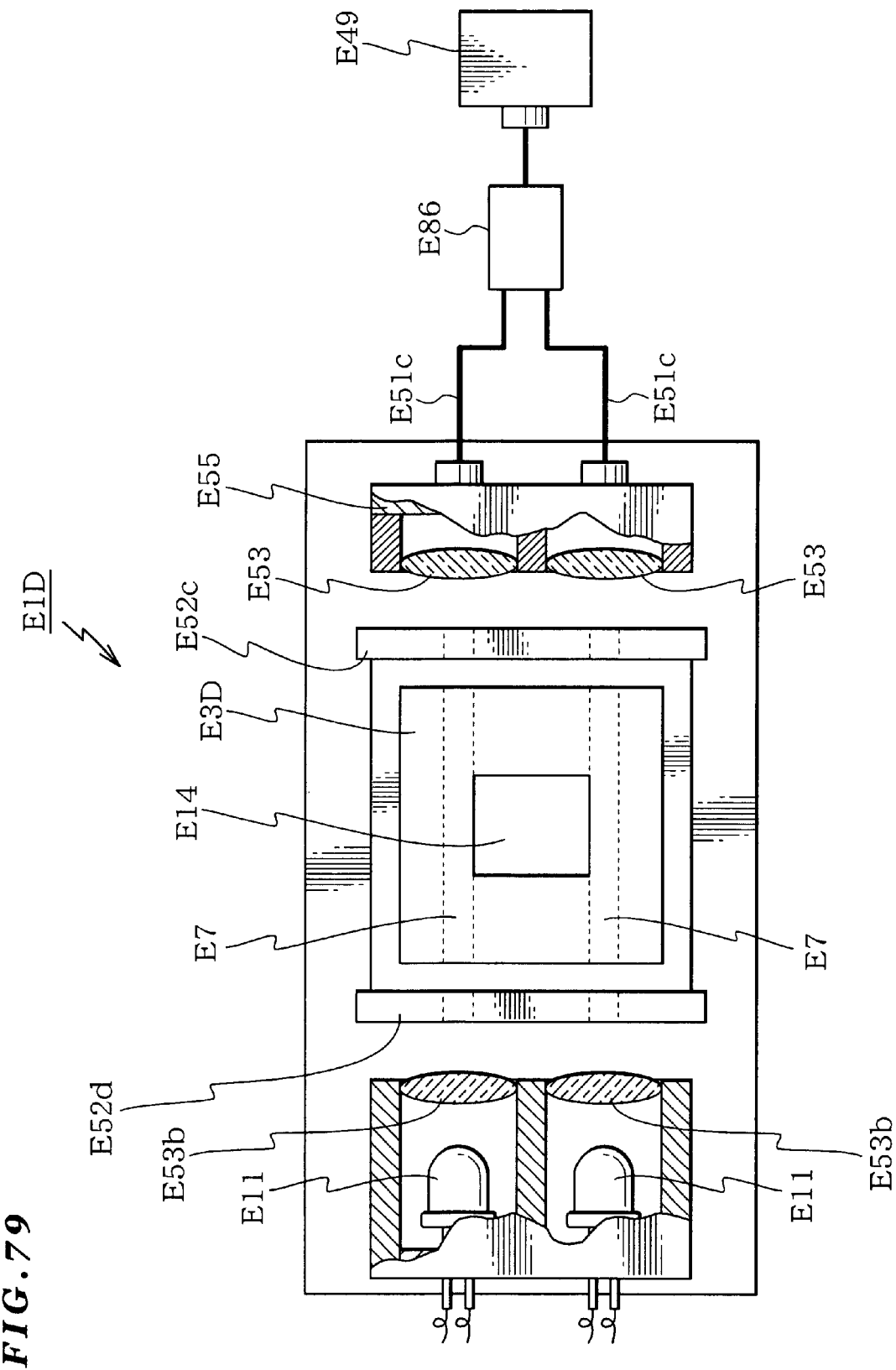
FIG. 79 shows an entire configuration of an immunoassay apparatus according to Embodiment 29.

FIG. 79 is a plan view of an immunoassay apparatus E1D comprising: two light-transparent cores E7, two light sources E11, two first converging lenses E53b, an SPR sensor having two light transparent cores E7, two second converging lenses E53, an optical coupler E86, and light analyzing means E49. In this immunoassay apparatus E1D, the two light sources E11 are switched to each other for performing an immunoassay using a corresponding one of the light-transparent cores. The light from the light source E11 enters the light analyzing means E49 through one of the intermediate optical fibers E51c which are connected to the optical coupler E86.

The immunoassay apparatus E1D further comprises two pin hole plates E52c and E52d, each having two pin holes corresponding to the light-transparent cores E7.

Thus, when there are two sets of optical systems are provided, the SPR sensor cell E3D need not be moved. The immunoassay apparatus E1D can be easily constituted and an immunoassay can be performed rapidly.

Embodiment 30

Figure 80:
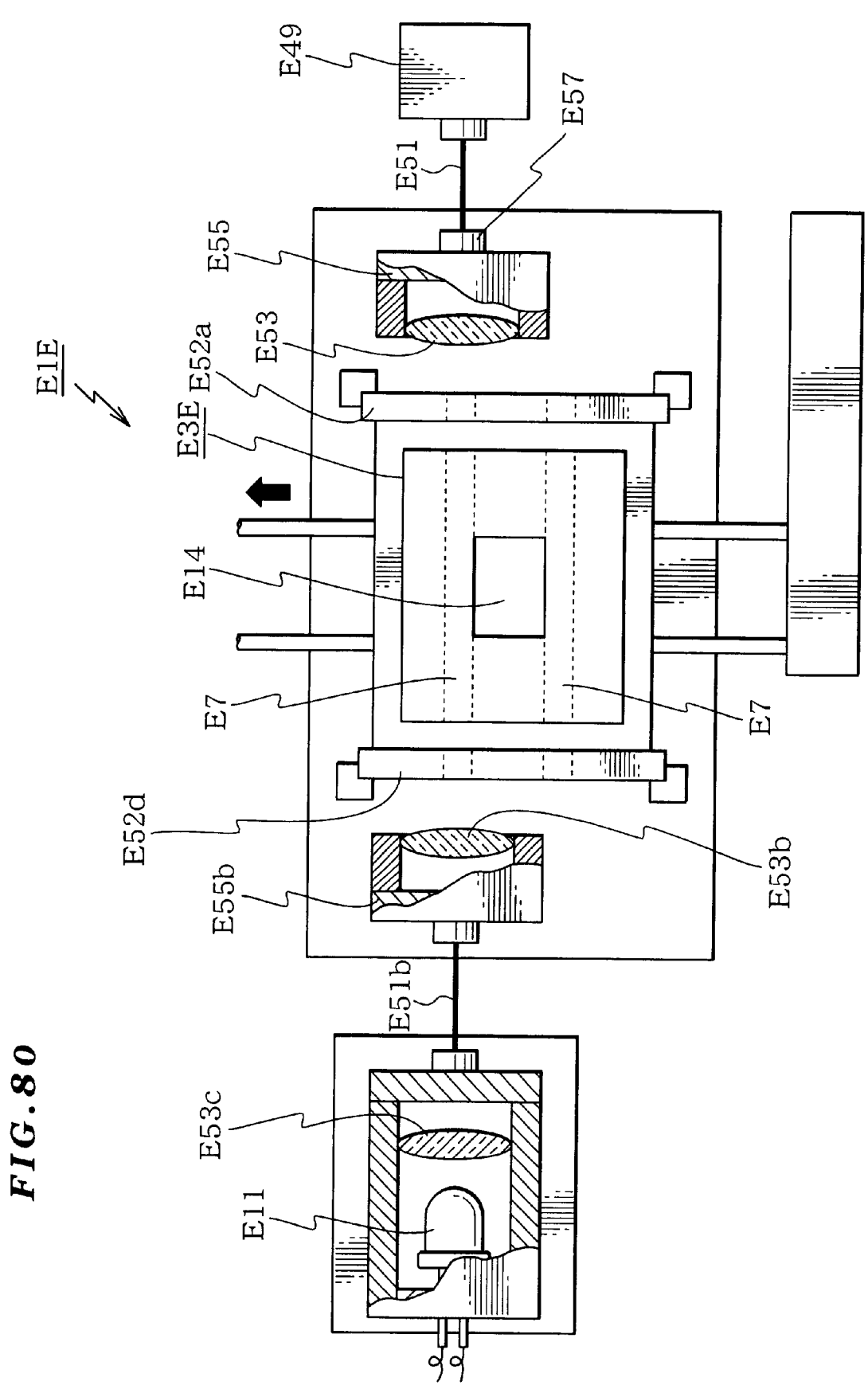
FIG. 80 shows an entire configuration of an immunoassay apparatus according to Embodiment 30.

FIG. 80 shows a modified example of the immunoassay apparatus shown in FIG. 78. In this modified example, there is provided an optical fiber E51b between the light source E11 and the SPR sensor cell E3E.

Embodiment 31

Figure 81:
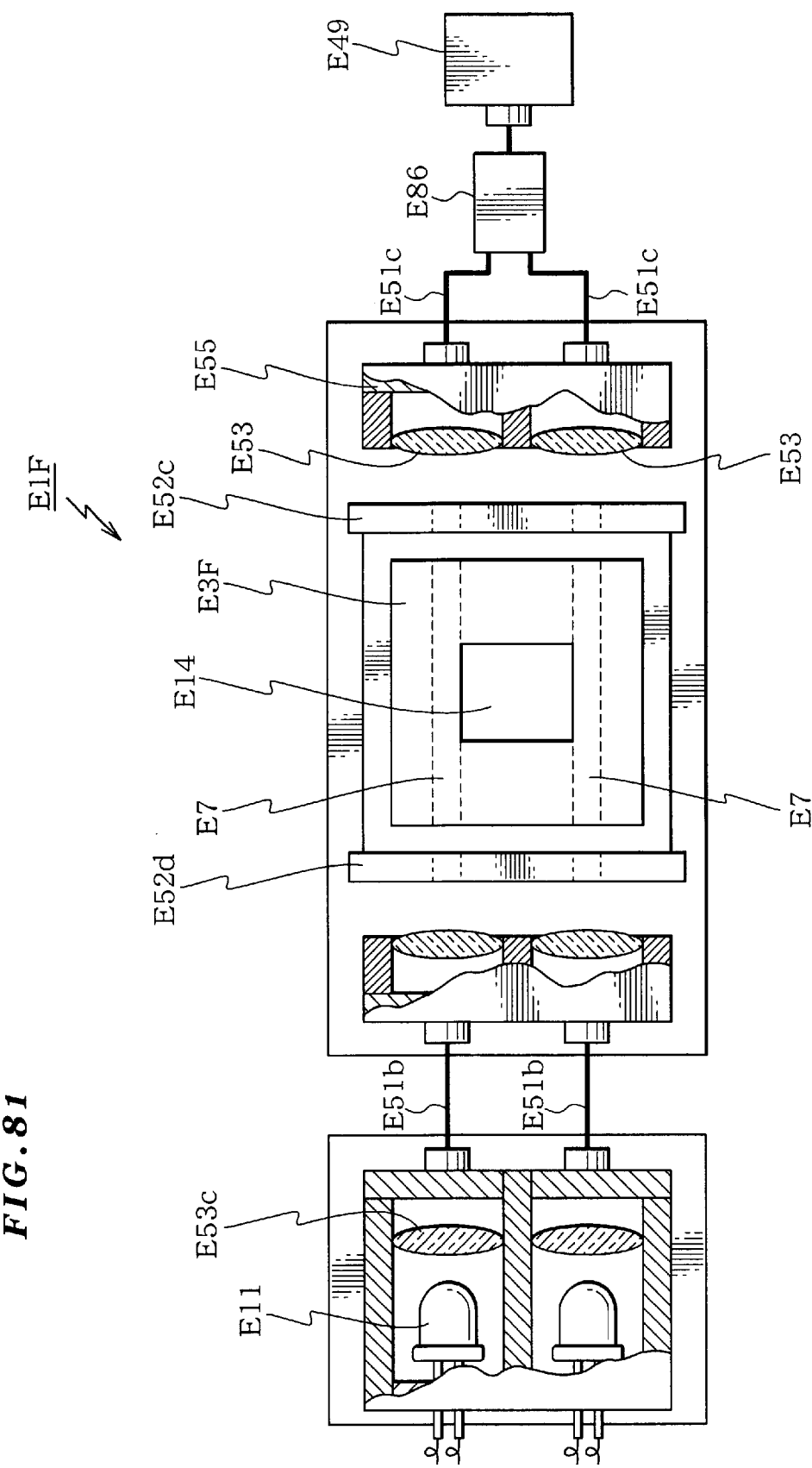
FIG. 81 shows an entire configuration of an immunoassay apparatus according to Embodiment 31.

FIG. 81 shows a modified example of the immunoassay apparatus shown in FIG. 79. In this modified example, an optical fiber E51b is provided between the light source E11 and the SPR sensor cell E3F.

Embodiment 32

Figure 82:
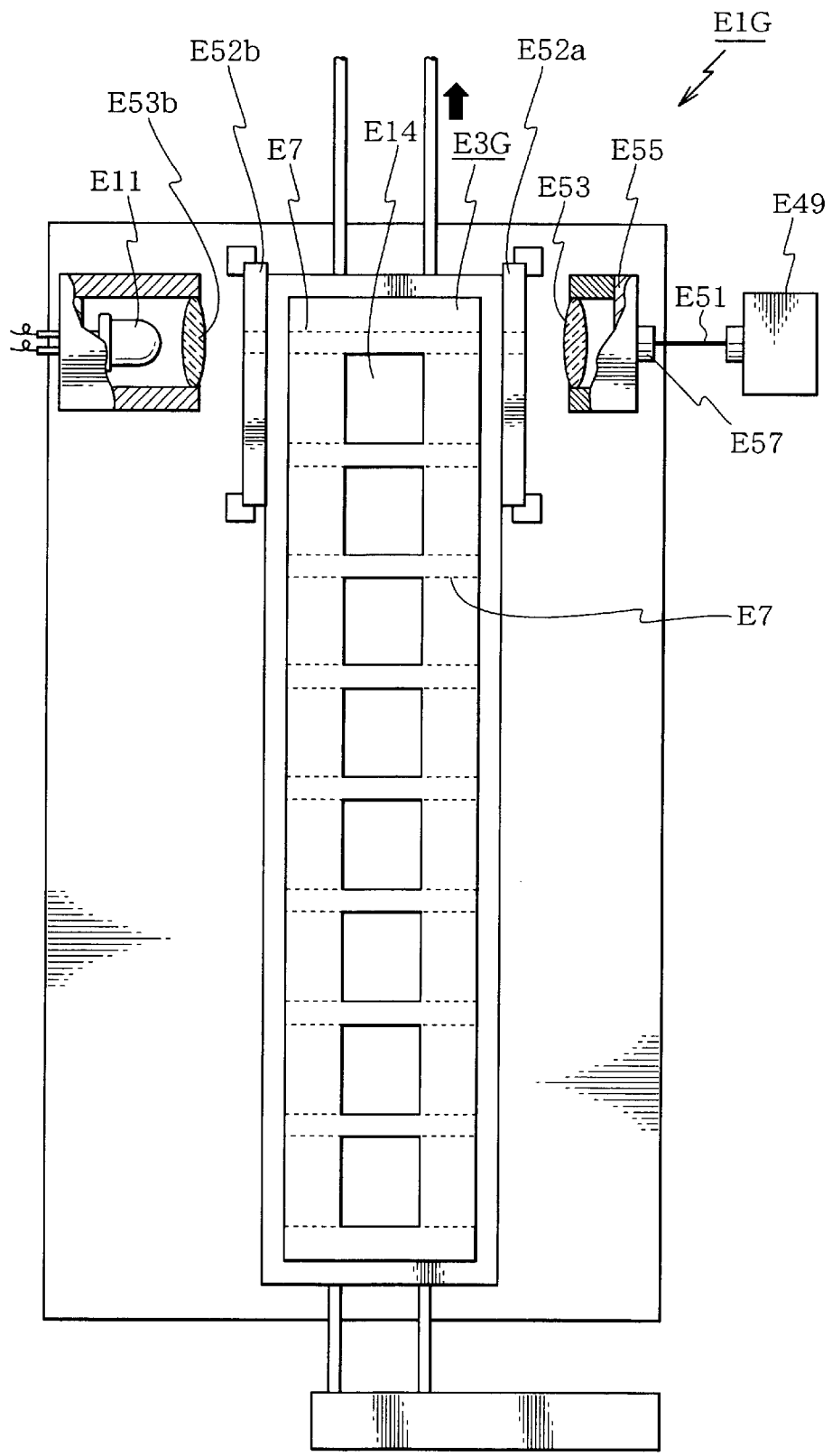
FIG. 82 shows an entire configuration of an immunoassay apparatus according to Embodiment 32.

FIG. 82 shows an immunoassay apparatus identical to the immunoassay apparatus shown in FIG. 78 except for that the SPR sensor cell is replaced by an SPR sensor E3G having eight light-transparent cores E7. This SPR sensor E3G is mounted on a predetermined pair of rails so that the SPR sensor E3G can move along the rails. The light source E11 emits light which is converged by the converging lens E53b and introduced into one of the light-transparent core of the SPR sensor cell E3G. The light coming out of the SPR sensor cell E3G passes through the converging lens E53 and the optical fiber E51 before entering the light analyzing means.

Embodiment 33

Figure 83:
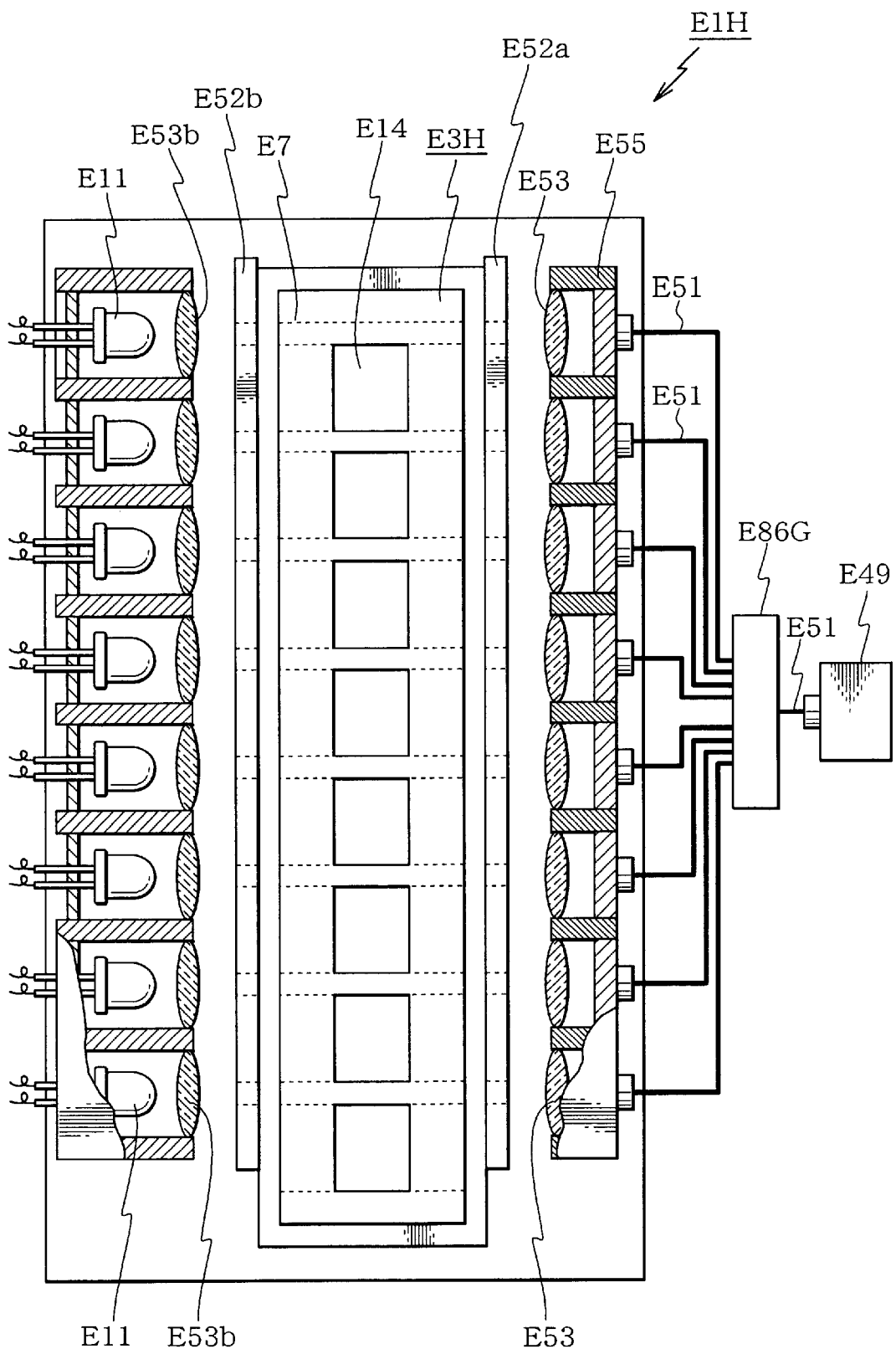
FIG. 83 shows an entire configuration of an immunoassay apparatus according to Embodiment 33.

FIG. 83 shows an immunoassay apparatus E1H having a configuration identical to the immunoassay apparatus of FIG. 79 except for that eight sets of light sources E11 converging lenses E53b and E53, and optical fibers E51C are provided instead of two sets. At both sides of the SPR sensor cell E3H, there are provided eight sets of pin hole plates E52a and E52b corresponding to the respective light sources E11 and the converging lenses E53 and E53b. The eight sets of pin hole plates E52a and E52b are fixed with respect to the SPR sensor cell E3H. It should be noted that only one of the light sources E11 is turned on at a time. That is, immunoassay is performed by one of the cores E7.

Embodiment 34

Figure 84:
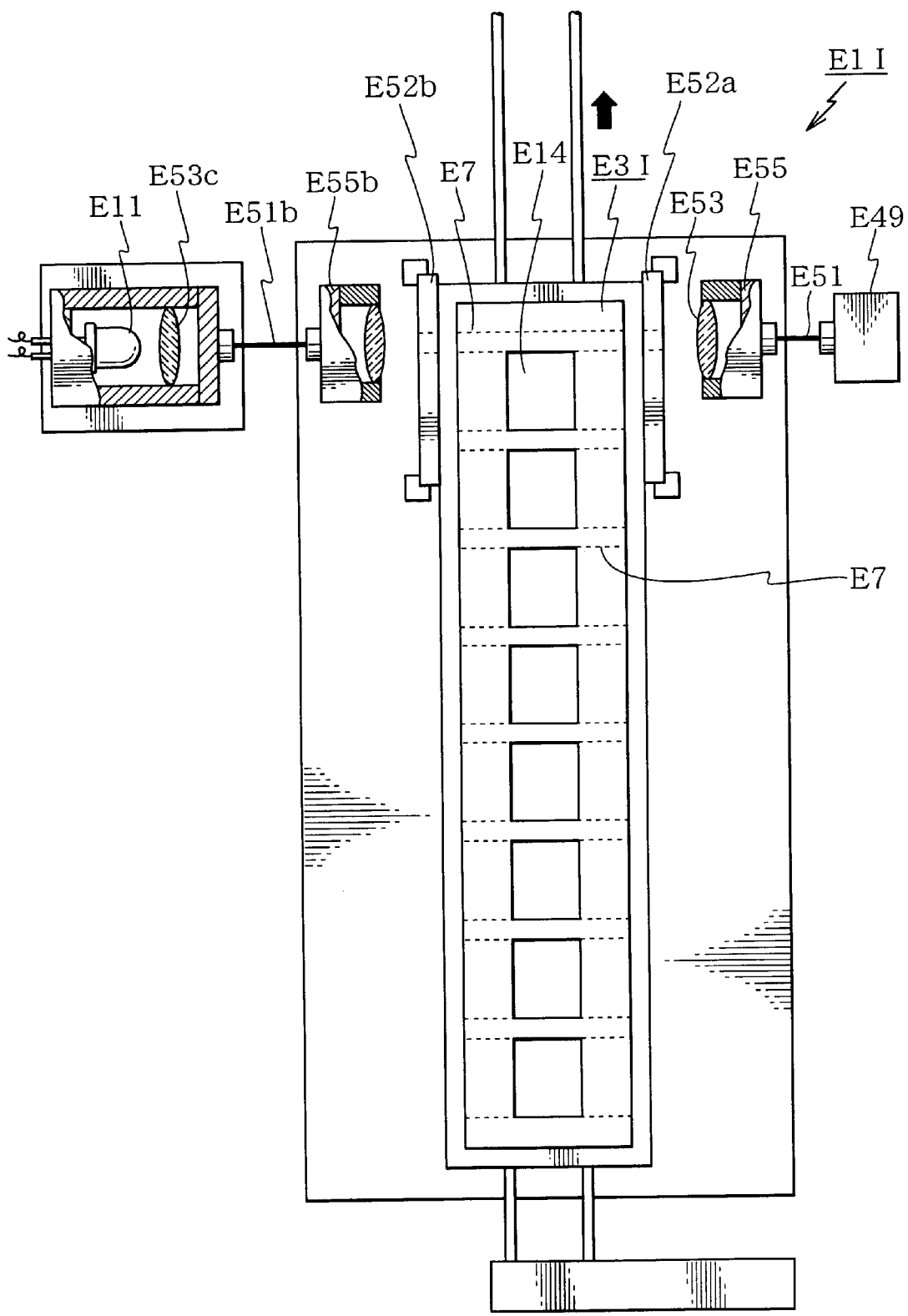
FIG. 84 shows an entire configuration of an immunoassay apparatus according to Embodiment 34.

FIG. 84 shows an immunoassay apparatus as a modified example of the immunoassay apparatus shown in FIG. 80. This modified example uses an SPR sensor cell E3I having eight cores E7.

Embodiment 35

Figure 85:
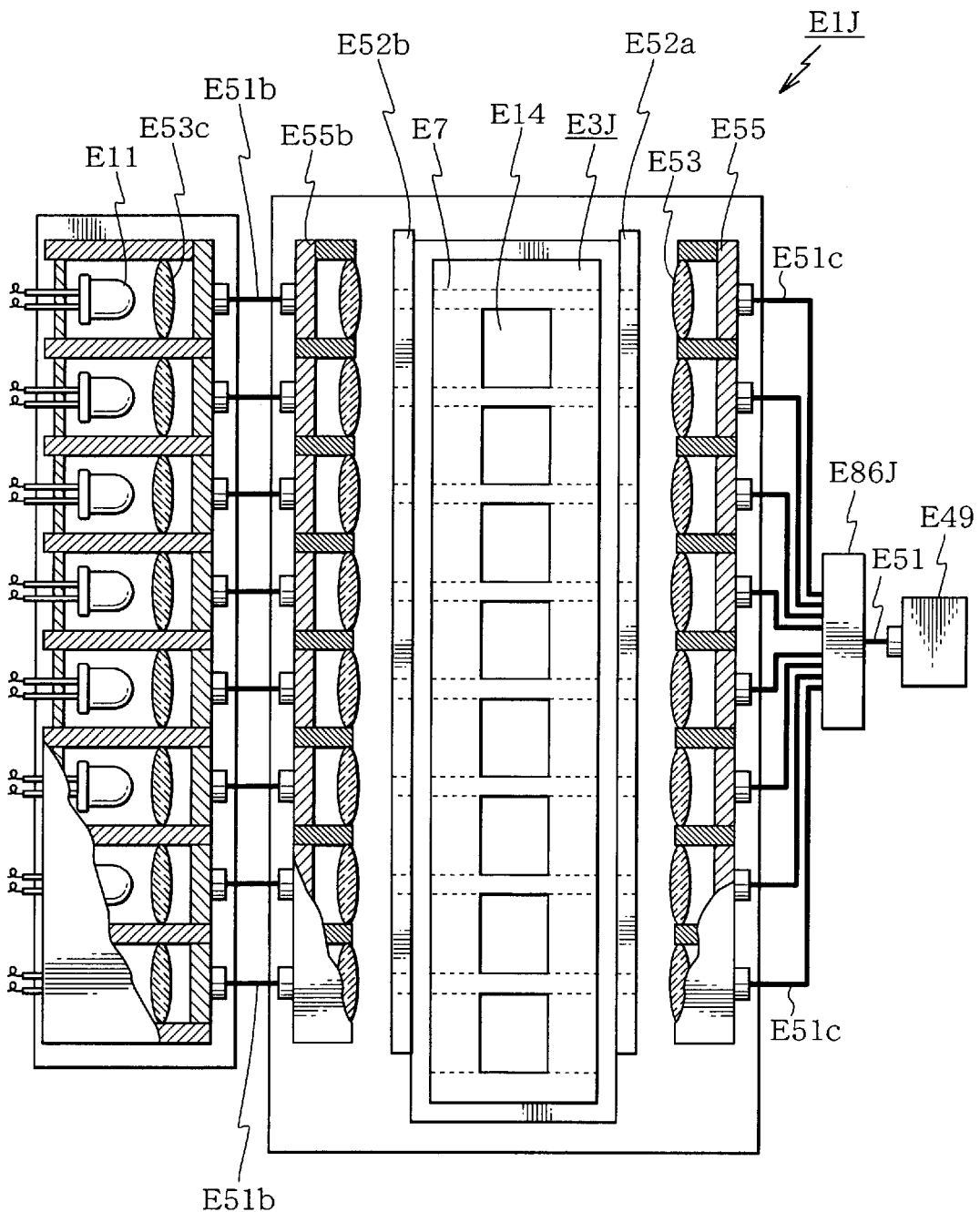
FIG. 85 shows an entire configuration of an immunoassay apparatus according to Embodiment 35.

FIG. 85 shows an immunoassay apparatus E1J which is identical to the immunoassay apparatus of FIG. 81, except for that eight sets of light sources E11, converging lenses E53c, E53, and eight sets of light-transparent cores E7.

Embodiment 36

Figure 86:
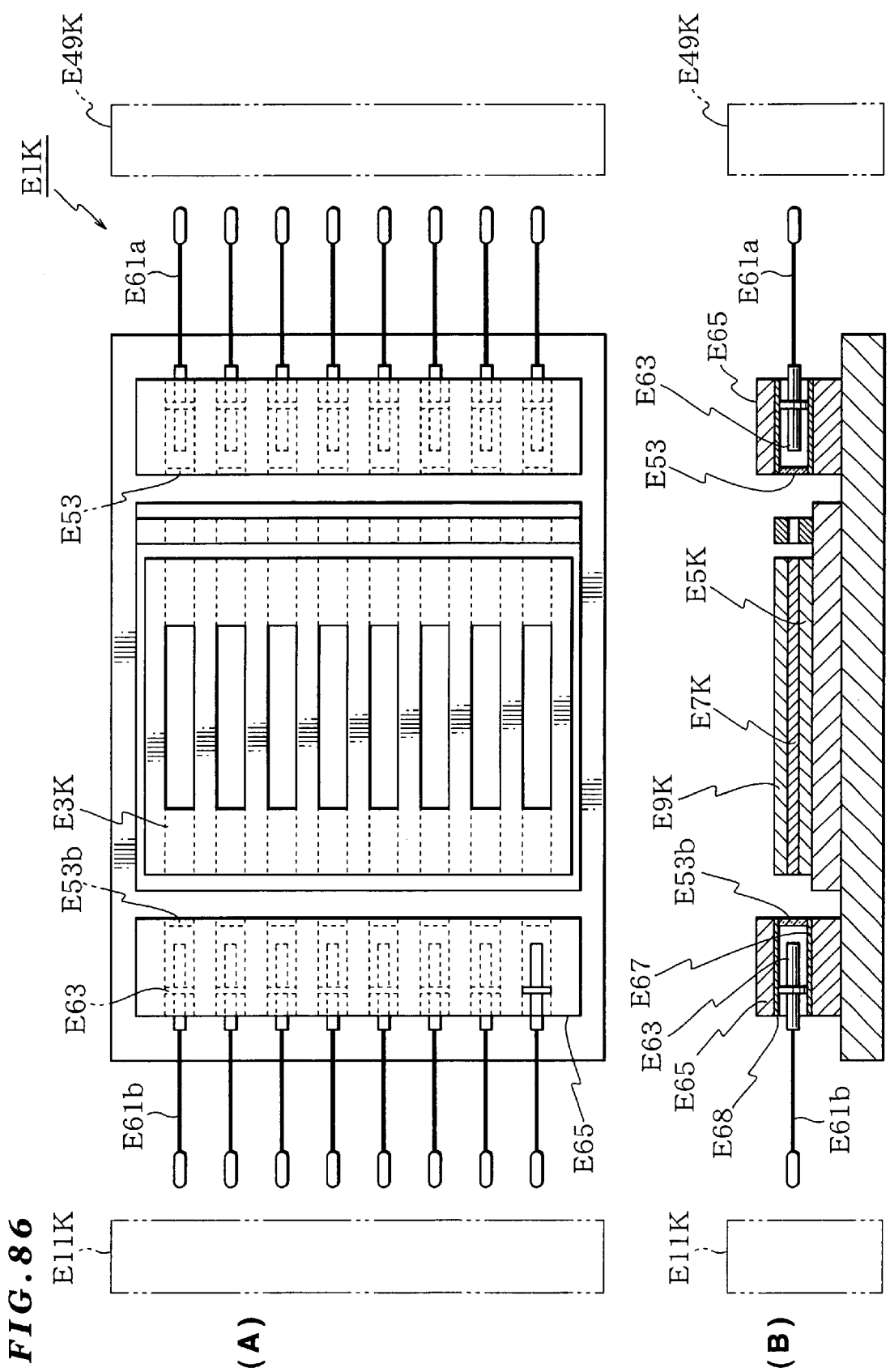
FIG. 86 shows an entire configuration of an immunoassay apparatus according to Embodiment 36.

FIG. 86 shows an immunoassay apparatus according to Embodiment 36. FIG. 86A is a plan view and FIG. 86B is a side view of the immunoassay apparatus E1K. As shown here, the optical fibers E61b are fixed to a block member 65 having through holes as fiber fixing portions E67 corresponding to the respective optical axes of the cores.

Each of the through holes may have a cylindrical member E68.

Moreover, each of the optical fibers 61b has an end portion covered by a ferrule E63 consisting of a cylindrical cap and a brim portion. The brim portion has a diameter slightly smaller than the inner diameter of the aforementioned cylindrical member E68. This ferrule E63 is inserted into the cylindrical member E68 arranged inside the optical fiber fixing portion E67, so as to be fixed there.

It should be noted that in FIG. 86, the cylindrical member E68 is mounted in the optical fiber fixing portion E67. The converging lens E53b and ferrule E63 are fixed in this cylindrical member E68. More specifically, the converging lens E53b is fixed in two V-shaped grooves formed on the cylindrical member E68. With this configuration, it is possible to remove the converging lens E53b and the optical fiber E61b as a unitary block.

Figure 87:
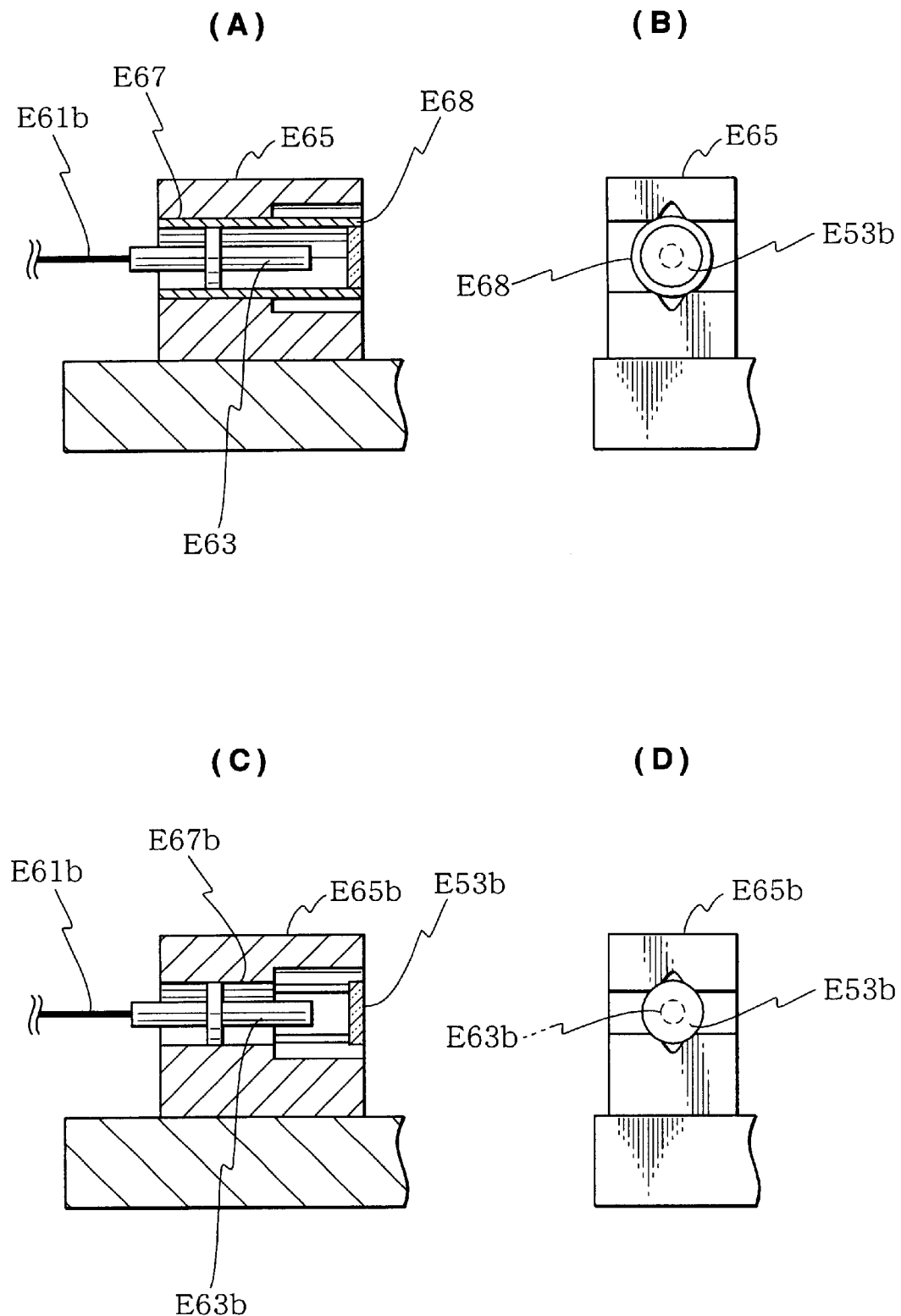
FIG. 87 is an enlarged view of an optical fiber fixing portion of the immunoassay apparatus shown in FIG. 87.

FIG. 87A and FIG. 87B are enlarged view of the optical fiber fixing portion E67 using the cylindrical member E68.

FIG. 87C and FIG. 87D shows a case not using the cylindrical member, i.e., ferrule E63 and the converging lens E53b are directly mounted in the optical fiber fixing portion E67b. In this case an upper and a lower V-shaped groove are formed on the optical fiber fixing portion E67b, for fixing the converging lens E53b.

When the aforementioned block member E65 and E65b is used, it is possible to reduce a distance between optical fibers in comparison to a case when using an optical connector of a large diameter. The block member E65 and E65b may be provided not only at the side of light source E11 but also at the light analyzing means E49k.

Embodiment 37

FIG. 88 shows an immunoassay apparatus almost identical to the immunoassay of Embodiment 36, except for that the light source E11 (white LED or halogen lamp) is fixed directly to the block member E65. This eliminates use of the plurality of optical fibers.

As has been described above, the present invention provides various advantages. A thin metal film for causing the surface plasmon resonance can be formed easily and an antibody (or antigen) can easily be fixed on this thin metal film.

The SPR sensor cell according to the present invention comprises: a sheet-shaped core transmitting light from a light source, having an SPR sensing portion, and sandwiched between a first clad and a second clad which has a through hole at a position corresponding to the SPR sensing portion. Accordingly, the SPR sensor cell has various advantages in comparison to a case using a plurality of members for the core. For example, the sheet-type core can be polished in one step, thus increasing the process efficiency. Moreover, there is no need of accurate attachment of a plurality of members to one another. This significantly reduces the SPR sensor cell production cost. Furthermore, this suppresses the irregularities between the respective SPR sensor cell.

Moreover, in this invention, the core is constituted by one light-transparent material. Accordingly, the member costs less than a case using different materials. Moreover, since the core members is made from one identical material, processing conditions (material hardness, fragility, surface smoothness) can also be set identically.

The invention may be embodied in other specific forms without departing from the spirit or essential characteristic thereof. The present embodiments are therefore to be considered in all respects as illustrative and not restrictive, the scope of the invention being indicated by the appended claims rather than by the foregoing description and all changes which come within the meaning and range of equivalency of the claims are therefore intended to be embraced therein.

The entire disclosure of Japanese Patent Application No. A10-205864 (Filed on Jul. $6^{th}$, 1998), Japanese Patent Application No. A11-32617 (Filed on Feb. $10^{th}$, 1999), Japanese Patent Application No. A11-129668 (Filed on May $11^{th}$, 1999), Japanese Patent Application No. A11-158962 (Filed on Jun. $7^{th}$, 1999) and Japanese Patent Application No. A11-169479 (Filed on Jun. $16^{th}$, 1999) including specification, claims, drawings and summary are incorporated herein by reference in its entirety.

What is claimed is:

1. An SPR sensor cell comprising an optical waveguide, said optical waveguide comprising:
    a plate-shaped first clad serving as a lower support member;
    a core provided on a top surface of said first clad; and
    a second clad to cover said core,
        wherein a through hole is formed at a predetermined position of said second clad to communicate with a predetermined portion of said core, and wherein a predetermined thin metal film is formed on an exposed predetermined portion of said core surface corresponding to said through hole.

2. An SPR sensor cell of claim 1, wherein two or more said cores are provided and said second clad has a corresponding two or more said through holes.

3. An SPR sensor cell of claim 1, wherein said core has a longitudinal axis and an exposed face at each end of said longitudinal axis and on one of said two faces a light reflection surface is formed.

4. An SPR sensor cell of claim 1, wherein said core has a longitudinal axis and an exposed face at each end of said longitudinal axis and at least one of said end face surfaces of said core is inclined with respect to said longitudinal axis.

5. An SPR sensor cell of claim 1, wherein said second clad has a predetermined thickness such that said through hole functions as a container for a material being tested.

6. An SPR sensor cell of claim 1, wherein said core has a longitudinal axis and an exposed face at each end of said longitudinal axis and said two exposed faces have different areas.

7. An SPR sensor cell comprising:
    at least two cores, each said core having a surface area serving as an SPR sensing portion;
    a clad surrounding said cores except at a first end surface and a second end surface; and
    at least one through hole formed in said clad so as to communicate simultaneously with at least two of said at least two SPR sensing portions.

8. An SPR sensor cell of claim 7, wherein said SPR sensor portion is formed at least at two locations of each said core and a plurality of said through holes are provided, wherein each said through hole is formed so as to simultaneously communicate with at least two said SPR sensing portions.

9. An SPR sensor of claim 7, wherein said clad has at least one end surface having a characteristic that reduces passage of light.

10. An immunoassay apparatus comprising:
an SPR sensor cell comprising:
at least two cores, each said core having a surface area serving as an SPR sensing portion;
a clad surrounding said cores except on two end surfaces; and
a through hole formed in said clad so as to communicate simultaneously with at least two of said SPR sensing portions;
a light source for emitting light into said cores; and
a spectrometer or photodiode for performing a wavelength distribution of the light emitted from said SPR sensor cell.

11. An immunoassay apparatus of claim 10, wherein said SPR sensing portion is formed on at least two locations of each of said cores and a plurality of said through holes are arranged so that each said through hole communicates simultaneously with adjacent SPR sensing portions on two adjacent cores.

12. An immunoassay apparatus of claim 10, wherein said light source emits light simultaneously into at least two of said at least two cores.

13. An immunoassay apparatus of claim 10, wherein said light source emits light successively into each said at least two cores.

14. An immunoassay apparatus of claim 10, wherein said light source is a white LED lamp or halogen lamp capable of emitting light of different wavelengths.

15. An immunoassay apparatus of claim 10, wherein said clad material has at least one outside surface having a characteristic that light is inhibited from passing through said outside surface.

16. An immunoassay apparatus comprising:
an SPR sensor cell having an SPR sensing portion and a through hole adjacent to said said sensing portion, wherein said through hole has a predetermined thickness dimension sufficient to permit said through hole to serve as a test material holding receptacle;
a light source for emitting light of a predetermined wavelength band into said SPR sensor cell; and
a light analyzing means for analyzing light which has passed through said SPR sensor cell,
wherein said light source comprises a white LED lamp and said SPR sensor cell comprises at least two cores and clads surrounding said cores on all sides except two end surfaces, said immunoassay apparatus further comprising:
an optical fiber introducing light which has passed through said cores into said light analyzing means; and
an optical coupler passing light from one of said cores to said optical fiber.

17. An immunoassay apparatus of claim 16, further comprising:
a plurality of light sources, respectively corresponding to said at least two cores, wherein said plurality of light sources are successively turned on one after another so as to introduce light successively to said corresponding respective core.

18. An immunoassay apparatus comprising:
an SPR sensor cell having an SPR sensing portion and a through hole adjacent to said said sensing portion, wherein said through hole has a predetermined thickness dimension sufficient to permit said through hole to serve as a test material holding receptacle;
a light source for emitting light of a predetermined wavelength band into said SPR sensor cell; and
a light analyzing means for analyzing light which has passed through said SPR sensor cell,
wherein said light source comprises a white LED lamp and said SPR sensor cell includes at least two cores arranged in a parallel manner on a plane, each said core surrounded by clads on all sides except two end faces, said light source is arranged in a vicinity of one of said two end faces of one of said SPR sensor cell cores, said light analyzing means arranged to receive light passing through the other of said two end faces, further comprising:
a mover to successively align each said core to said light source and said light analyzing means.

19. An immunoassay apparatus comprising:
an SPR sensor cell having an SPR sensing portion and a through hole adjacent to said said sensing portion, wherein said through hole has a predetermined thickness dimension sufficient to permit said through hole to serve as a test material holding receptacle;
a light source for emitting light of a predetermined wavelength band into said SPR sensor cell; and
a light analyzing means for analyzing light which has passed through said SPR sensor cell,
wherein said light source comprises a white LED lamp and an end surface of said SPR sensor cell where said light is introduced possesses a surface characteristic that tends to suppress introduction of light except for an end surface of said core.

20. An SPR sensor cell comprising:
a core having a rectangular cross section for passing light from a predetermined light source, said core thereby having four side surfaces and two end surfaces;
an SPR sensing portion on a predetermined location of one of said four side surfaces of said core; and
at least two clads formed so as to surround said four side surfaces of said core excluding the SPR sensing portion,
wherein two of said four side surfaces of said core have a low-reflection surface where a light reflection is lowered, said two side surfaces having said low-reflection surface are the two side surfaces other than said one side surface having said SPR sensing portion and a side surface opposite to said surface have said SPR sensing portion.

21. An SPR sensor cell comprising:
a core having a rectangular cross section for passing light from a predetermined light source, said core having an SPR sensing portion on one side surface thereof; and
at least two clads enshrouding said core excluding said SPR sensing portion, said at least two clads having a plurality of surfaces adjacent to said core,
wherein said surfaces of said clads facing the core have a low reflection ratio where a light reflection is lower than a light reflection in said core.

22. An SPR sensor cell of claim 20, wherein said low-reflection surface comprises an obscured glass.

23. An SPR sensor cell of claim 20, wherein said low-reflection surface comprises an aluminum coating.

24. An SPR sensor cell of claim 20, wherein said low-reflection surface comprises a black paint.

25. An SPR sensor cell of claim 20, wherein said four sides surrounded by said shroud are subjected to a surface treatment which makes it difficult to pass light.

26. An immunoassay apparatus comprising:
a SPR sensor cell disclosed in claim 20;
a light source for emitting a predetermined light into said core of said SPR sensor; and
a light analyzer for analyzing a wavelength distribution of the light which has passed through the core.

27. An SPR sensor cell comprising:
at least one sheet-shaped core transmitting light from a light source;
at least one SPR sensing portion on a top surface of said core;
a first clad upon which is mounted said core; and
a second clad having a through hole at a position corresponding to said SPR sensing portion, such that said core is sandwiched between said first clad and said second clad.

28. An SPR sensor of claim 27, wherein an end surface of the core possesses a surface characteristic that makes it difficult to pass the light from the light source (low light transmitting), excluding a core region corresponding to the SPR sensing portion.

29. An SPR sensor cell of claim 28, wherein a plurality of the SPR sensing portions are provided on the core.

30. An SPR sensor cell of claim 29, wherein said at least one core comprises a plurality of light-transparent members having a rectangular cross section and made from an identical material, and wherein light-transparent members having low light transmitting end surface and light-transparent members having no low light transmitting end surface are alternately arranged.

31. An SPR sensor cell of claim 30, wherein each of the light-transparent members having the low lights transmitting end surface has side surfaces (i.e., side surfaces adjacent to the light-transparent members having no low light transmitting end surface) which possess said surface characteristic that it is difficult to pass light.

32. An SPR sensor cell of claim 30, wherein each of the light-transparent members having no low light transmitting end surface has side surface (i.e., side surfaces adjacent to the light-transparent members having the low light transmitting end surface) which side surfaces possess said surface characteristic that it is difficult to pass the light.

33. An immunoassay apparatus comprising:
an SPR sensor cell comprising:
at least one sheet-shaped core transmitting light from a light source;
at least one SPR sensing portion on a top surface of said core;
a first clad upon which is mounted said core; and
a second clad having a through hole at a position corresponding to said SPR sensing portion, such that said core is sandwiched between said first clad and said second clad;
a light source for emitting light into the core of the SPR sensor cell; and
a light analyzing means for analyzing a wavelength distribution of the light emitted from the SPR sensor cell.

34. An immunoassay apparatus of claim 33, wherein at least one pin hole plate is provided in the vicinity of the SPR sensor cell in at least one of before the light enters the SPR sensor cell and after the light comes out of the SPR sensor cell.

35. An immunoassay apparatus of claim 33, further comprising:
a predetermined block member in the vicinity of the SPR sensor cell in at least one of before the light passes the SPR sensor and after the light passes the SPR sensor cell; and
an optical fiber for connecting the block member to the light source or to the light analyzing member, wherein an optical fiber fixing portion is formed in the block member corresponding to the core of the SPR sensor cell, and the optical fiber has an end portion covered with a ferrule, and fixed into the optical fiber fixing portion.

* * * * *